(12) United States Patent
Firminger et al.

(10) Patent No.: US 8,180,890 B2
(45) Date of Patent: *May 15, 2012

(54) HYPOTHESIS BASED SOLICITATION OF DATA INDICATING AT LEAST ONE SUBJECTIVE USER STATE

(75) Inventors: Shawn P. Firminger, Redmond, WA (US); Jason Garms, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 450 days.
This patent is subject to a terminal disclaimer.

(21) Appl. No.: 12/384,660
(22) Filed: Apr. 6, 2009

(65) Prior Publication Data
US 2010/0131435 A1 May 27, 2010

Related U.S. Application Data

(63) Continuation-in-part of application No. 12/313,659, filed on Nov. 21, 2008, now Pat. No. 8,046,455, and a continuation-in-part of application No. 12/315,083, filed on Nov. 26, 2008, now Pat. No. 8,005,948, and a continuation-in-part of application No. 12/319,135, filed on Dec. 31, 2008, now Pat. No. 7,937,465, and a continuation-in-part of application No. 12/319,134, filed on Dec. 31, 2008, now Pat. No. 7,945,632, and a continuation-in-part of application No. 12/378,162, filed on Feb. 9, 2009, now Pat. No. 8,028,063, and a continuation-in-part of application No. 12/378,288, filed on Feb. 11, 2009, now Pat. No. 8,032,628, and a continuation-in-part of application No. 12/380,409, filed on Feb. 25, 2009, now Pat. No. 8,010,662, and a continuation-in-part of application No. 12/380,573, filed on Feb. 26, 2009, and a continuation-in-part of application No. 12/383,581, filed on Mar. 24, 2009, and a continuation-in-part of application No. 12/383,817, filed on Mar. 25, 2009.

(51) Int. Cl.
*G06F 15/16* (2006.01)

(52) U.S. Cl. ........ 709/224; 709/203; 709/226; 709/217; 709/204; 370/231; 370/241; 370/242; 370/249; 707/755; 707/736; 706/11; 706/12; 706/52; 706/58

(58) Field of Classification Search ................ 705/14.4; 706/12, 52, 11, 206; 709/206, 224
See application file for complete search history.

(56) References Cited

U.S. PATENT DOCUMENTS
3,599,149 A 8/1971 Pardoe
(Continued)

FOREIGN PATENT DOCUMENTS
WO WO 99/18842 4/1999

OTHER PUBLICATIONS
Hansen, et al.; "Microblogging—Facilitating Tacit Knowledge?"—A Second Year Term Paper; Information Management Study at Copenhagen Business School; 2008; pp. 1-42; located at http://www.scribd.com/doc/3460679/Microblogging-as-a-Facilitator-for-Tacit-Knowledge.

(Continued)

*Primary Examiner* — Jude Jean Gilles

(57) ABSTRACT

A computationally implemented method includes, but is not limited to: soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and acquiring the subjective user state data including the data indicating incidence of at least one subjective user state associated with the user. In addition to the foregoing, other method aspects are described in the claims, drawings, and text forming a part of the present disclosure.

41 Claims, 30 Drawing Sheets

U.S. PATENT DOCUMENTS

| | | | |
|---|---|---|---|
| 6,697,800 | B1 | 2/2004 | Jannink et al. |
| 7,203,430 | B2 | 4/2007 | Ohta |
| 7,400,928 | B2 | 7/2008 | Hatlestsad |
| 7,627,544 | B2 | 12/2009 | Chkodrov et al. |
| 7,937,465 | B2 * | 5/2011 | Firminger et al. ............ 709/224 |
| 7,945,632 | B2 * | 5/2011 | Firminger et al. ............ 709/206 |
| 8,005,948 | B2 * | 8/2011 | Firminger et al. ............ 709/224 |
| 8,010,604 | B2 * | 8/2011 | Lapstun et al. ............... 709/204 |
| 8,010,662 | B2 * | 8/2011 | Firminger et al. ............ 709/224 |
| 8,028,063 | B2 * | 9/2011 | Firminger et al. ............ 709/224 |
| 8,032,628 | B2 * | 10/2011 | Firminger et al. ............ 709/224 |
| 8,046,455 | B2 * | 10/2011 | Firminger et al. ............ 709/224 |
| 2003/0166277 | A1 | 9/2003 | Zauderer et al. |
| 2004/0010184 | A1 | 1/2004 | Kenknight et al. |
| 2004/0103108 | A1 | 5/2004 | Andreev et al. |
| 2005/0102578 | A1 | 5/2005 | Bliss et al. |
| 2006/0034430 | A1 | 2/2006 | Liakis |
| 2006/0058590 | A1 | 3/2006 | Shaw et al. |
| 2007/0293731 | A1 | 12/2007 | Downs et al. |
| 2008/0034056 | A1 | 2/2008 | Renger et al. |
| 2008/0059232 | A1 | 3/2008 | Iliff |
| 2008/0091515 | A1 | 4/2008 | Thieberger et al. |
| 2008/0215607 | A1 | 9/2008 | Kaushansky et al. |
| 2008/0218472 | A1 | 9/2008 | Breen et al. |
| 2008/0262872 | A1 | 10/2008 | Perry et al. |
| 2009/0049154 | A1 | 2/2009 | Ge |
| 2009/0077658 | A1 | 3/2009 | King et al. |
| 2009/0132197 | A1 | 5/2009 | Rubin et al. |
| 2009/0240647 | A1 | 9/2009 | Green et al. |
| 2009/0276221 | A1 | 11/2009 | Heiman et al. |
| 2009/0326981 | A1 | 12/2009 | Karkanias et al. |
| 2010/0010866 | A1 | 1/2010 | Bal et al. |
| 2010/0088104 | A1 | 4/2010 | DeRemer et al. |
| 2010/0092095 | A1 | 4/2010 | King et al. |

OTHER PUBLICATIONS

Reiss, M.; "Correlations Between Changes in Mental States and Thyroid Activity After Different Forms of Treatment"; The British Journal of Psychology—Journal of Mental Science; bearing dates of Mar. 6, 1954 and 1954; pp. 687-703 [Abstract only provided]; located at http://bjp.rcpsych.org/cgi/content/abstract/100/420/687; The Royal College of Psychiatrists.

Agger, Michael;"Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/462,201, Firminger et al.
U.S. Appl. No. 12/462,128, Firminger et al.
U.S. Appl. No. 12/459,854, Firminger et al.
U.S. Appl. No. 12/459,775, Firminger et al.
U.S. Appl. No. 12/456,433, Firminger et al.
U.S. Appl. No. 12/456,249, Firminger et al.
U.S. Appl. No. 12/455,317, Firminger et al.
U.S. Appl. No. 12/455,309, Firminger et al.
U.S. Appl. No. 12/387,487, Firminger et al.
U.S. Appl. No. 12/387,465, Firminger et al.
U.S. Appl. No. 12/384,779, Firminger et al.
U.S. Appl. No. 12/383,817, Firminger et al.
U.S. Appl. No. 12/383,581, Firminger et al.
U.S. Appl. No. 12/380,573, Firminger et al.
U.S. Appl. No. 12/380,409, Firminger et al.
U.S. Appl. No. 12/378,288, Firminger et al.
U.S. Appl. No. 12/378,162, Firminger et al.
U.S. Appl. No. 12/319,135, Firminger et al.
U.S. Appl. No. 12/319,134, Firminger et al.
U.S. Appl. No. 12/315,083, Firminger et al.
U.S. Appl. No. 12/313,659, Firminger et al.

Buchanan, Matt; "Twitter Toilet Tweets Your Poo"; gizmodo.com; bearing a date of May 18, 2009; pp. 1-2; located at http://gizmodo.com/5259381/twitter-toilet-tweets-your-poo; printed on Jul. 1, 2009.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

Fox, Stuart; "The John, 2.0"; Popular Science; bearing a date of May 18, 2009; pp. 1-2; located at http://www.popsci.com/scietech/article/2009-05/john-20; printed on Jul. 1, 2009.

Frucci, Adam; "SNIF Dog Tags Track What Your Dog Does All Day; Spoiler: Eat, Sleep, Poop"; gizmodo.com; bearing a date of Jun. 10, 2009; pp. 1-2; located at http://i.gizmodo.com/5286076/snif-dog-tags-track-what-your-dog-does-all-day-spoiler-eat-sl...; printed on Jul. 1, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

"hacklab.Toilet—a twitter-enabled toilet at hacklab.to"; aculei.net; bearing a date of May 18, 2009; pp. 1-8; located at http://aculei.net/~shardy/hacklabtoilet/; printed on Jul. 1, 2009.

June, Laura; "Apple patent filing shows off activity monitor for skiers, bikers"; engadget.com; bearing a date of Jun. 11, 2009; pp. 1-8; located at http://www.engadget.com/2009/06/11/apple-patent-filing-shows-off-a...; printed on Jul. 1, 2009.

Kraft, Caleb; "Twittering toilet"; Hack A Day; bearing a date of May 5, 2009; pp. 1-11; located at http://hackaday.com/2009/05/05/twittering-toilet/; printed on Jul. 1, 2009.

"Mobile pollution sensors deployed"; BBC News; bearing a date of Jun. 30, 2009; pp. 1-2; located at http://news.bbc.co.uk/2/hi/science/nature/8126498.stm; printed on Jul. 1, 2009; © BBC MMIX.

Morales, C. Romero et al.; "Using sequential pattern mining for links recommendation in adaptive hypermedia educational systems"; Current Developments in Technology-Assisted Education; bearing a date of 2006; pp. 1016-1020; © FORMATEX 2006.

Nesbit, J.C. et al.; "Sequential pattern analysis software for educational event data"; pp. 1-5.

Oliver, Sam; "Apple developing activity monitor for skiers, snowboarders, bikers"; AppleInsider; bearing a date of Jun. 11, 2009; pp. 1-6; located at http://www.appleinsider.com/articles/09/06/11/apple_developing_act...; printed on Jul. 1, 2009; AppleInsider © 1997-2008.

Rettner, Rachael; "Cell Phones Allow Everyone to Be a Scientist"; LiveScience; bearing a date of Jun. 4, 2009; pp. 1-3; located at http://www.livescience.com/technology/090604-mobile-sensor.html; printed on Jul. 1, 2009; © Imaginova Corp.

SPSS; "Find patterns in data that identify combinations of events that occur together"; SPSS Association Rule Components; bearing a date of 2002; pp. 1-5; © 2002 SPSS Inc.

SPSS; "Find sequential patterns in data to predict events more accurately"; SPSS Sequence Association™ Component; bearing a date of 2002; pp. 1-5; © 2002 SPSS Inc.

Karimi, A. et al.; "A Predictive Location Model for Location-Based Services"; GIS'03; Nov. 7-8, 2003; pp. 126-133; ACM.

Ulicny, B. et al.; "New Metrics for Blog Mining"; Data Mining, Intrusion Detection, Information Assurance, and Data Networks Security 2007; Proceedings of the SPIE; 2007; 12 pages; vol. 6570.

* cited by examiner

101 Subjective User State Data Solicitation Module

- 202 Requesting Module
  - 204 User Interface Requesting Module
    - 205 Request Indication Module
  - 206 Network Interface Requesting Module
    - 207 Request Transmission Module
    - 208 Request Access Module
    - 209 Configuration Module
    - 210 Directing/instructing Module
- 212 Motivation Provision Module
- 214 Selection Request Module
- 216 Confirmation Request Module
- 218 Time/Temporal Element Request Module
- 220 Hypothesis Referencing Module

FIG. 2a

102 Subjective User State Data Acquisition Module

224 Subjective User State Data Reception Module

226 User Interface Reception Module

227 Network Interface Reception Module

228 Time Data Acquisition Module

230 Time Stamp Acquisition Module

231 Time Interval Acquisition Module

232 Temporal Relationship Acquisition Module

FIG. 2b

104 Objective Occurrence Data Acquisition Module

234 Objective Occurrence Data Reception Module

235 User Interface Data Reception Module

236 Network Interface Data Reception Module

238 Time Data Acquisition Module

240 Time Stamp Acquisition Module

241 Time Interval Acquisition Module

FIG. 2c

HYPOTHESIS BASED SOLICITATION OF DATA INDICATING AT LEAST ONE SUBJECTIVE USER STATE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications:

For purposes of the USPTO extra-statutory requirements, the present application constitutes a continuation-in-part of U.S. patent application Ser. No. 12/313,659, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 21 Nov. 2008 now U.S. Pat. No. 8,046,455, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/315,083, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 26 Nov. 2008 now U.S. Pat. No. 8,005,948, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,135, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No. 7,937,465, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,134, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No. 7,945,632, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,162, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 9 Feb. 2009 now U.S. Pat. No. 8,028,063, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,288, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 11 Feb. 2009 now U.S. Pat. No. 8,032,628, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,409, entitled SOLICITING DATA INDICATING AT LEAST ONE SUBJECTIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 25 Feb. 2009 now U.S. Pat. No. 8,010,662, which is currently co-pending, or is an application of which a currently co-pending application is entitled to the benefit of the filing date.

For purpose of the USPTO extra-statutory requirements, the present application Constitutes a continuation-in-part of United States Patent Application No. 12/380,573, Entitled SOLICITING DATA INDICATING AT LEAST ONE SUBJECTIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, file 26 February 2009, which is currently co-pending, or is an application of which a currently co-pending application is entitled to the benefit of the filing date.

For purposes of the USPTO extra-statutory requirements, the present application constitutes a continuation-in-part of United States Patent Application No. 12/383,581, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K.Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 24 Mar. 2009, which is currently co-pending, or is an application of which a currently co-pending application is entitled to the benefit of the filing date.

For purposes of the USPTO extra-statutory requirements, the present application constitutes a continuation-in-part of United States Patent Application No. 12/383,817, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K.Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 25 Mar. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and acquiring the subjective user state data including the data indicating incidence of at least one subjective user state associated with the user. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and means for acquiring the subjective user state data including the data indicating incidence of at least one subjective user state associated with the user. In addition to the foregoing, other system aspects are described in the claims, drawings, and text forming a part of the present disclosure.

A computationally implemented system includes, but is not limited to: circuitry for soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and circuitry for acquiring the subjective user state data including the data indicating incidence of at least one subjective user state associated with the user. In addition to the foregoing, other system aspects are described in the claims, drawings, and text forming a part of the present disclosure.

A computer program product including a signal-bearing medium bearing one or more instructions soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and one or more instructions for acquiring the subjective user state data including the data indicating incidence of at least one subjective user state associated with the user. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2*a* shows another perspective of the subjective user state data solicitation module 101 of the computing device 10 of FIG. 1*b*.

FIG. 2*b* shows another perspective of the subjective user state data acquisition module 102 of the computing device 10 of FIG. 1*b*.

FIG. 2c shows another perspective of the objective occurrence data acquisition module 104 of the computing device 10 of FIG. 1b.

DETAILED DESCRIPTION

Figure 1A:
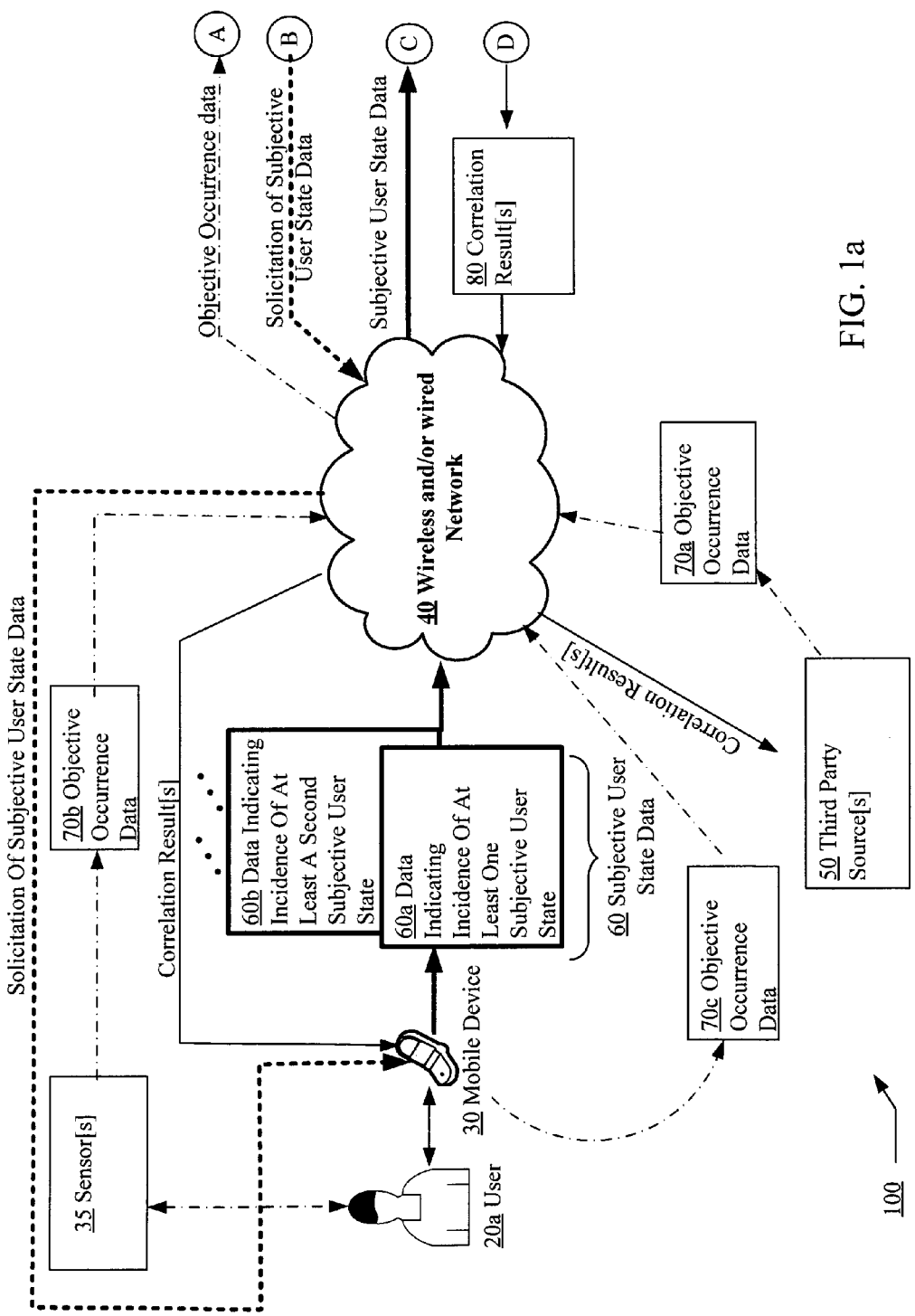
FIGS. 1*a* and 1*b* show a high-level block diagram of a mobile device 30 and a computing device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that is becoming increasingly popular in the computing/ communication field is to electronically record one's feelings, thoughts, and other aspects of the person's everyday life onto an open diary. One place where such open diaries are maintained are at social networking sites commonly known as "blogs" where one or more users may report or post their thoughts and opinions on various topics, latest news, current events, and various other aspects of the users' everyday life. The process of reporting or posting blog entries is commonly referred to as blogging. Other social networking sites may allow users to update their personal information via, for example, social network status reports in which a user may report or post for others to view the latest status or other aspects of the user.

A more recent development in social networking is the introduction and explosive growth of microblogs in which individuals or users (referred to as "microbloggers") maintain open diaries at microblog websites (e.g., otherwise known as "twitters") by continuously or semi-continuously posting microblog entries. A microblog entry (e.g., "tweet") is typically a short text message that is usually not more than 140 characters long. The microblog entries posted by a microblogger may report on any aspect of the microblogger's daily life.

The various things that are typically posted through microblog entries may be categorized into one of at least two possible categories. The first category of things that may be reported through microblog entries are "objective occurrences" that may or may not be associated with the microblogger. Objective occurrences that are associated with a microblogger may be any characteristic, event, happening, or any other aspects associated with or are of interest to the microblogger that can be objectively reported by the microblogger, a third party, or by a device. These things would include, for example, food, medicine, or nutraceutical intake of the microblogger, certain physical characteristics of the microblogger such as blood sugar level or blood pressure that can be objectively measured, daily activities of the microblogger observable by others or by a device, performance of the stock market (which the microblogger may have an interest in), and so forth. In some cases, objective occurrences may not be at least directly associated with a microblogger. Examples of such objective occurrences include, for example, external events that may not be directly related to the microblogger such as the local weather, activities of others (e.g., spouse or boss) that may directly or indirectly affect the microblogger, and so forth.

A second category of things that may be reported or posted through microblog entries include "subjective user states" of the microblogger. Subjective user states of a microblogger include any subjective state or status associated with the microblogger that can only be typically reported by the microblogger (e.g., generally cannot be reported by a third party or by a device). Such states including, for example, the subjective mental state of the microblogger (e.g., "I am feeling happy"), the subjective physical state of the microblogger (e.g., "my ankle is sore" or "my ankle does not hurt anymore" or "my vision is blurry"), and the subjective overall state of the microblogger (e.g., "I'm good" or "I'm well"). Note that the term "subjective overall state" as will be used herein refers to those subjective states that may not fit neatly into the other two categories of subjective user states described above (e.g., subjective mental states and subjective physical states). Although microblogs are being used to provide a wealth of personal information, they have thus far been primarily limited to their use as a means for providing commentaries and for maintaining open diaries.

In accordance with various embodiments, methods, systems, and computer program products are provided to, among other things, solicit and acquire subjective user state data including soliciting and acquiring data indicating incidence of at least one subjective user state associated with a user, the solicitation being indirectly or directly prompted based, at least in part on a hypothesis that links one or more subjective user states with one or more objective occurrences and in response to an incidence of at least one objective occurrence.

In various embodiments, a hypothesis may be defined by a sequential pattern that indicates or suggests a temporal or specific time sequencing relationship between one or more subjective user states and one or more objective occurrences. In some cases, the one or more subjective user states associated with the hypothesis may be based on past incidences of one or more subjective user states associated with a user, with multiple users, with a sub-group of the general population, or with the general population. Similarly, the one or more objective occurrences associated with the hypothesis may be based on past incidences of objective occurrences.

In some cases, a hypothesis may be formulated when it is determined that a particular pattern of events (e.g., incidences of one or more subjective user states and one or more objective occurrences) occurs repeatedly with respect to a particular user, a group of users, a subset of the general population, or the general population. For example, a hypothesis may be formulated that suggests or predicts that a person will likely have an upset stomach after eating a hot fudge sundae when it is determined that multiple users had reported having an upset stomach after eating a hot fudge sundae. In other cases, a hypothesis may be formulated based, at least in part, on a single pattern of events and historical data related to such events. For instance, a hypothesis may be formulated when a person reports that he had a stomach ache after eating a hot fudge sundae, and historical data suggests that a segment of the population may not be able to digest certain nutrients included in a hot fudge sundae (e.g., the hypothesis would suggest or indicate that the person may get stomach aches whenever the person eats a hot fudge sundae).

The subjective user state data to be acquired by the methods, systems, and the computer program products may include data indicating the incidence of at least one subjective user state associated with a user. Such subjective user state data together with objective occurrence data including data indicating incidence of at least one objective occurrence may then be correlated. The results of the correlation may be presented in a variety of different forms and may, in some cases, confirm the veracity of the hypothesis. The results of the correlation, in various embodiments, may be presented to the user, to other users, or to one or more third parties as will further described herein.

In some embodiments, the correlation of the acquired subjective user state data with the objective occurrence data may facilitate in determining a causal relationship between at least one objective occurrence (e.g., cause) and at least one subjective user state (e.g., result). For example, determining whenever a user eats a banana the user always or sometimes feels good. Note that an objective occurrence does not need to occur prior to a corresponding subjective user state but instead, may occur subsequent or at least partially concurrently with the incidence of the subjective user state. For example, a person may become "gloomy" (e.g., subjective user state) whenever it is about to rain (e.g., objective occurrence) or a person may become gloomy while (e.g., concurrently) it is raining.

As briefly described earlier, the subjective user state data to be acquired may include data that indicate the incidence or occurrence of at least one subjective user state associated with a user. In situations where the subjective user state data to be acquired indicates multiple subjective user states, each of the subjective user states indicated by the acquired subjective user state data may be solicited, while in other embodiments, only one or a subset of the subjective user states indicated by the acquired subjective user state data may be solicited. A "subjective user state" is in reference to any subjective user state or status associated with a user (e.g., a blogger or microblogger) at any moment or interval in time that only the user can typically indicate or describe. Such states include, for example, the subjective mental state of the user (e.g., user is feeling sad), the subjective physical state (e.g., physical characteristic) of the user that only the user can typically indicate (e.g., a backache or an easing of a backache as opposed to blood pressure which can be reported by a blood pressure device and/or a third party), and the subjective overall state of the user (e.g., user is "good").

Examples of subjective mental states include, for example, happiness, sadness, depression, anger, frustration, elation, fear, alertness, sleepiness, and so forth. Examples of subjective physical states include, for example, the presence, easing, or absence of pain, blurry vision, hearing loss, upset stomach, physical exhaustion, and so forth. Subjective overall states may include any subjective user states that cannot be easily categorized as a subjective mental state or as a subjective physical state. Examples of subjective overall states include, for example, the user "being good," "bad," "exhausted," "lack of rest," "wellness," and so forth.

In contrast, "objective occurrence data," as will be described herein, may include data that indicate incidence of at least one objective occurrence. In some embodiments, an objective occurrence may be any physical characteristic, event, happenings, or any other aspect that may be associated with, is of interest to, or may somehow impact a user that can be objectively reported by at least a third party or a sensor device. Note, however, that an objective occurrence does not have to be actually reported by a sensor device or by a third party, but instead, may be reported by the user himself or herself (e.g., via microblog entries). Examples of objectively reported occurrences that could be indicated by the objective occurrence data include, for example, a user's food, medicine, or nutraceutical intake, the user's location at any given point in time, a user's exercise routine, a user's physiological characteristics such as blood pressure, social or professional activities, the weather at a user's location, activities associated with third parties, occurrence of external events such as the performance of the stock market, and so forth.

The term "correlating" as will be used herein may be in reference to a determination of one or more relationships between at least two variables. Alternatively, the term "correlating" may merely be in reference to the linking or associating of the at least two variables. In the following exemplary embodiments, the first variable is subjective user state data that indicates at least one subjective user state and the second variable is objective occurrence data that indicates at least one objective occurrence. In embodiments where the subjective user state indicates multiple subjective user states, each of the subjective user states indicated by the subjective user state data may represent different incidences of the same or similar type of subjective user state (e.g., happiness). Alternatively, the subjective user state data may indicate multiple subjective user states that represent different incidences of different types of subjective user states (e.g., happiness and sadness).

Similarly, in some embodiments where the objective occurrence data may indicate multiple objective occurrences, each of the objective occurrences indicated by the objective occurrence data may represent different incidences of the same or similar type of objective occurrence (e.g., exercising). In alternative embodiments, however, each of the objective occurrences indicated by the objective occurrence data may represent different incidences of different types of objective occurrence (e.g., user exercising and user resting).

Various techniques may be employed for correlating subjective user state data with objective occurrence data in various alternative embodiments. For example, in some embodiments, the correlation of the objective occurrence data with the subjective user state data may be accomplished by determining a sequential pattern associated with at least one subjective user state indicated by the subjective user state data and at least one objective occurrence indicated by the objective occurrence data. In other embodiments, the correlation of the objective occurrence data with the subjective user state data may involve determining multiple sequential patterns associated with multiple subjective user states and multiple objective occurrences.

A sequential pattern, as will be described herein, may define time and/or temporal relationships between two or more events (e.g., one or more subjective user states and one or more objective occurrences). In order to determine a sequential pattern, subjective user state data including data indicating incidence of at least one subjective user state associated with a user may be solicited, the solicitation being prompted based, at least in part, on a hypothesis linking one or more subjective user states with one or more objective occurrences and in response, at least in part, to an incidence of at least one objective occurrence.

For example, suppose a hypothesis suggests that a user or a group of users tend to be depressed whenever the weather is bad (e.g., cloudy or overcast weather), the hypothesis being formed, for example, based at least in part on reported past events (e.g., reported past subjective user states of a user or a group of users and reported past objective occurrences). Then upon the weather turning bad, and based at least in part on the hypothesis, subjective user state data including data indicating incidence of at least one subjective user state associated with a user may be solicited from, for example, the user (or from other sources such as third party sources). If, after soliciting for the subjective user state data, data indeed is acquired that indicates that the user felt depressed when the weather turned bad, this may confirm the veracity of the hypothesis.

On the other hand, if the data that is acquired after the solicitation indicates that the user was happy when the weather turned bad, this may indicate that there is a weaker correlation or link between depression and bad weather.

As briefly described above, a hypothesis may be represented by a sequential pattern that may merely indicate or represent the temporal relationship or relationships between at least one subjective user state and at least one objective occurrence (e.g., whether the incidence or occurrence of at least one subjective user state occurred before, after, or at least partially concurrently with the incidence of the at least one objective occurrence). In alternative implementations, and as will be further described herein, a sequential pattern may indicate a more specific time relationship between the incidences of one or more subjective user states and the incidences of one or more objective occurrences. For example, a sequential pattern may represent the specific pattern of events (e.g., one or more objective occurrences and one or more subjective user states) that occurs along a timeline.

The following illustrative example is provided to describe how a sequential pattern associated with at least one subjective user state and at least one objective occurrence may be determined based, at least in part, on the temporal relationship between the incidence of at least one subjective user state and the incidence of at least one objective occurrence in accordance with some embodiments. For these embodiments, the determination of a sequential pattern may initially involve determining whether the incidence of the at least one subjective user state occurred within some predefined time increment from the incidence of the one objective occurrence. That is, it may be possible to infer that those subjective user states that did not occur within a certain time period from the incidence of an objective occurrence are not related or are unlikely related to the incidence of that objective occurrence.

For example, suppose a user during the course of a day eats a banana and also has a stomach ache sometime during the course of the day. If the consumption of the banana occurred in the early morning hours but the stomach ache did not occur until late that night, then the stomach ache may be unrelated to the consumption of the banana and may be disregarded. On the other hand, if the stomach ache had occurred within some predefined time increment, such as within 2 hours of consumption of the banana, then it may be concluded that there is a link between the stomach ache and the consumption of the banana. If so, a temporal relationship between the consumption of the banana and the occurrence of the stomach ache may be established. Such a temporal relationship may be represented by a sequential pattern. Such a sequential pattern may simply indicate that the stomach ache (e.g., a subjective user state) occurred after (rather than before or concurrently) the consumption of banana (e.g., an objective occurrence).

Other factors may also be referenced and examined in order to determine a sequential pattern and whether there is a relationship (e.g., causal relationship) between an incidence of an objective occurrence and an incidence of a subjective user state. These factors may include, for example, historical data (e.g., historical medical data such as genetic data or past history of the user or historical data related to the general population regarding, for example, stomach aches and bananas) as briefly described above.

In some implementations, a sequential pattern may be determined for multiple subjective user states and multiple objective occurrences. Such a sequential pattern may particularly map the exact temporal or time sequencing of the various events (e.g., subjective user states and/or objective occurrences). The determined sequential pattern may then be used to provide useful information to the user and/or third parties.

The following is another illustrative example of how subjective user state data may be correlated with objective occurrence data by determining multiple sequential patterns and comparing the sequential patterns with each other. Suppose, for example, a user such as a microblogger reports that the user ate a banana on a Monday. The consumption of the banana, in this example, is a reported incidence of a first objective occurrence associated with the user. The user then reports that 15 minutes after eating the banana, the user felt very happy. The reporting of the emotional state (e.g., felt very happy) is, in this example, a reported incidence of a first subjective user state. Thus, the reported incidence of the first objective occurrence (e.g., eating the banana) and the reported incidence of the first subjective user state (user felt very happy) on Monday may be represented by a first sequential pattern.

On Tuesday, the user reports that the user ate another banana (e.g., a second objective occurrence associated with the user). The user then reports that 20 minutes after eating the second banana, the user felt somewhat happy (e.g., a second subjective user state). Thus, the reported incidence of the second objective occurrence (e.g., eating the second banana) and the reported incidence of the second subjective user state (user felt somewhat happy) on Tuesday may be represented by a second sequential pattern. Under this scenario, the first sequential pattern may represent a hypothesis that links feeling happy or very happy (e.g., a subjective user state) with eating a banana (e.g., an objective occurrence). Alternatively, the first sequential pattern may merely represent historical data (e.g., historical sequential pattern). Note that in this example, the occurrences of the first subjective user state and the second subjective user state may be indicated by subjective user state data while the occurrences of the first objective occurrence and the second objective occurrence may be indicated by objective occurrence data.

In a slight variation of the above example, suppose the user had forgotten to report for Tuesday the feeling of being somewhat happy but does report consuming the second banana on Tuesday. This may result in the user being asked, based at least in part on the reporting of the user consuming the banana on Tuesday, and based at least in part on the hypothesis, as to how the user felt on Tuesday or how the user felt after eating the banana on Tuesday. Upon the user indicating feeling somewhat happy on Tuesday, a second sequential pattern may be determined.

In any event, by comparing the first sequential pattern with the second sequential pattern, the subjective user state data may be correlated with the objective occurrence data. Such a comparison may confirm the veracity of the hypothesis. In some implementations, the comparison of the first sequential pattern with the second sequential pattern may involve trying to match the first sequential pattern with the second sequential pattern by examining certain attributes and/or metrics. For example, comparing the first subjective user state (e.g., user felt very happy) of the first sequential pattern with the second subjective user state (e.g., user felt somewhat happy) of the second sequential pattern to see if they at least substantially match or are contrasting (e.g., being very happy in contrast to being slightly happy or being happy in contrast to being sad). Similarly, comparing the first objective occurrence (e.g., eating a banana) of the first sequential pattern may be compared to the second objective occurrence (e.g., eating of another banana) of the second sequential pattern to determine whether they at least substantially match or are contrasting.

A comparison may also be made to determine if the extent of time difference (e.g., 15 minutes) between the first subjective user state (e.g., user being very happy) and the first objective occurrence (e.g., user eating a banana) matches or are at least similar to the extent of time difference (e.g., 20 minutes) between the second subjective user state (e.g., user being somewhat happy) and the second objective occurrence (e.g., user eating another banana). These comparisons may be made in order to determine whether the first sequential pattern matches the second sequential pattern. A match or substantial match would suggest, for example, that a subjective user state (e.g., happiness) is linked to a particular objective occurrence (e.g., consumption of banana). In other words, confirming the hypothesis that happiness may be linked to the consumption of bananas.

As briefly described above, the comparison of the first sequential pattern with the second sequential pattern may include a determination as to whether, for example, the respective subjective user states and the respective objective occurrences of the sequential patterns are contrasting subjective user states and/or contrasting objective occurrences. For example, suppose in the above example the user had reported that the user had eaten a whole banana on Monday and felt very energetic (e.g., first subjective user state) after eating the whole banana (e.g., first objective occurrence). Suppose that the user also reported that on Tuesday he ate a half a banana instead of a whole banana and only felt slightly energetic (e.g., second subjective user state) after eating the half banana (e.g., second objective occurrence). In this scenario, the first sequential pattern (e.g., feeling very energetic after eating a whole banana) may be compared to the second sequential pattern (e.g., feeling slightly energetic after eating only a half of a banana) to at least determine whether the first subjective user state (e.g., being very energetic) and the second subjective user state (e.g., being slightly energetic) are contrasting subjective user states. Another determination may also be made during the comparison to determine whether the first objective occurrence (eating a whole banana) is in contrast with the second objective occurrence (e.g., eating a half of a banana).

In doing so, an inference may be made that eating a whole banana instead of eating only a half of a banana makes the user happier or eating more banana makes the user happier. Thus, the word "contrasting" as used here with respect to subjective user states refers to subjective user states that are the same type of subjective user states (e.g., the subjective user states being variations of a particular type of subjective user states such as variations of subjective mental states). Thus, for example, the first subjective user state and the second subjective user state in the previous illustrative example are merely variations of subjective mental states (e.g., happiness). Similarly, the use of the word "contrasting" as used here with respect to objective occurrences refers to objective states that are the same type of objective occurrences (e.g., consumption of food such as banana).

As those skilled in the art will recognize, a stronger correlation between the subjective user state data and the objective occurrence data could be obtained if a greater number of sequential patterns (e.g., if there was a third sequential pattern, a fourth sequential pattern, and so forth, that indicated that the user became happy or happier whenever the user ate bananas) are used as a basis for the correlation. Note that for ease of explanation and illustration, each of the exemplary sequential patterns to be described herein will be depicted as a sequential pattern of an incidence of a single subjective user state and an incidence of a single objective occurrence. However, those skilled in the art will recognize that a sequential pattern, as will be described herein, may also be associated with incidences or occurrences of multiple objective occurrences and/or multiple subjective user states. For example, suppose the user had reported that after eating a banana, he had gulped down a can of soda. The user then reported that he became happy but had an upset stomach. In this example, the sequential pattern associated with this scenario will be associated with two objective occurrences (e.g., eating a banana and drinking a can of soda) and two subjective user states (e.g., user having an upset stomach and feeling happy).

In some embodiments, and as briefly described earlier, the sequential patterns derived from subjective user state data and objective occurrence data may be based on temporal relationships between objective occurrences and subjective user states. For example, whether a subjective user state occurred before, after, or at least partially concurrently with an objective occurrence. For instance, a plurality of sequential patterns derived from subjective user state data and objective occurrence data may indicate that a user always has a stomach ache (e.g., subjective user state) after eating a banana (e.g., first objective occurrence).

Figure 1B:
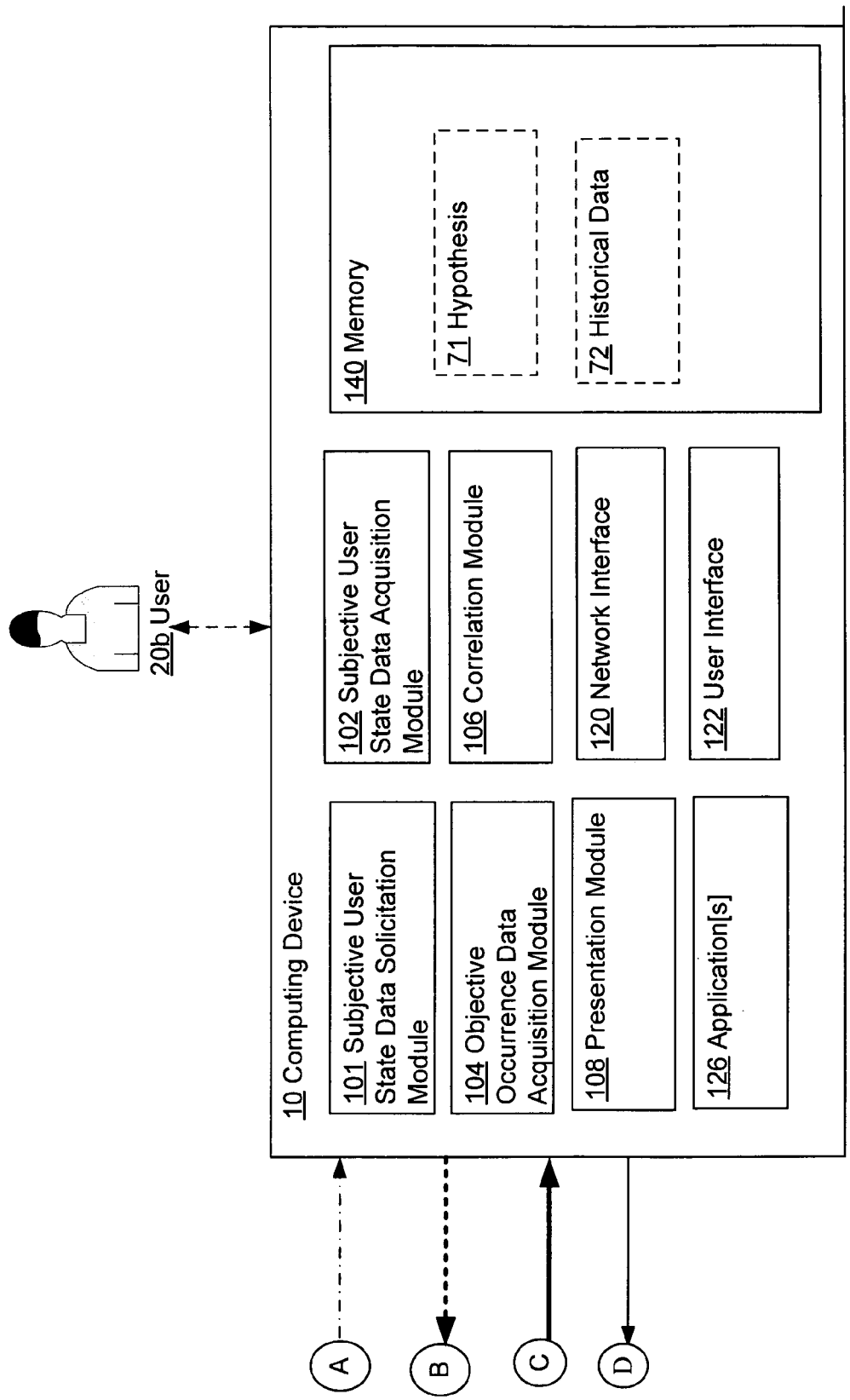

FIGS. 1a and 1b illustrate an example environment in accordance with various embodiments. In the illustrated environment, an exemplary system 100 may include at least a computing device 10 (see FIG. 1b). The computing device 10, which may be a server (e.g., network server) or a standalone device, may be employed in order to, among other things, acquire objective occurrence data 70* including data indicating occurrence of at least one objective occurrence, to solicit and acquire subjective user state data 60 including data indicating incidence of at least one subjective user state 60a associated with a user 20*, and to correlate the subjective user state data 60 with the objective occurrence data 70*. In embodiments in which the computing device 10 is a server, the exemplary system 100 may also include a mobile device 30 to at least solicit and acquire the subjective user state data 60 including the data indicating incidence of at least one subjective user state 60a in response to, for example, a request made by the computing device 10 for subjective user state data 60. Note that in the following, "*" indicates a wildcard. Thus, user 20* may indicate a user 20a or a user 20b of FIGS. 1a and 1b.

As previously indicated, in some embodiments, the computing device 10 may be a network server in which case the computing device 10 may communicate with a user 20a via a mobile device 30 and through a wireless and/or wired network 40. A network server, as will be described herein, may be in reference to a server located at a single network site or located across multiple network sites or a conglomeration of servers located at multiple network sites. The mobile device 30 may be a variety of computing/communication devices including, for example, a cellular phone, a personal digital assistant (PDA), a laptop, a desktop, or other types of computing/communication device that can communicate with the computing device 10.

In alternative embodiments, the computing device 10 may be a standalone computing device 10 (or simply "standalone device") that communicates directly with a user 20b. For these embodiments, the computing device 10 may be any type of handheld device such as a cellular telephone, a PDA, or other types of computing/communication devices such as a laptop computer, a desktop computer, and so forth. In various embodiments, the computing device 10 (as well as the mobile device 30) may be a peer-to-peer network component device. In some embodiments, the computing device 10 may operate via a web 2.0 construct.

In embodiments where the computing device 10 is a server, the computing device 10 may solicit and acquire the subjective user state data 60 indirectly from a user 20a via a network interface 120 and via mobile device 30. In alternative embodiments in which the computing device 10 is a local device such as a handheld device (e.g., cellular telephone, personal digital assistant, etc.), the subjective user state data 60 may be directly obtained from a user 20b via a user interface 122. As will be further described, the computing device 10 may acquire the objective occurrence data 70* from one or more alternative sources.

In various embodiments, and regardless of whether the computing device 10 is a server or a standalone device, the computing device 10 may have access to at least one hypothesis 71. For example, in some situations, a hypothesis 71 may have been generated based on reported past events including past incidences of one or more subjective user states (which may be associated with a user 20*, a group of users 20*, a portion of the general population, or the general population) and past incidences of one or more objective occurrences. Such a hypothesis 71, in some instances, may be stored in a memory 140 to be easily accessible.

For ease of illustration and explanation, the following systems and operations to be described herein will be generally described in the context of the computing device 10 being a network server. However, those skilled in the art will recognize that these systems and operations may also be implemented when the computing device 10 is a standalone device such as a handheld device that may communicate directly with a user 20b.

The computing device 10, in various implementations, may be configured to solicit subjective user state data 60 including soliciting data indicating incidence of at least one subjective user state 60a associated with a user 20a from the user 20a via the mobile device 30. The solicitation of the data indicating incidence of at least one subjective user state 60a may be based, at least in part, on a hypothesis 71 and in response, at least in part, to an incidence of at least one objective occurrence. In the case where the computing device 10 is a server, the computing device, based at least in part, on the hypothesis 71 and in response to the incidence of the at least one objective occurrence, may generate and transmit a solicitation or a request for the data indicating incidence of at least one subjective user state 60a to the mobile device 30. The mobile device 30, in response, may either directly provide the data indicating incidence of at least one subjective user state 60a (if it already has such data) or may solicit such data from the user 20a in order to pass along such data to the computing device 10.

In the case where the computing device 10 is a standalone device, the computing device 10, may be configured to solicit subjective user state data 60 including soliciting data indicating incidence of at least one subjective user state 60a associated with a user 20b directly from a user 20b via a user interface 122. After soliciting for the subjective user state data 60 including the data indicating incidence of at least one subjective user state 60a, the computing device 10 (e.g., either in the case where the computing device 10 is a server or in the case where the computing device 10 is a standalone device) may be further designed to acquire the data indicating incidence of at least one subjective user state 60a as well as to acquire other data indicating other incidences of subjective user states associated with a user 20* (e.g., data indicating incidence of at least a second subjective user state 60b, and so forth) from the user 20* via the mobile device 30 or via the user interface 122.

Examples of subjective user states that may be indicated by the subjective user state data 60 include, for example, subjective mental states of a user 20* (e.g., user 20* is sad or angry), subjective physical states of the user 20* (e.g., physical or physiological characteristic of the user 20* such as the presence, absence, elevating, or easing of a pain), subjective overall states of the user 20* (e.g., user 20* is "well"), and/or other subjective user states that only the user 20* can typically indicate.

In some implementations, the computing device 10 may also be configured to acquire objective occurrence data 70* including data indicating incidence of at least one objective occurrence via a network interface 120 or via user interface 122 (in the case where the computing device 10 is a standalone device). In some implementations, the objective occurrence data 70* to be acquired may further include additional data such as data indicating incidences of one or more additional objective occurrences (e.g., data indicating occurrence of at least a second objective occurrence). The objective occurrence data 70* may be provided by a user 20*, by one or more third party sources 50 (e.g., one or more third parties), or by one or more sensors 35.

For example, in some embodiments, objective occurrence data 70a may be acquired from one or more third party sources 50. Examples of third party sources 50 include, for example, other users, medical entities such as medical or dental clinics and hospitals, content providers, employers, fitness centers, social organizations, and so forth.

In some embodiments, objective occurrence data 70b may be acquired from one or more sensors 35 that may be designed for sensing or monitoring various aspects associated with the user 20a (or user 20b). For example, in some implementations, the one or more sensors 35 may include a global positioning system (GPS) device for determining the location of the user 20a and/or a physical activity sensor for measuring physical activities of the user 20a. Examples of a physical activity sensor include, for example, a pedometer for measuring physical activities of the user 20a. In certain implementations, the one or more sensors 35 may include one or more physiological sensor devices for measuring physiological characteristics of the user 20a. Examples of physiological sensor devices include, for example, a blood pressure monitor, a heart rate monitor, a glucometer, and so forth. In some implementations, the one or more sensors 35 may include one or more image capturing devices such as a video or digital camera.

In some embodiments, objective occurrence data 70c may be acquired from a user 20a via the mobile device 30 (or from user 20b via user interface 122). For these embodiments, the objective occurrence data 70c may be in the form of blog entries (e.g., microblog entries), status reports, or other types of electronic entries (e.g., diary or calendar entries) or messages. In various implementations, the objective occurrence data 70c acquired from a user 20* may indicate, for example, activities (e.g., exercise or food or medicine intake) performed by the user 20*, certain physical characteristics (e.g., blood pressure or location) associated with the user 20*, or other aspects associated with the user 20* that the user 20* can report objectively. The objective occurrence data 70c may be in the form of a text data, audio or voice data, or image data.

In various embodiments, after acquiring the subjective user state data 60 including data indicating incidence of at least one subjective user state 60a and the objective occurrence data 70* including data indicating incidence of at least one objective occurrence, the computing device 10 may be configured to correlate the acquired subjective user state data 60 with the acquired objective occurrence data 70* by, for example, determining whether there is a sequential relationship between the one or more subjective user states as indicated by the acquired subjective user state data 60 and the one or more objective occurrences indicated by the acquired objective occurrence data 70*.

In some embodiments, and as will be further explained in the operations and processes to be described herein, the computing device 10 may be further configured to present one or more results of correlation. In various embodiments, the one or more correlation results 80 may be presented to a user 20* and/or to one or more third parties in various forms (e.g., in the form of an advisory, a warning, a prediction, and so forth). The one or more third parties may be other users 20* (e.g., microbloggers), health care providers, advertisers, and/or content providers.

As illustrated in FIG. 1b, computing device 10 may include one or more components and/or sub-modules. As those skilled in the art will recognize, these components and sub-modules may be implemented by employing hardware (e.g., in the form of circuitry such as application specific integrated circuit or ASIC, field programmable gate array or FPGA, or other types of circuitry), software, a combination of both hardware and software, or a general purpose computing device executing instructions included in a signal-bearing medium. In various embodiments, computing device 10 may include a subjective user state data solicitation module 101, a subjective user state data acquisition module 102, an objective occurrence data acquisition module 104, a correlation module 106, a presentation module 108, a network interface 120 (e.g., network interface card or NIC), a user interface 122 (e.g., a display monitor, a touchscreen, a keypad or keyboard, a mouse, an audio system including a microphone and/or speakers, an image capturing system including digital and/or video camera, and/or other types of interface devices), one or more applications 126 (e.g., a web 2.0 application, a voice recognition application, and/or other applications), and/or memory 140, which may include at least one hypothesis 71 and historical data 72.

FIG. 2a illustrates particular implementations of the subjective user state data solicitation module 101 of the computing device 10 of FIG. 1b. The subjective user state data solicitation module 101 may be configured to solicit at least some subjective user state data 60 including soliciting data indicating incidence of at least one subjective user state 60a associated with a user 20*. In various implementations, the solicitation of the data indicating incidence of at least one subjective user state 60a may be prompted based, at least in part, on a hypothesis 71 that links one or more objective occurrences with one or more subjective user states and in response, at least in part, to incidence of at least one objective occurrence. For example, if an occurrence or incidence of an objective occurrence (e.g., consumption of alcohol by a user 20*) has been reported, and if the hypothesis 71 links the same type of objective occurrence (e.g., consuming alcohol) to a subjective user state (e.g., a hangover), then the solicitation of the data indicating incidence of at least one subjective user state 60a may be to solicit data that would indicate the subjective user state of the user 20* following the consumption of the alcohol by the user 20*.

The subjective user state data solicitation module 101 may include one or more sub-modules in various alternative implementations. For example, in various implementations, the subjective user state data solicitation module 101 may include a requesting module 202 configured to request for data indicating incidence of at least one subjective user state 60a associated with a user 20*. The requesting module 202 may further include one or more sub-modules. For example, in some implementations, such as when the computing device 10 is a standalone device, the requesting module 202 may include a user interface requesting module 204 configured to request for data indicating incidence of at least one subjective user state 60a associated with a user 20b via a user interface 122. The user interface requesting module 204, in some cases, may further include a request indication module 205 configured to indicate a request for data indicating incidence of at least one subjective user state 60a associated with a user 20b via the user interface 122 (e.g., indicating through at least a display system including a display monitor or touchscreen, or an audio system including a speaker).

In some implementations, such as when the computing device 10 is a server, the requesting module 202 may include a network interface requesting module 206 configured to request for data indicating incidence of at least one subjective user state 60a associated with a user 20a via a network interface 120. The network interface requesting module 206 may further include one or more sub-modules in various alternative implementations. For example, in some implementations, the network interface requesting module 206 may include a request transmission module 207 configured to transmit a request to be provided with data indicating incidence of at least one subjective user state 60a associated with a user 20a. Alternatively or in the same implementations, the network interface requesting module 206 may include a request access module 208 configured to transmit data indicating incidence of at least one subjective user state 60a associated with the user 20a a request to have access to data indicating incidence of at least one subjective user state 60a associated with a user 20a.

In the same or different implementations, the network interface requesting module 206 may include a configuration module 209 designed to configure (e.g., remotely configure) one or more remote devices (e.g., a remote network server, a mobile device 30, or some other network device) to provide data indicating incidence of at least one subjective user state 60a associated with a user 20a. In the same or different implementations, the network interface requesting module 206 may include a directing/instructing module 210 configured to direct or instruct a remote device (e.g., transmitting directions or instructions to the remote device such as a remote network server or the mobile device 30) to provide data indicating incidence of at least one subjective user state 60a associated with a user 20a.

The requesting module 202 may include other sub-modules in various alternative implementations. These sub-modules may be included with the requesting module 202 regardless of whether the computing device 10 is a server or a standalone device. For example, in some implementations, the requesting module 202 may include a motivation provision module 212 configured to provide, among other things, a motivation for requesting for data indicating incidence of at least one subjective user state 60a associated with a user 20*. In the same or different implementations, the requesting module 202 may include a selection request module 214 configured to, among other things, request a user 20* for a selection of a subjective user state from a plurality of indicated alternative subjective user states (e.g., asking the user 20* through the user interface 122* to select from alternative choices of "happy," "sad," "in pain," and "upset stomach").

In the same or different implementations, the requesting module 202 may include a confirmation request module 216 configured to request confirmation of an incidence of at least one subjective user state (e.g., asking a user 20* through the user interface 122* whether the user feels "well") associated with a user 20*. In the same or different implementations, the requesting module 202 may include a time/temporal element request module 218 configured to, among other things, request for an indication of a time or temporal element associated with an incidence of at least one subjective user state associated with the user 20* (e.g., asking the user 20* via the user interface 122 whether the user 20* felt tired after lunch?).

In various implementations, the subjective user state data solicitation module 101 of FIG. 2a may include a hypothesis referencing module 220 configured to, among other things, reference at least one hypothesis 71, which in some cases, may be stored in memory 140.

FIG. 2b illustrates particular implementations of the subjective user state data acquisition module 102 of the computing device 10 of FIG. 1b. In brief, the subjective user state data acquisition module 102 may be designed to, among other things, acquire subjective user state data 60 including data indicating at least one subjective user state 60a associated with a user 20*. In various embodiments, the subjective user state data acquisition module 102 may include a subjective user state data reception module 224 configured to receive subjective user state data 60. In some implementations, the subjective user state data reception module 224 may further include a user interface reception module 226 configured to receive, via a user interface 122, subjective user state data 60 including data indicating incidence of at least one subjective user state 60a associated with a user 20*. In the same or different implementations, the subjective user state data reception module 224 may include a network interface reception module 227 configured to receive, via a network interface 120, subjective user state data 60 including data indicating incidence of at least one subjective user state 60a associated with a user 20*.

The subjective user state data acquisition module 102, in various implementations, may include a time data acquisition module 228 configured to acquire (e.g., receive or generate) time and/or temporal elements associated with one or more subjective user states associated with a user 20*. In some implementations, the time data acquisition module 228 may include a time stamp acquisition module 230 for acquiring (e.g., acquiring either by receiving or by generating) one or more time stamps associated with one or more subjective user states associated with a user 20*. In the same or different implementations, the time data acquisition module 228 may include a time interval acquisition module 231 for acquiring (e.g., either by receiving or generating) indications of one or more time intervals associated with one or more subjective user states associated with a user 20*. In the same or different implementations, the time data acquisition module 228 may include a temporal relationship acquisition module 232 for acquiring indications of temporal relationships between objective occurrences and subjective user states (e.g., an indication that a subjective user state associated with a user 20* occurred before, after, or at least partially concurrently with incidence of an objective occurrence).

FIG. 2c illustrates particular implementations of the objective occurrence data acquisition module 104 of the computing device 10 of FIG. 1b. In brief, the objective occurrence data acquisition module 104 may be configured to, among other things, acquire objective occurrence data 70* including data indicating incidence of at least one objective occurrence. As further illustrated, in some implementations, the objective occurrence data acquisition module 104 may include an objective occurrence data reception module 234 configured to, among other things, receive objective occurrence data 70* from a user 20*, from one or more third party sources 50 (e.g., one or more third parties), or from one or more sensors 35.

The objective occurrence data reception module 234, in turn, may further include one or more sub-modules. For example, in some implementations, such as when the computing device 10 is a standalone device, the objective occurrence data reception module 234 may include a user interface data reception module 235 configured to receive objective occurrence data 70c via a user interface 122 (e.g., a keyboard, a mouse, a touchscreen, a microphone, an image capturing device such as a digital camera, and so forth). In some cases, the objective occurrence data 70c to be received via the user interface 122 may be provided, at least in part, by a user 20b. In some implementations, such as when the computing device 10 is a server, the objective occurrence data reception module 234 may include a network interface data reception module 236 configured to, among other things, receive objective occurrence data 70* from at least one of a wireless network or a wired network 40.

The objective occurrence data acquisition module 104 may include other sub-modules in various implementations. For example, in some implementations, the objective occurrence data acquisition module 104 may include a time data acquisition module 238 configured to acquire time and/or temporal elements associated with one or more objective occurrences. For these embodiments, the time and/or temporal elements (e.g., time stamps, time interval indicators, and/or temporal relationship indicators) acquired by the time data acquisition module 238 may be useful for, among other things, determining one or more sequential patterns.

In some implementations, the time data acquisition module 238 may include a time stamp acquisition module 240 configured to acquire (e.g., acquire either by receiving or by generating) one or more time stamps associated with one or more objective occurrences. In the same or different implementations, the time data acquisition module 238 may include a time interval acquisition module 241 configured to acquire (e.g., acquire either by receiving or by generating) one or more indicators of time intervals associated with one or more objective occurrences.

Figure 2D:
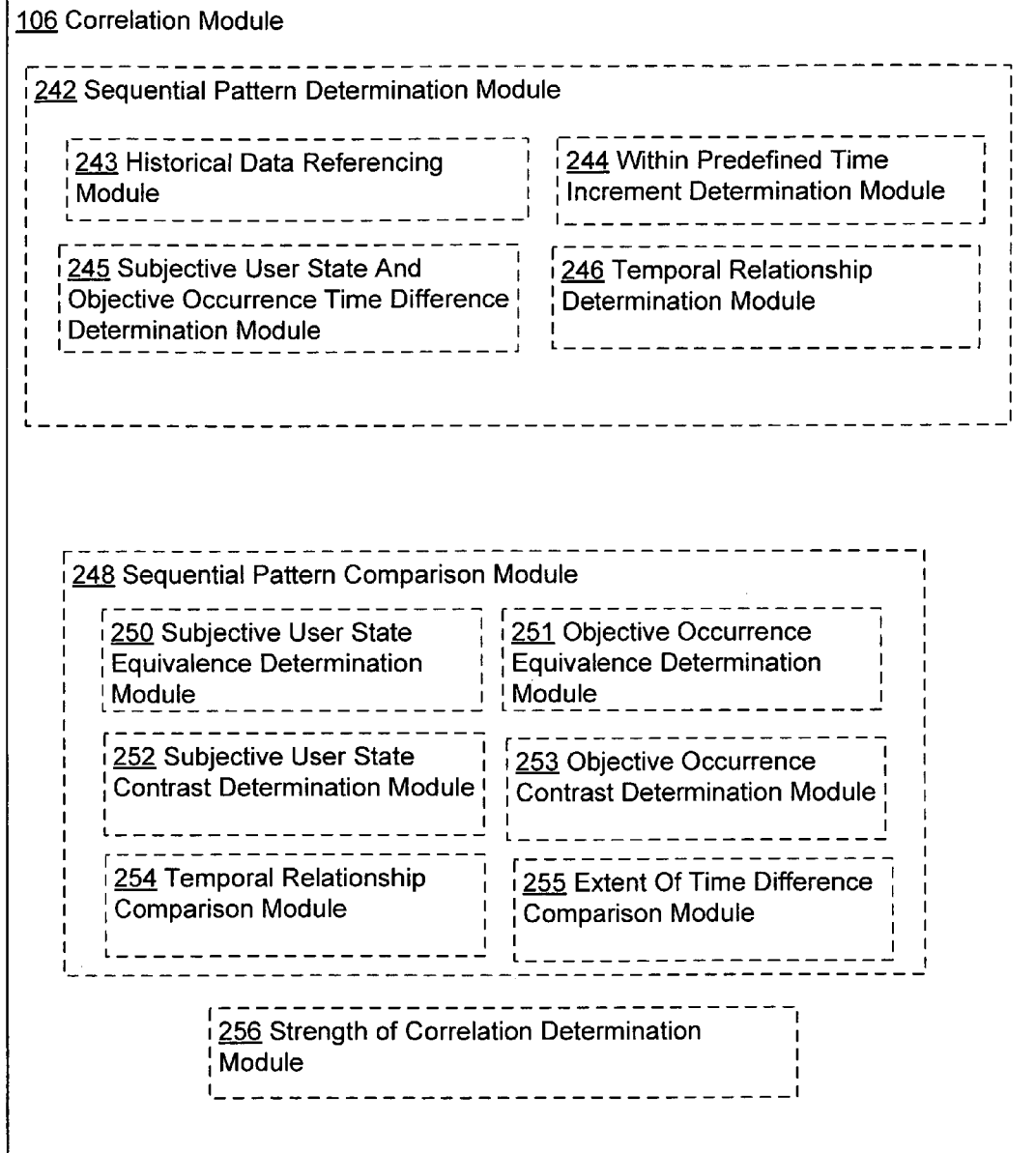
FIG. 2d shows another perspective of the correlation module 106 of the computing device 10 of FIG. 1b.

Turning now to FIG. 2d illustrating particular implementations of the correlation module 106 of the computing device 10 of FIG. 1b. The correlation module 106 may be configured to, among other things, correlate subjective user state data 60 with objective occurrence data 70* based, at least in part, on a determination of at least one sequential pattern of at least one objective occurrence and at least one subjective user state. In various embodiments, the correlation module 106 may include a sequential pattern determination module 242 configured to determine one or more sequential patterns of one or more incidences of subjective user states and one or more incidences of objective occurrences.

The sequential pattern determination module 242, in various implementations, may include one or more sub-modules that may facilitate in the determination of one or more sequential patterns. As depicted, the one or more sub-modules that may be included in the sequential pattern determination module 242 may include, for example, a "within predefined time increment determination" module 244, a temporal relationship determination module 246, a subjective user state and objective occurrence time difference determination module 245, and/or a historical data referencing module 243. In brief, the within predefined time increment determination module 244 may be configured to determine whether an incidence of at least one subjective user state associated with a user 20* occurred within a predefined time increment from an incidence of at least one objective occurrence. For example, determining whether a user 20* "feeling bad" (i.e., a subjective user state) occurred within ten hours (i.e., predefined time increment) of eating a large chocolate sundae (i.e., an objective occurrence). Such a process may be used in order to filter out events that are likely not related or to facilitate in determining the strength of correlation between subjective user state data 60 and objective occurrence data 70*. For example, if the user 20* "feeling bad" occurred more than 10 hours after eating the chocolate sundae, then this may indicate a weaker correlation between a subjective user state (e.g., feeling bad) and an objective occurrence (e.g., eating a chocolate sundae).

The temporal relationship determination module 246 of the sequential pattern determination module 242 may be configured to determine the temporal relationships between one or more incidences of subjective user states associated with a user 20* and one or more incidences of objective occurrences. For example, this determination may entail determining whether an incidence of a particular subjective user state (e.g., sore back) occurred before, after, or at least partially concurrently with an incidence of a particular objective occurrence (e.g., sub-freezing temperature).

The subjective user state and objective occurrence time difference determination module 245 of the sequential pattern determination module 242 may be configured to determine the extent of time difference between an incidence of at least one subjective user state associated with a user 20* and an incidence of at least one objective occurrence. For example, determining how long after taking a particular brand of medication (e.g., objective occurrence) did a user 20* feel "good" (e.g., subjective user state).

The historical data referencing module 243 of the sequential pattern determination module 242 may be configured to reference historical data 72 in order to facilitate in determining sequential patterns. For example, in various implementations, the historical data 72 that may be referenced may include, for example, general population trends (e.g., people having a tendency to have a hangover after drinking or ibuprofen being more effective than aspirin for toothaches in the general population), medical information such as genetic, metabolome, or proteome information related to the user 20* (e.g., genetic information of the user 20* indicating that the user 20* is susceptible to a particular subjective user state in response to occurrence of a particular objective occurrence), or historical sequential patterns such as known sequential patterns of the general population or of the user 20* (e.g., people tending to have difficulty sleeping within five hours after consumption of coffee). In some instances, such historical data 72 may be useful in associating one or more incidences of subjective user states associated with a user 20* with one or more incidences of objective occurrences.

In some embodiments, the correlation module 106 may include a sequential pattern comparison module 248. As will be further described herein, the sequential pattern comparison module 248 may be configured to compare two or more sequential patterns with each other to determine, for example, whether the sequential patterns at least substantially match each other or to determine whether the sequential patterns are contrasting sequential patterns.

As depicted in FIG. 2d, in various implementations, the sequential pattern comparison module 248 may further include one or more sub-modules that may be employed in order to, for example, facilitate in the comparison of different sequential patterns. For example, in various implementations, the sequential pattern comparison module 248 may include one or more of a subjective user state equivalence determination module 250, an objective occurrence equivalence determination module 251, a subjective user state contrast determination module 252, an objective occurrence contrast determination module 253, a temporal relationship comparison module 254, and/or an extent of time difference comparison module 255. In some implementations, the sequential pattern comparison module 248 may be employed in order to, for example, confirm the veracity of a hypothesis 71.

The subjective user state equivalence determination module 250 of the sequential pattern comparison module 248 may be configured to determine whether subjective user states associated with different sequential patterns are at least substantially equivalent. For example, the subjective user state equivalence determination module 250 may determine whether a first subjective user state of a first sequential pattern is equivalent to a second subjective user state of a second sequential pattern. For instance, suppose a user 20* reports that on Monday he had a stomach ache (e.g., first subjective user state) after eating at a particular restaurant (e.g., a first objective occurrence), and suppose further that the user 20* again reports having a stomach ache (e.g., a second subjective user state) after eating at the same restaurant (e.g., a second objective occurrence) on Tuesday, then the subjective user state equivalence determination module 250 may be employed in order to compare the first subjective user state (e.g., stomach ache) with the second subjective user state (e.g., stomach ache) to determine whether they are equivalent. Note that in this example, the first sequential pattern may represent a hypothesis 71 linking a subjective user state (e.g., stomach ache) to an objective occurrence (e.g., eating at a particular restaurant).

In contrast, the objective occurrence equivalence determination module 251 of the sequential pattern comparison module 248 may be configured to determine whether objective occurrences of different sequential patterns are at least substantially equivalent. For example, the objective occurrence equivalence determination module 251 may determine whether a first objective occurrence of a first sequential pattern is equivalent to a second objective occurrence of a second sequential pattern. For instance, in the above example, the objective occurrence equivalence determination module 251 may compare eating at the particular restaurant on Monday (e.g., first objective occurrence) with eating at the same restaurant on Tuesday (e.g., second objective occurrence) in order to determine whether the first objective occurrence is equivalent to the second objective occurrence.

In some implementations, the sequential pattern comparison module 248 may include a subjective user state contrast determination module 252 that may be configured to determine whether subjective user states associated with different sequential patterns are contrasting subjective user states. For example, the subjective user state contrast determination module 252 may determine whether a first subjective user state of a first sequential pattern is a contrasting subjective user state from a second subjective user state of a second sequential pattern. To illustrate, suppose a user 20* reports that he felt very "good" (e.g., first subjective user state) after jogging for an hour (e.g., first objective occurrence) on Monday, but reports that he felt "bad" (e.g., second subjective user state) when he did not exercise (e.g., second objective occurrence) on Tuesday, then the subjective user state contrast determination module 245 may compare the first subjective user state (e.g., feeling good) with the second subjective user state (e.g., feeling bad) to determine that they are contrasting subjective user states.

In some implementations, the sequential pattern comparison module 248 may include an objective occurrence contrast determination module 253 that may be configured to determine whether objective occurrences of different sequential patterns are contrasting objective occurrences. For example, the objective occurrence contrast determination module 253 may determine whether a first objective occurrence of a first sequential pattern is a contrasting objective occurrence from a second objective occurrence of a second sequential pattern. For instance, in the previous example, the objective occurrence contrast determination module 253 may compare the "jogging" on Monday (e.g., first objective occurrence) with the "no jogging" on Tuesday (e.g., second objective occurrence) in order to determine whether the first objective occurrence is a contrasting objective occurrence from the second objective occurrence. Based on the contrast determination, an inference may be made that the user 20* may feel better by jogging rather than by not jogging at all.

In some embodiments, the sequential pattern comparison module 248 may include a temporal relationship comparison module 254 that may be configured to make comparisons between different temporal relationships of different sequential patterns. For example, the temporal relationship comparison module 254 may compare a first temporal relationship between a first subjective user state and a first objective occurrence of a first sequential pattern with a second temporal relationship between a second subjective user state and a second objective occurrence of a second sequential pattern in order to determine whether the first temporal relationship at least substantially matches the second temporal relationship.

For example, referring back to the earlier example, suppose the user 20* eating at the particular restaurant (e.g., first objective occurrence) and the subsequent stomach ache (e.g., first subjective user state) on Monday represents a first sequential pattern while the user 20* eating at the same restaurant (e.g., second objective occurrence) and the subsequent stomach ache (e.g., second subjective user state) on Tuesday represents a second sequential pattern. In this example, the occurrence of the stomach ache after (rather than before or concurrently) eating at the particular restaurant on Monday represents a first temporal relationship associated with the first sequential pattern while the occurrence of a second stomach ache after (rather than before or concurrently) eating at the same restaurant on Tuesday represents a second temporal relationship associated with the second sequential pattern. Under such circumstances, the temporal relationship comparison module 254 may compare the first temporal relationship to the second temporal relationship in order to determine whether the first temporal relationship and the second temporal relationship at least substantially match (e.g., stomach aches in both temporal relationships occurring after eating at the restaurant). Such a match may result in the inference that a stomach ache is associated with eating at the particular restaurant and may, in some instances, confirm the veracity of a hypothesis 71.

In some implementations, the sequential pattern comparison module 248 may include an extent of time difference comparison module 255 that may be configured to compare the extent of time differences between incidences of subjective user states and incidences of objective occurrences of different sequential patterns. For example, the extent of time difference comparison module 255 may compare the extent of time difference between incidence of a first subjective user state and incidence of a first objective occurrence of a first sequential pattern with the extent of time difference between incidence of a second subjective user state and incidence of a second objective occurrence of a second sequential pattern. In some implementations, the comparisons may be made in order to determine that the extent of time differences of the different sequential patterns at least substantially or proximately match.

In some embodiments, the correlation module 106 may include a strength of correlation determination module 256 for determining a strength of correlation between subjective user state data 60 and objective occurrence data 70* associated with a user 20*. In some implementations, the strength of correlation may be determined based, at least in part, on the results provided by the other sub-modules of the correlation module 106 (e.g., the sequential pattern determination module 242, the sequential pattern comparison module 248, and their sub-modules).

Figure 2E:
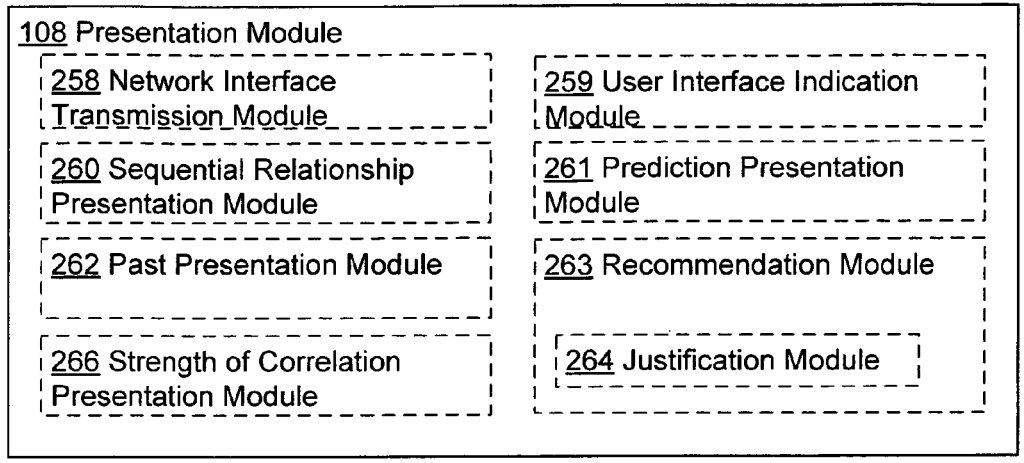
FIG. 2e shows another perspective of the presentation module 108 of the computing device 10 of FIG. 1b.

FIG. 2e illustrates particular implementations of the presentation module 108 of the computing device 10 of FIG. 1b. In various implementations, the presentation module 108 may be configured to present, for example, one or more results of the correlation operations performed by the correlation module 106. In some implementations, the presentation module 108 may include a network interface transmission module 258 configured to transmit one or more results of a correlation operation performed by the correlation module 106 via a network interface 120 (e.g., NIC). In the same or different implementations, the presentation module 108 may include a user interface indication module 259 configured to indicate one or more results of a correlation operation performed by the correlation module 106 via a user interface 122 (e.g., display monitor or audio system including a speaker).

The one or more results of a correlation operation performed by the correlation module 106 may be presented in different forms in various alternative embodiments. For example, in some implementations, the presentation of the one or more results may entail the presentation module 108 presenting to the user 20* (or some other third party) an indication of a sequential relationship between a subjective user state and an objective occurrence associated with the user 20* (e.g., "whenever you eat a banana, you have a stomach ache"). In alternative implementations, other ways of presenting the results of the correlation may be employed. For example, in various alternative implementations, a notification may be provided to notify past tendencies or patterns associated with a user 20*. In some implementations, a notification of a possible future outcome may be provided. In other implementations, a recommendation for a future course of action based on past patterns may be provided. These and other ways of presenting the correlation results will be described in the processes and operations to be described herein.

In order to present the one or more results of a correlation operation performed by the correlation module 106, the presentation module 108 may include one or more sub-modules. For example, in some implementations, the presentation module 108 may include a sequential relationship presentation module 260 configured to present an indication of a sequential relationship between at least one subjective user state of a user 20* and at least one objective occurrence. In the same or different implementations, the presentation module 108 may include a prediction presentation module 261 configured to present a prediction of a future subjective user state of a user 20* resulting from a future objective occurrence associated with the user 20*. In the same or different implementations, the prediction presentation module 261 may also be designed to present a prediction of a future subjective user state of a user 20* resulting from a past objective occurrence associated with the user 20*. In some implementations, the presentation module 108 may include a past presentation module 262 that is designed to present a past subjective user state of a user 20* in connection with a past objective occurrence associated with the user 20*.

In some implementations, the presentation module 108 may include a recommendation module 263 configured to present a recommendation for a future action based, at least in part, on the results of a correlation of subjective user state data 60 with objective occurrence data 70* as performed by the correlation module 106. In certain implementations, the recommendation module 262 may further include a justification module 264 for presenting a justification for the recommendation presented by the recommendation module 263. In some implementations, the presentation module 108 may include a strength of correlation presentation module 266 for presenting an indication of a strength of correlation between subjective user state data 60 and objective occurrence data 70*.

In various embodiments, the computing device 10 of FIG. 1b may include a network interface 120 that may facilitate in communicating with a user 20a, with one or more sensors 35, and/or with one or more third party sources 50. For example, in embodiments where the computing device 10 is a server, the computing device 10 may include a network interface 120 that may be configured to receive from the user 20a subjective user state data 60. In some embodiments, objective occurrence data 70a, 70b, and/or 70c may also be received through the network interface 120. Examples of a network interface 120 includes, for example, a network interface card (NIC).

The computing device 10 may also include a memory 140 for storing various data. For example, in some embodiments, memory 140 may be employed in order to store a hypothesis 71 and/or historical data 72. In some implementations, the historical data 72 may include historical subjective user state data of a user 20* that may indicate one or more past subjective user states of the user 20* and historical objective occurrence data that may indicate one or more past objective occurrences. In the same or different implementations, the historical data 72 may include historical medical data of a user 20* (e.g., genetic, metoblome, proteome information), population trends, historical sequential patterns derived from general population, and so forth.

In various embodiments, the computing device 10 may include a user interface 122 to communicate directly with a user 20b. For example, in embodiments in which the computing device 10 is a standalone device such as a handheld device (e.g., cellular telephone, PDA, and so forth), the user interface 122 may be configured to directly receive from the user 20b subjective user state data 60 and/or objective occurrence data 70*. In some implementations, the user interface 122 may also be designed to visually or audioally present the results of correlating subjective user state data 60 and objective occurrence data 70*. The user interface 122 may include, for example, one or more of a display monitor, a touch screen, a key board, a key pad, a mouse, an audio system including a microphone and/or one or more speakers, an imaging system including a digital or video camera, and/or other user interface devices.

Figure 2F:
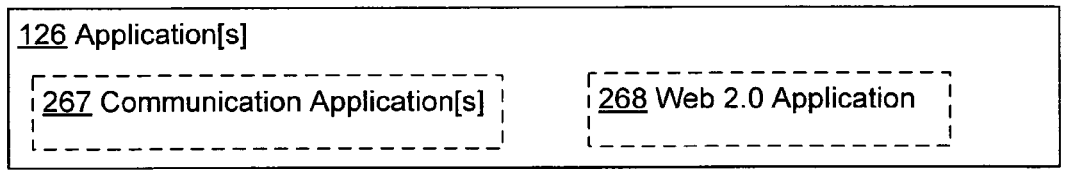
FIG. 2f shows another perspective of the one or more applications 126 of the computing device 10 of FIG. 1b.

FIG. 2f illustrates particular implementations of the one or more applications 126 of FIG. 1b. For these implementations, the one or more applications 126 may include, for example, one or more communication applications 267 such as a text messaging application and/or an audio messaging application including a voice recognition system application. In some implementations, the one or more applications 126 may include a web 2.0 application 268 to facilitate communication via, for example, the World Wide Web.

The various features and characteristics of the components, modules, and sub-modules of the computing device 10 presented thus far will be described in greater detail with respect to the processes and operations to be described herein. Note that the subjective user state data 60 may be in a variety of forms including, for example, text messages (e.g., blog entries, microblog entries, instant messages, text email messages, and so forth), audio messages, and/or images (e.g., an image capturing user's facial expression or gestures).

Figure 2G:
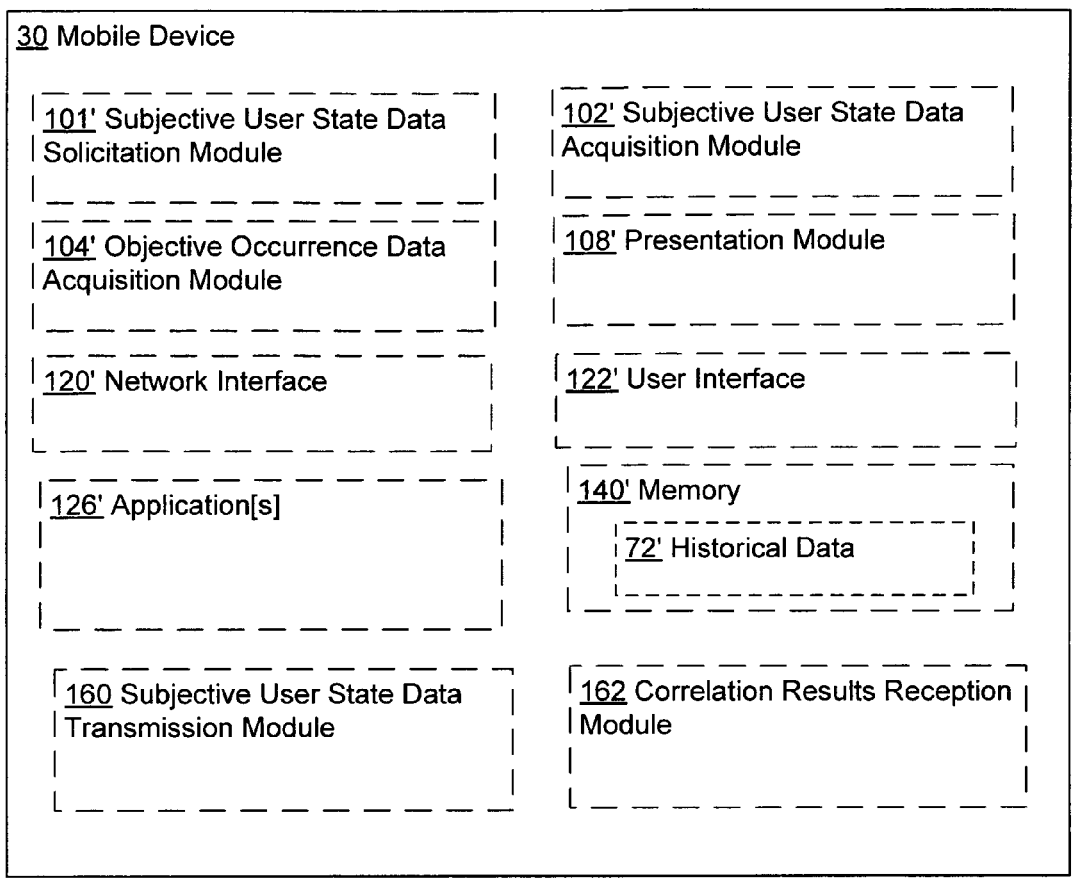
FIG. 2g shows another perspective of the mobile device 30 of FIG. 1b.

Referring to FIG. 2g illustrating particular implementations of the mobile device 30 of FIG. 1a. The mobile device 30 includes some modules that are the same as some of the modules that may be included in the computing device 10. These components may have the same features and perform the same or similar types of functions as those of their corresponding counterparts in the computing device 10. For example, and just like the computing device 10, the mobile device 30 may include a subjective user state data solicitation module 101', a subjective user state data acquisition module 102', an objective occurrence data acquisition module 104', a presentation module 108', a network interface 120', a user interface 122', one or more applications[s] 126' (e.g., including a Web 2.0 application), and/or memory 140' (including historical data 72').

In various implementations, in addition to these components, the mobile device 30 may include a subjective user state data transmission module 160 that is configured to transmit (e.g., transmit via a wireless and/or wired network 40) subjective user state data 60 including data indicating incidence of at least one subjective user state 60a. In some implementations, the subjective user state data 60 may be transmitted to a network server such as computing device 10. In the same or different implementations, the mobile device 30 may include a correlation results reception module 162 that may be configured to receive, via a wireless and/or wired network 40, results of correlation of subjective user state data 60 with objective occurrence data 70*. In some implementations, such a correlation may have been performed at a network server (e.g., computing device 10).

Figure 2H:
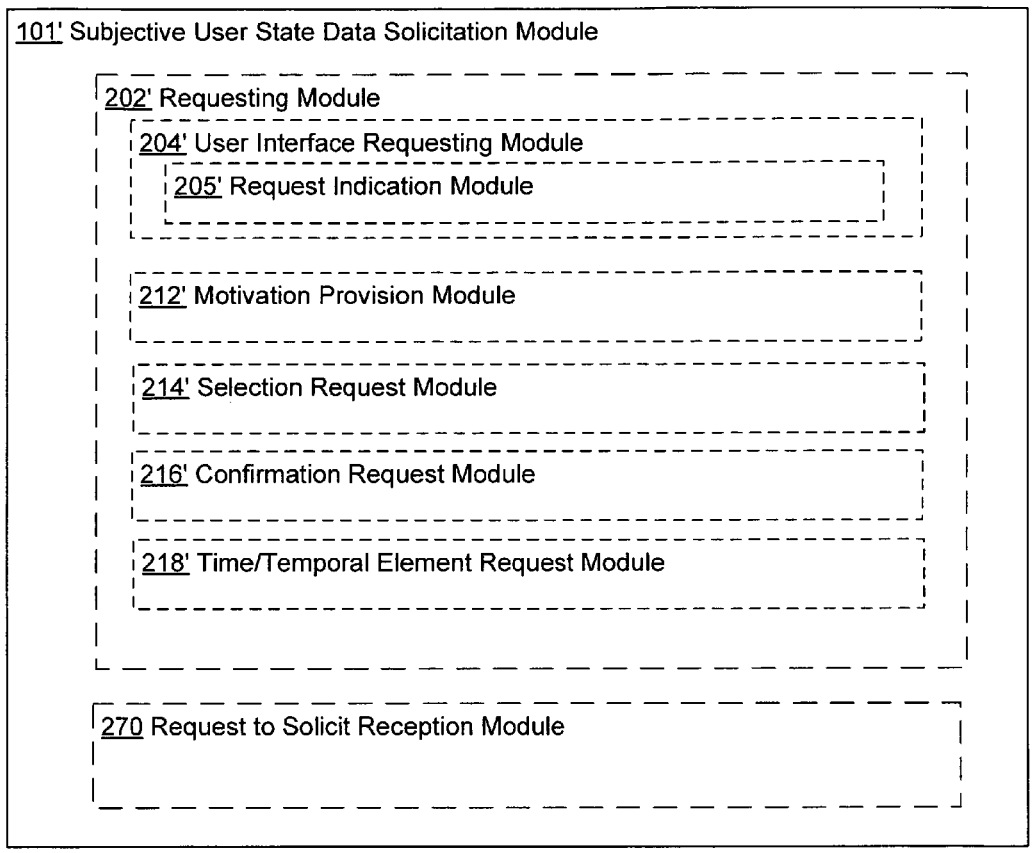
FIG. 2h shows another perspective of the subjective user state data solicitation module 101' of the mobile device 30 of FIG. 2g.

FIG. 2h illustrates particular implementations of the subjective user state data solicitation module 101' of the mobile device 30 of FIG. 2g. As depicted, the subjective user state data solicitation module 101' may include some components that are the same or similar to some of the components that may be included in the subjective user state data solicitation module 101 of the computing device 10. For example, the subjective user state data solicitation module 101' may include a requesting module 202' that further includes a user interface requesting module 204' (and a request indication module 205' included with the user interface requesting module 204'), a motivation provision module 212', a selection request module 214', a confirmation request module 216' and a time/temporal element request module 218'. These components may have the same features and perform the same functions as their counterparts in the computing device 10.

In addition, the subjective user state data solicitation module 101' may include a request to solicit reception module 270 that may be configured to receive a request to solicit data indicating incidence of at least one subjective user state 60a associated with a user 20a. Such a request, in some implementations, may be remotely generated (e.g. remotely generated at the computing device 10) based, at least in part, on a hypothesis 71 and, in some cases, in response, at least in part, to an incidence of at least one objective occurrence.

Figure 2I:
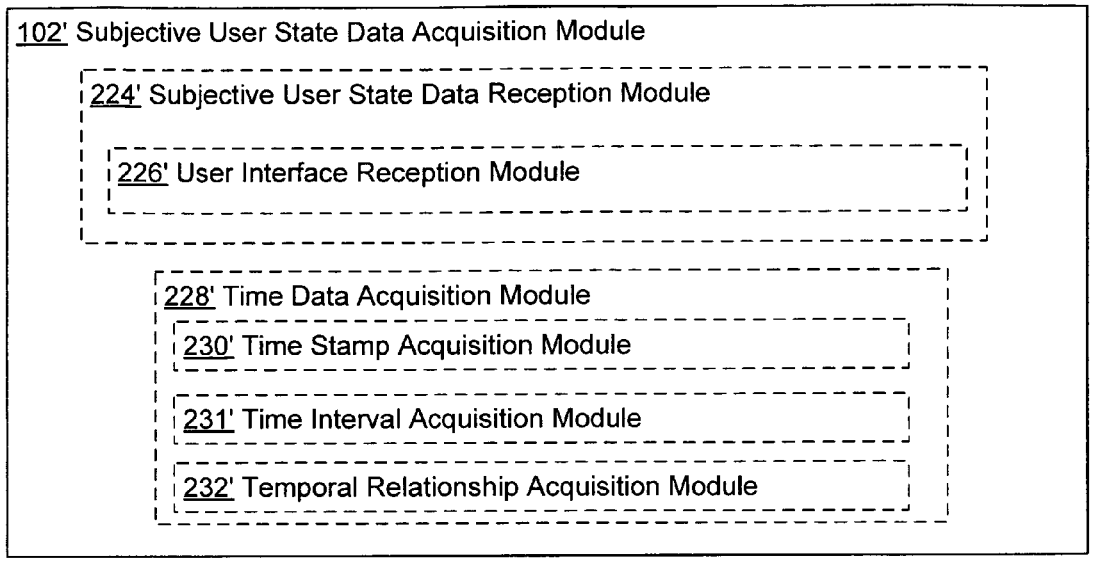
FIG. 2i shows another perspective of the subjective user state data acquisition module 102' of the mobile device 30 of FIG. 2g.

FIG. 2i illustrates particular implementations of the subjective user state data acquisition module 102' of the mobile device 30 of FIG. 2g. The subjective user state data acquisition module 102' may include some components that are the same or similar to some of the components that may be included in the subjective user state data acquisition module 102 (see FIG. 2b) of the computing device 10. These components may perform the same or similar functions as their counterparts in the subjective user state data acquisition module 102 of the computing device 10. For example, the subjective user state data acquisition module 102' may include a subjective user state data reception module 224' and a time data acquisition module 228'. Similar to their counterparts in the computing device 10 and performing similar roles, the subjective user state data reception module 224' may include a user interface reception module 226' while the time data acquisition module 228' may include a time stamp acquisition module 230', a time interval acquisition module 231', and/or a temporal relationship acquisition module 232'.

Figure 2J:
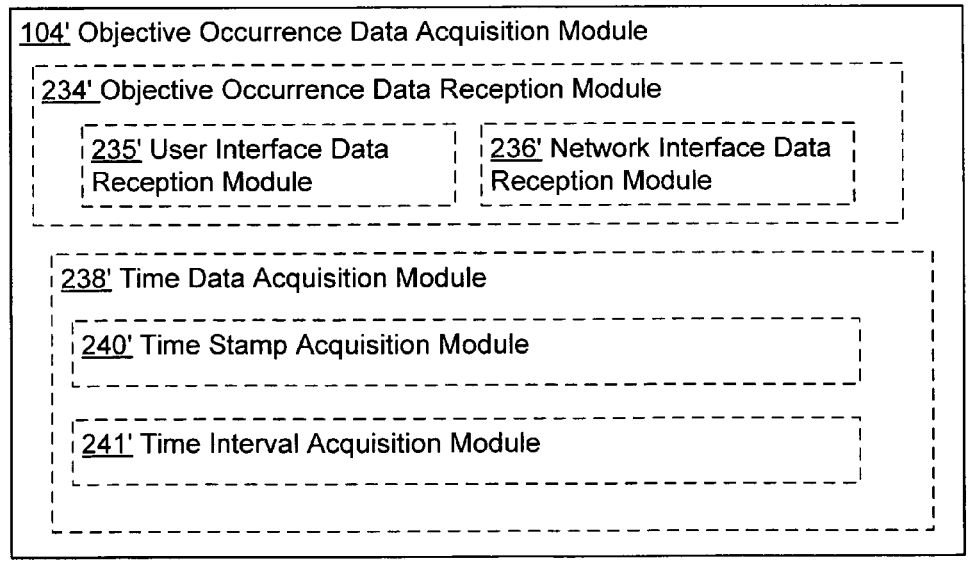
FIG. 2j shows another perspective of the objective occurrence data acquisition module 104' of the mobile device 30 of FIG. 2g.

Referring to FIG. 2j illustrating particular implementations of the objective occurrence data acquisition module 104' of the mobile device 30 of FIG. 2g. The objective occurrence data acquisition module 104' may include the same or similar type of components that may be included in the objective occurrence data acquisition module 104 (see FIG. 2c) of the computing device 10. For example, the objective occurrence data acquisition module 104' may include an objective occurrence data reception module 234' (which may further include a user interface data reception module 235' and/or a network interface data reception 236') and a time data acquisition module 238' (which may further include a time stamp acquisition module 240' and/or a time interval acquisition module 241').

Figure 2K:
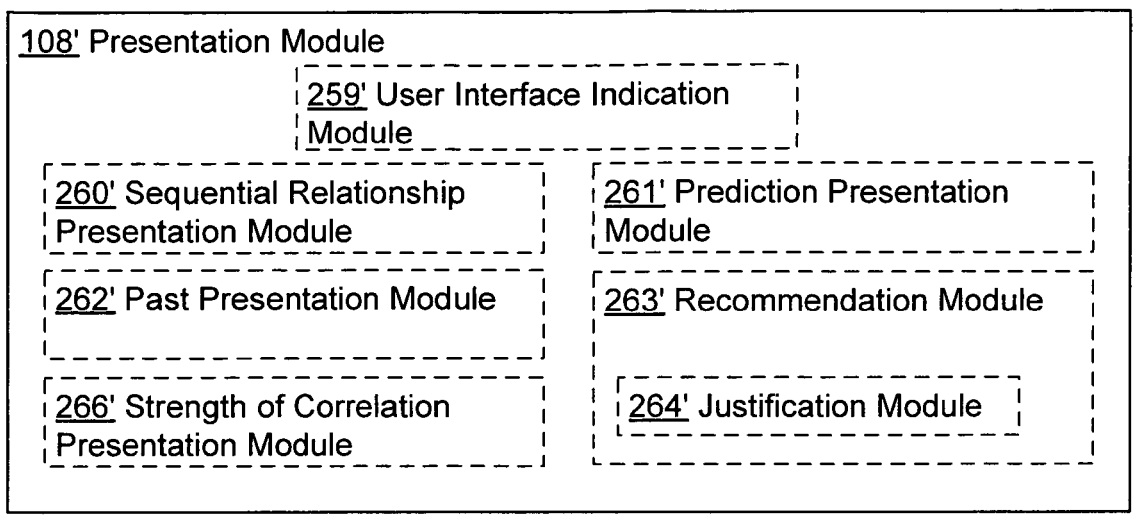
FIG. 2k shows another perspective of the presentation module 108' of the mobile device 30 of FIG. 2g.

FIG. 2k illustrates particular implementations of the presentation module 108' of the mobile device 30 of FIG. 2g. In various implementations, the presentation module 108' may include some of the same components that may be included in the presentation module 108 (see FIG. 2e) of the computing device 10. For example, the presentation module 108' may include a user interface indication module 259', a sequential relationship presentation module 260', a prediction presentation module 261', a past presentation module 262', a recommendation module 263' (which may further include a justification module 264'), and/or a strength of correlation presentation module 266'.

A more detailed discussion of these components (e.g., modules and interfaces) that may be included in the mobile device 30 and those that may be included in the computing device 10 will be provided with respect to the processes and operations to be described herein.

Figure 3:
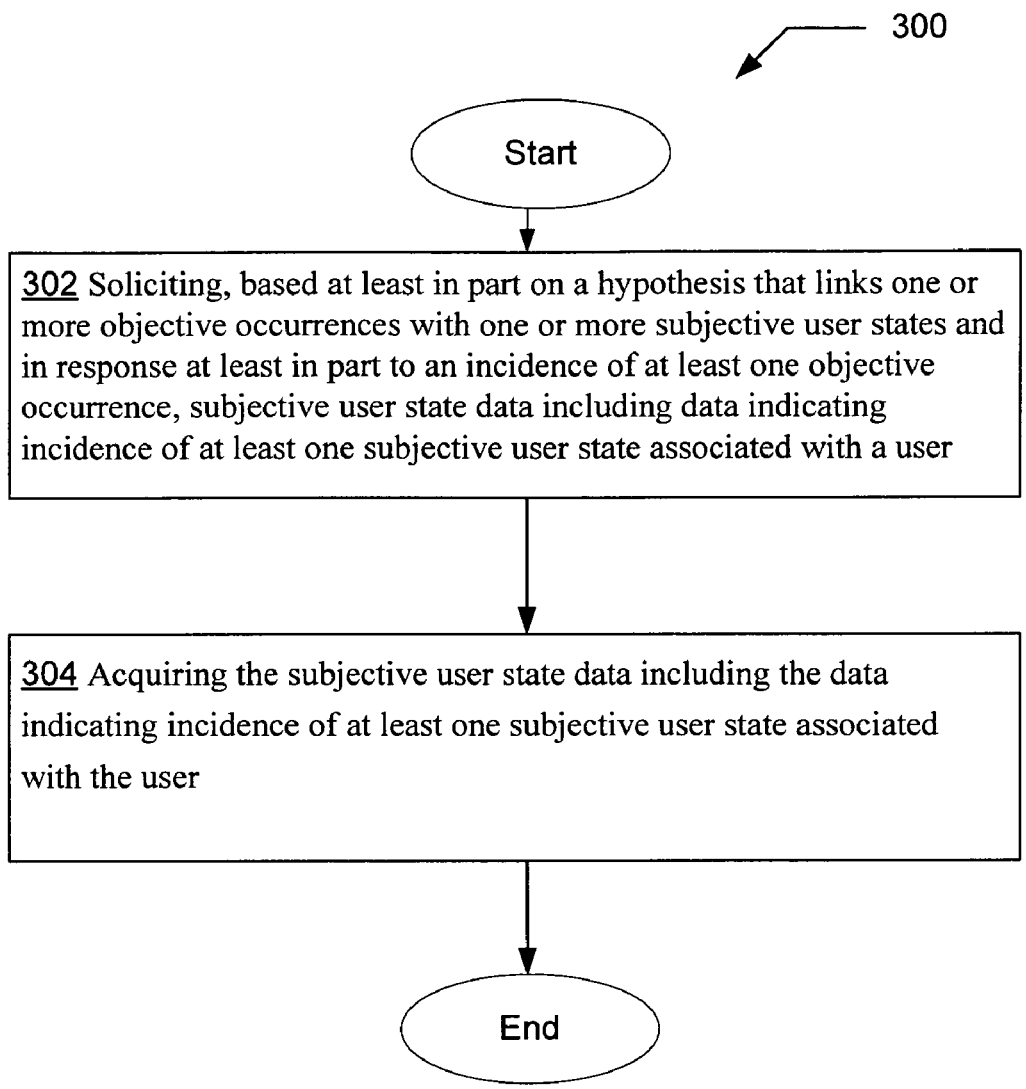
FIG. 3 is a high-level logic flowchart of a process.

FIG. 3 illustrates an operational flow 300 representing example operations related to, among other things, hypothesis based solicitation and acquisition of subjective user state data 60 including at least data indicating incidence of at least one subjective user state 60a associated with a user 20*. In some embodiments, the operational flow 300 may be executed by, for example, the computing device 10, which may be a server or a standalone device. Alternatively, the operation flow may be executed by the mobile device 30 of FIG. 1b.

In FIG. 3 and in the following figures that include various examples of operational flows, discussions and explanations may be provided with respect to the above-described exemplary environment of FIGS. 1a and 1b, and/or with respect to other examples (e.g., as provided in FIGS. 2a-2k) and contexts. However, it should be understood that the operational flows may be executed in a number of other environments and contexts, and/or in modified versions of FIGS. 1a, 1b, and 2a-2k. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a subjective user state data solicitation operation 302 for soliciting, based at least in part on a hypothesis that links one or more objective occurrences with one or more subjective user states and in response at least in part to an incidence of at least one objective occurrence, subjective user state data including data indicating incidence of at least one subjective user state associated with a user. For instance, the subjective user state data solicitation module 101 of the computing device 10 or the subjective user state data solicitation module 101' of the mobile device 30 soliciting, based at least in part on a hypothesis 71 (e.g., the computing device 10 referencing a hypothesis 71, or the mobile device 30 receiving a request for soliciting from the computing device 10, the request being remotely generated and sent to the mobile device 30 based at least in part on a hypothesis 71) that links one or more objective occurrences with one or more subjective user states (e.g., a group of users 20* ingesting a particular type of medicine such as aspirin, and the subsequent subjective physical states, such as pain relief, associated with the group of users 20*) and in response at least in part to an incidence of at least one objective occurrence (e.g., ingestion of a medicine by a user 20*), subjective user state data 60 including data indicating incidence of at least one subjective user state 60a (e.g., pain relief by user 20*) associated with a user 20*.

Note that the solicitation of the subjective user state data 60, as described above, may or may not be in reference to solicitation of particular data that indicates occurrence of a particular or particular type of subjective user state. That is, in some embodiments, the solicitation of the subjective user state data 60 may be in reference to solicitation for subjective user state data 60 including data indicating incidence of any subjective user state with respect to, for example, a particular point in time or time interval. While in other embodiments, the solicitation of the subjective user state data 60 may involve solicitation for subjective user state data including solicitation of particular data indicating occurrence of a particular or particular type of subjective user state.

The term "soliciting" as described above may be in reference to direct or indirect solicitation of (e.g., requesting to be provided with, requesting to access, gathering of, or other methods of being provided with, or being allowed access) subjective user state data 60 from one or more sources. The sources for the subjective user state data 60 may be a user 20*, a mobile device 30, or one or more network servers (not depicted), which may have already been provided with such subjective user state data 60. For example, if the computing device 10 is a server, then the computing device 10 may indirectly solicit the objective occurrence data 70* from a user 20a by transmitting the solicitation (e.g., a request or inquiry) to the mobile device 30, which may then actually solicit the subjective user state data 60 from the user 20a. Alternatively, such subjective user state data 60 may have already been provided to the mobile device 30, in which case the mobile device 30 merely provides for or allows access to such data.

In still other alternative implementations, such subjective user state data 60 may have been previously stored in a network server (not depicted), and such a network server may be solicited for the subjective user state data 60. In yet other implementations in which the computing device 10 is a standalone device, such as a handheld device to be used directly by a user 20b, the computing device 10 may directly solicit the subjective user state data 60 from the user 20b.

Operational flow 300 may further include a subjective user state data acquisition operation 304 for acquiring the subjective user state data including the data indicating incidence of at least one subjective user state associated with the user. For instance, the subjective user state data acquisition module 102 of the computing device 10 or the subjective user state data acquisition module 102' of the mobile device 30 acquiring (e.g., receiving by the computing device 10 or by the mobile device 30 from a user 20*) the subjective user state data 60.

Figure 4A:
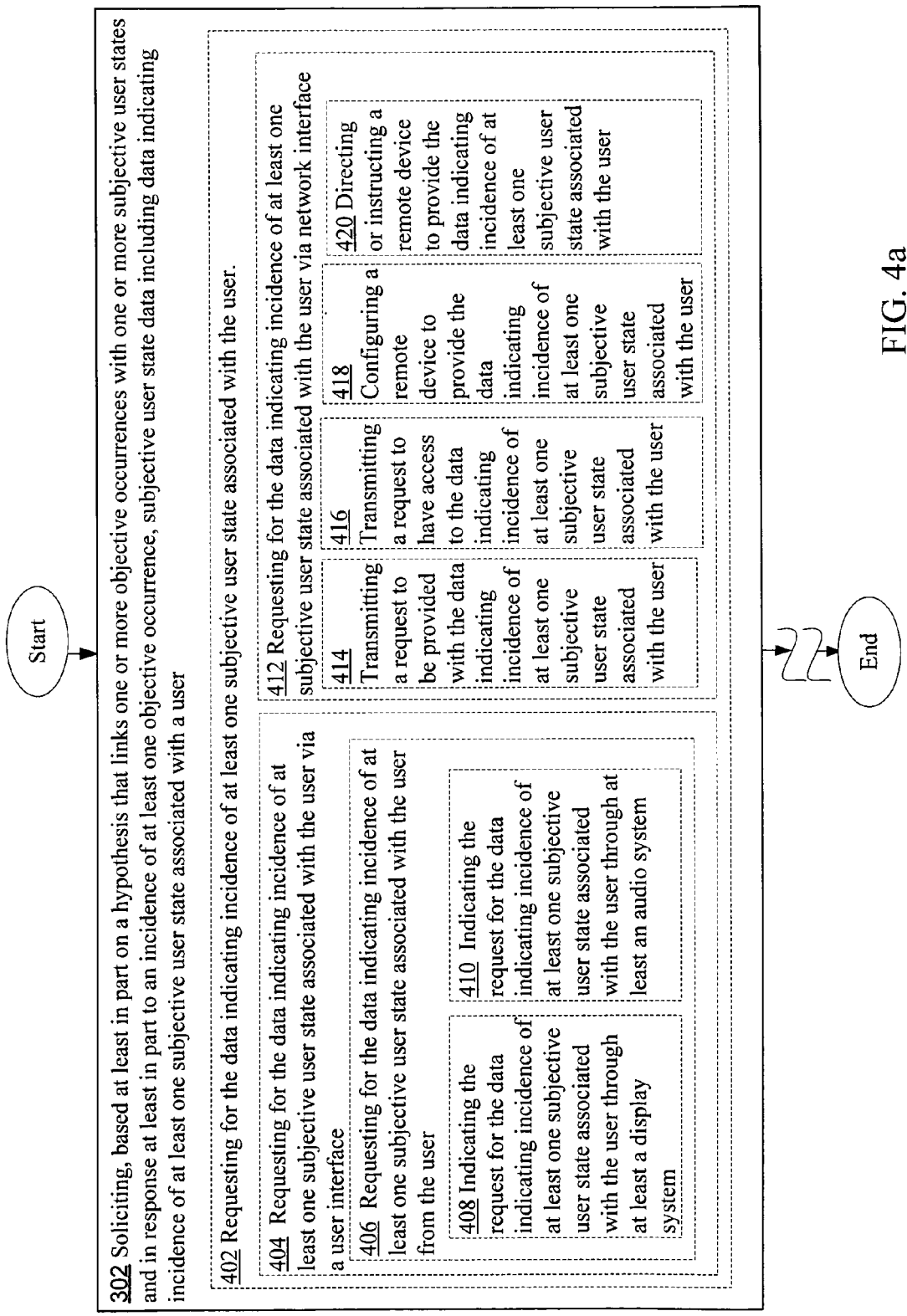
FIG. 4a is a high-level logic flowchart of a process depicting alternate implementations of the subjective user state data solicitation operation 302 of FIG. 3.

In various implementations, the subjective user state data solicitation operation 302 of FIG. 3 may include one or more additional operations as illustrated in FIGS. 4a, 4b, 4c, 4d, 4e, 4f, and 4g. For example, in some implementations the subjective user state data solicitation operation 302 may include a requesting operation 402 for requesting for the data indicating incidence of at least one subjective user state associated with the user as depicted in FIG. 4a. For instance, the requesting module 202* of the computing device 10 or the mobile device 30 requesting (e.g., transmitting or indicating a request by the computing device 10 or by the mobile device 30) for the data indicating incidence of at least one subjective user state 60a associated with the user 20*.

In various implementations, the requesting operation 402 may further include one or more additional operations. For example, in some implementations, the requesting operation 402 may include an operation 404 for requesting for the data indicating incidence of at least one subjective user state associated with the user via a user interface as depicted in FIG. 4a. For example, the user interface requesting module 204* of the computing device 10 (e.g., when the computing device 10 is a standalone device) or the mobile device 30 requesting for the data indicating incidence of at least one subjective user state 60a associated with the user 20* via a user interface 122* (e.g. an audio system including one or more speakers or a display system including a display monitor or a touchscreen).

Operation 404, in turn, may further include an operation 406 for requesting for the data indicating incidence of at least one subjective user state associated with the user from the user as depicted in FIG. 4a. For instance, the user interface requesting module 204* of the computing device 10 or the mobile device 30 requesting for the data indicating incidence of at least one subjective user state 60a associated with the user 20* from the user 20*.

In some implementations, operation 406 may include an operation 408 for indicating the request for the data indicating incidence of at least one subjective user state associated with the user through at least a display system as depicted in FIG. 4a. For instance, the request indication module 205* of the computing device 10 or the mobile device 30 indicating the request for the data indicating incidence of at least one subjective user state 60a associated with the user 20* (e.g., asking the user 20*, "how did you feel this morning?") through at least a display system (e.g., a display system including a display monitor or a touchscreen).

In some implementations, operation 406 may include an operation 410 for indicating the request for the data indicating incidence of at least one subjective user state associated with the user through at least an audio system as depicted in FIG. 4a. For instance, the request indication module 205* of the computing device 10 or the mobile device 30 indicating the request for the data indicating incidence of at least one subjective user state 60a associated with the user 20* (e.g., asking the user 20* "did your pain go away this morning?")

through at least an audio system (e.g., an audio system including at least one audio speaker).

In various implementations, the reception operation 402 may include an operation 412 for requesting for the data indicating incidence of at least one subjective user state associated with the user via network interface as depicted in FIG. 4a. For instance, the network interface requesting module 206 of the computing device 10 (e.g., when the computing device 10 is a server) requesting for the data indicating incidence of at least one subjective user state 60a associated with the user 20a via network interface 120 (e.g., NIC).

In some implementations, operation 412 may include an operation 414 for transmitting a request to be provided with the data indicating incidence of at least one subjective user state associated with the user as depicted in FIG. 4a. For instance, the request transmission module 207 of the computing device 10 (e.g., when the computing device 10 is a server) transmitting a request to be provided with the data indicating incidence of at least one subjective user state 60a associated with the user 20a.

In some implementations, operation 412 may include an operation 416 for transmitting a request to have access to the data indicating incidence of at least one subjective user state associated with the user as depicted in FIG. 4a. For instance, the request access module 208 of the computing device 10 transmitting a request (e.g., transmitting a request to the mobile device 30, to one or more third parties, or to one or more network servers) to have access to the data indicating incidence of at least one subjective user state 60a associated with the user 20a.

In some implementations, operation 412 may include an operation 418 for configuring a remote device to provide the data indicating incidence of at least one subjective user state associated with the user as depicted in FIG. 4a. For instance, the configuration module 209 configuring a remote device (e.g., a remote network server, the mobile device 30, or some other network device) to provide the data indicating incidence of at least one subjective user state 60a associated with the user 20a.

In some implementations, operation 412 may include an operation 420 for directing or instructing a remote device to provide the data indicating incidence of at least one subjective user state associated with the user as depicted in FIG. 4a. For instance, the directing/instructing module 210 directing or instructing a remote device (e.g., transmitting directions or instructions to the remote device such as a remote network server or the mobile device 30) to provide the data indicating incidence of at least one subjective user state 60a associated with the user 20a.

Figure 4B:
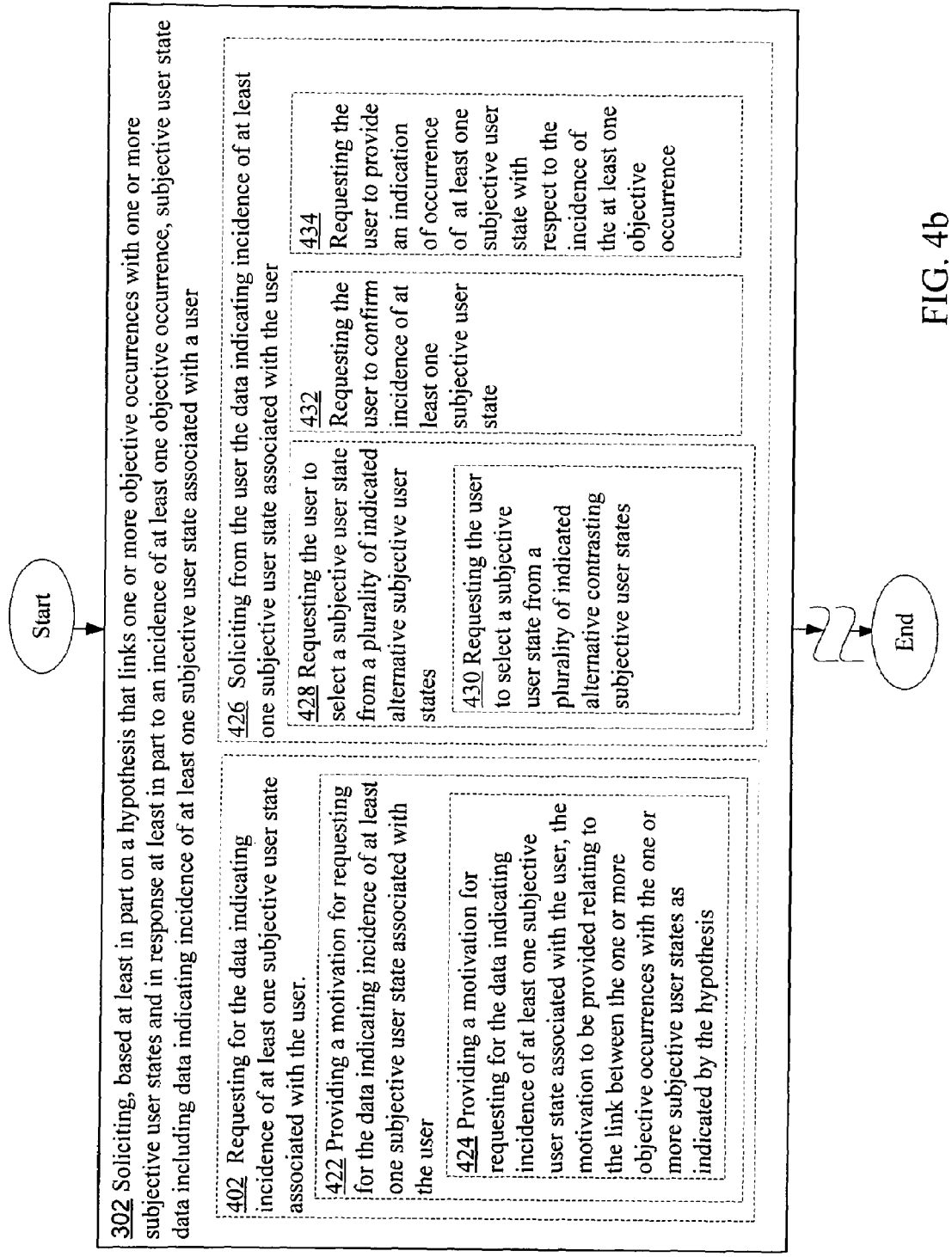
FIG. 4b is a high-level logic flowchart of a process depicting alternate implementations of the subjective user state data solicitation operation 302 of FIG. 3.

In various implementations, the reception operation 402 may include an operation 422 for providing a motivation for requesting for the data indicating incidence of at least one subjective user state associated with the user as depicted in FIG. 4b. For instance, the motivation provision module 212* of the computing device 10 or the mobile device 30 providing a motivation for requesting for the data indicating incidence of at least one subjective user state 60a associated with the user 20*. For example, asking and indicating to the user 20* "Are you happy? I think it might be the weather."

In some implementations, operation 422 may further include an operation 424 for providing a motivation for requesting for the data indicating incidence of at least one subjective user state associated with the user, the motivation to be provided relating to the link between the one or more objective occurrences with the one or more subjective user states as indicated by the hypothesis as depicted in FIG. 4b. For instance, the motivation provision module 212* of the computing device 10 or the mobile device 30 providing a motivation for requesting for the data indicating incidence of at least one subjective user state 60a associated with the user 20*, the motivation to be provided relating to the link between the one or more objective occurrences (e.g., weather conditions) with the one or more subjective user states (e.g., subjective mental state such as happiness or depression) as indicated by the hypothesis 71.

In some implementations, the solicitation operation 302 of FIG. 3 may include an operation 426 for soliciting from the user the data indicating incidence of at least one subjective user state associated with the user as depicted in FIG. 4b. For instance, the subjective user state data solicitation module 101* of the computing device 10 or the mobile device 30 soliciting from the user 20* the data indicating incidence of at least one subjective user state 60a associated with the user 20*.

Operation 426, in turn, may include one or more additional operations in various implementations. For example, in some implementations, operation 426 may include an operation 428 for requesting the user to select a subjective user state from a plurality of indicated alternative subjective user states as depicted in FIG. 4b. For instance, the selection request module 214* of the computing device 10 or the mobile device 30 requesting the user 20* to select a subjective user state from a plurality of indicated alternative subjective user states (e.g., asking the user 20* through a user interface 122* to select from alternate choices of "happy," "sad," "in pain," and "upset stomach").

In some implementations, operation 428 may further include an operation 430 for requesting the user to select a subjective user state from a plurality of indicated alternative contrasting subjective user states as depicted in FIG. 4b. For instance, the selection request module 214* of the computing device 10 or the mobile device 30 requesting the user 20* to select a subjective user state from a plurality of indicated alternative contrasting subjective user states (e.g., asking the user 20* through a user interface 122* to select from alternative choices of "very happy," "moderately happy," "slightly sad," or "very sad,").

In some implementations, operation 426 may include an operation 432 for requesting the user to confirm incidence of at least one subjective user state as depicted in FIG. 4b. For instance, the confirmation request module 216* of the computing device 10 or the mobile device 30 requesting the user 20* to confirm incidence of at least one subjective user state (e.g., asking the user 20* through the user interface 122* whether the user 20* feels "well").

In some implementations, operation 426 may include an operation 434 for requesting the user to provide an indication of occurrence of at least one subjective user state with respect to the incidence of the at least one objective occurrence as depicted in FIG. 4b. For instance, the requesting module 202* of the computing device 10 or the mobile device 30 requesting the user 20* to provide an indication of occurrence of at least one subjective user state with respect to the incidence of the at least one objective occurrence (e.g., asking the user 20* via a user interface 122* how the user 20* felt after jogging for thirty minutes).

Figure 4C:
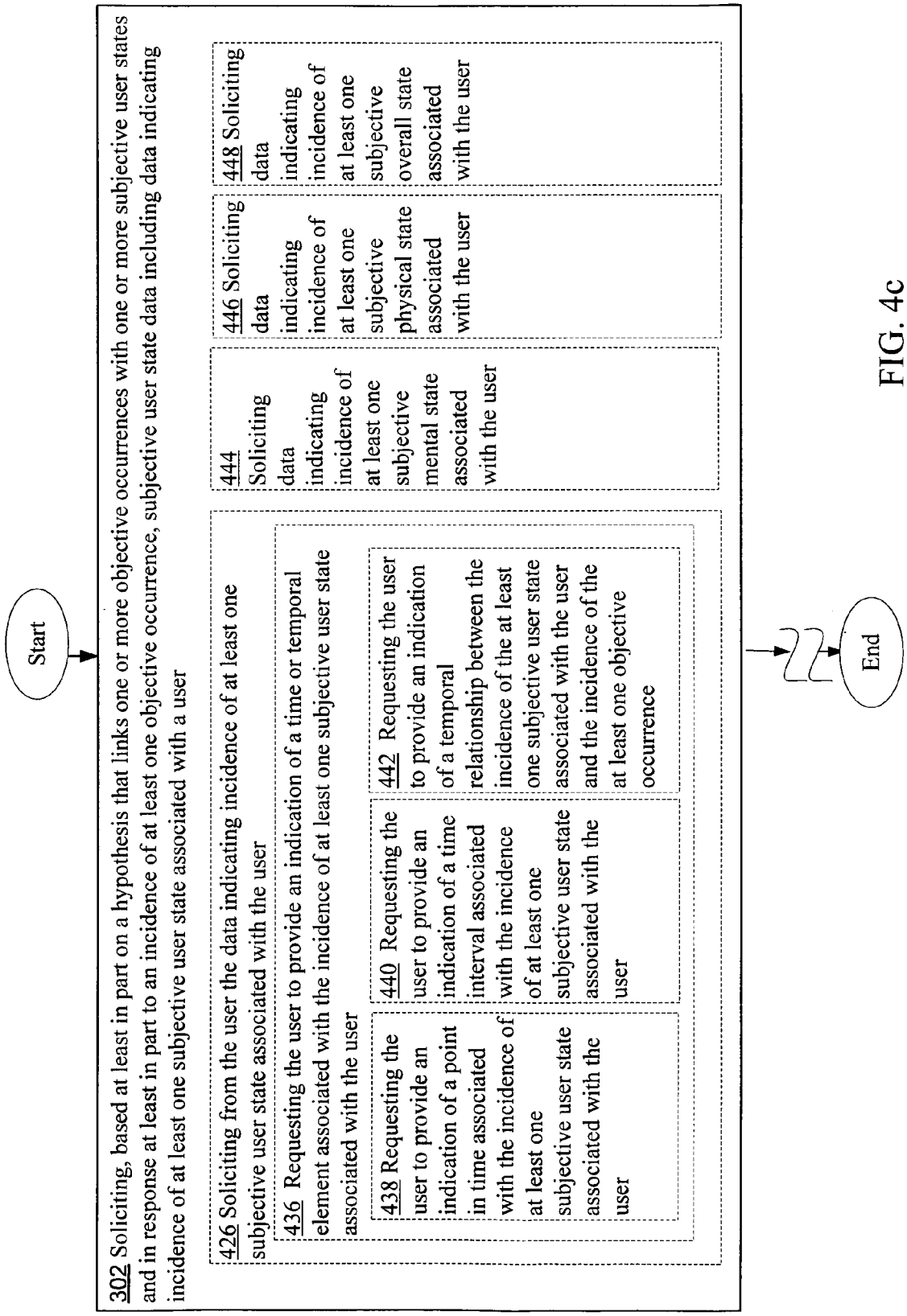
FIG. 4c is a high-level logic flowchart of a process depicting alternate implementations of the subjective user state data solicitation operation 302 of FIG. 3.

In some implementations, operation 426 may include an operation 436 for requesting the user to provide an indication of a time or temporal element associated with the incidence of at least one subjective user state associated with the user as depicted in FIG. 4c. For instance, the time/temporal element request module 218* of the computing device 10 or the mobile device 30 requesting the user 20* to provide an indication of a time or temporal element associated with the incidence of at least one subjective user state associated with the user 20* (e.g., asking the user 20* via a user interface 122 whether the user 20* felt tired after lunch?).

In various implementations, operation 436 may include one or more additional operations. For example, in some implementations, operation 436 may include an operation 438 for requesting the user to provide an indication of a point in time associated with the incidence of at least one subjective user state associated with the user as depicted in FIG. 4c. For instance, the time/temporal element request module 218* of the computing device 10 or the mobile device 30 requesting the user 20* to provide an indication of a point in time (e.g., 8 PM) associated with the incidence of at least one subjective user state (e.g., sleepiness) associated with the user 20*.

In some implementations, operation 436 may include an operation 440 for requesting the user to provide an indication of a time interval associated with the incidence of at least one subjective user state associated with the user as depicted in FIG. 4c. For instance, the time/temporal element request module 218* of the computing device 10 or the mobile device 30 requesting the user 20* to provide an indication of a time interval (e.g., 7 AM to noon) associated with the incidence of at least one subjective user state (e.g., headache) associated with the user 20*.

In some implementations, operation 436 may include an operation 442 for requesting the user to provide an indication of a temporal relationship between the incidence of the at least one subjective user state associated with the user and the incidence of the at least one objective occurrence as depicted in FIG. 4c. For instance, the time/temporal element request module 218* of the computing device 10 or the mobile device 30 requesting the user 20* to provide an indication of a temporal relationship between the incidence of the at least one subjective user state associated with the user 20* and the incidence of the at least one objective occurrence (e.g., asking the user 20* to indicate whether the upset stomach occurred before, after, or at least partly concurrently with eating a hot fudge sundae).

In some implementations, the solicitation operation 302 of FIG. 3 may include an operation 444 for soliciting data indicating incidence of at least one subjective mental state associated with the user as depicted in FIG. 4c. For instance, the subjective user state data solicitation module 101 * of the computing device 10 or the mobile device 30 soliciting data indicating incidence of at least one subjective mental state (e.g., happiness, sadness, anger, alertness or lack of alertness, fatigue, and so forth) associated with the user 20*.

In some implementations, the solicitation operation 302 may include an operation 446 for soliciting data indicating incidence of at least one subjective physical state associated with the user as depicted in FIG. 4c. For instance, the subjective user state data solicitation module 101 * of the computing device 10 or the mobile device 30 soliciting data indicating incidence of at least one subjective physical state (e.g., upset stomach, soreness, lack of pain, blurriness of vision, sense of smell, and so forth) associated with the user 20*.

In some implementations, the solicitation operation 302 may include an operation 448 for soliciting data indicating incidence of at least one subjective overall state associated with the user as depicted in FIG. 4c. For instance, the subjective user state data solicitation module 101 * of the computing device 10 or the mobile device 30 soliciting data indicating incidence of at least one subjective overall state (e.g., good, bad, overall wellness, exhaustion, and so forth) associated with the user 20*.

Figure 4D:
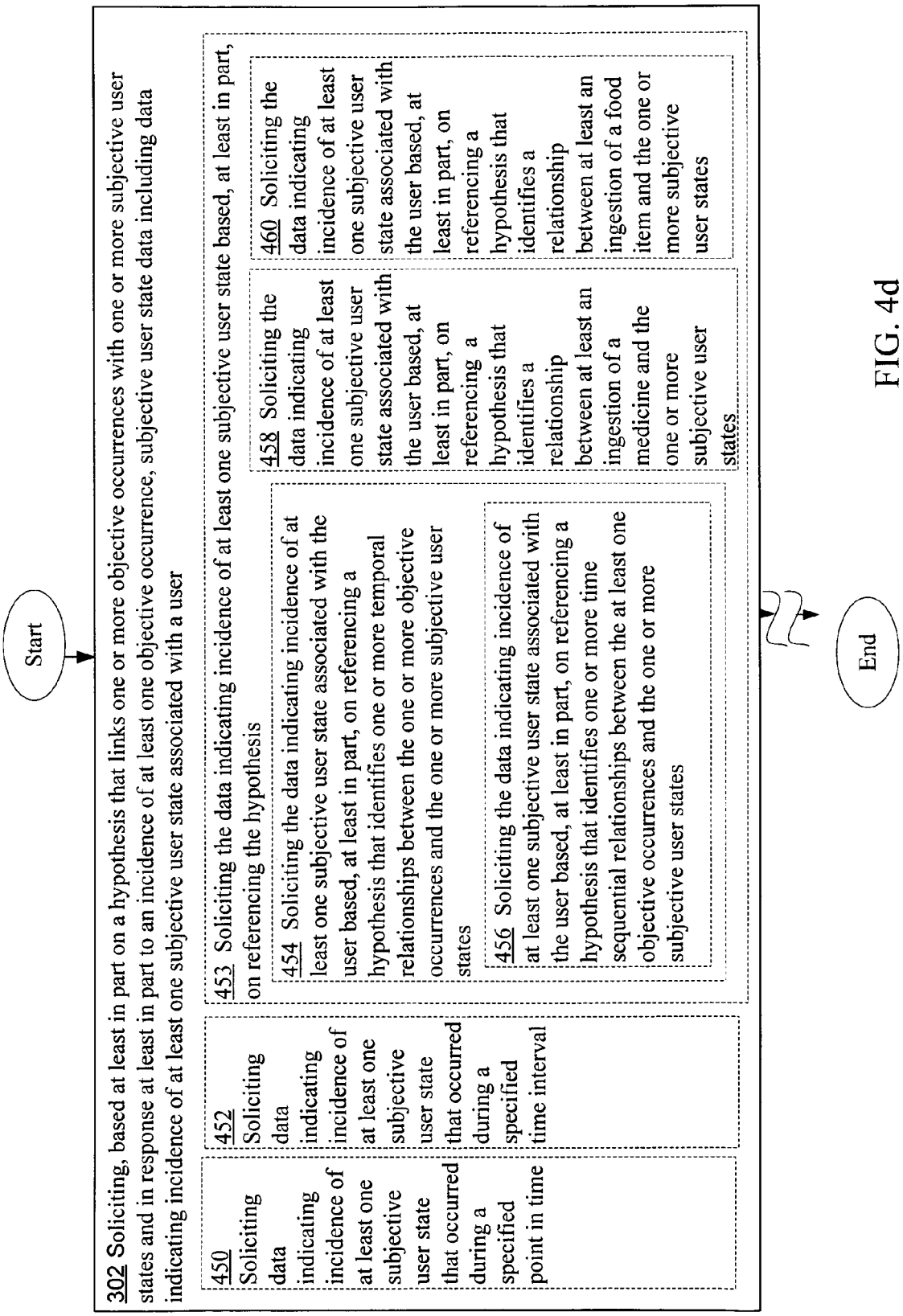
FIG. 4d is a high-level logic flowchart of a process depicting alternate implementations of the subjective user state data solicitation operation 302 of FIG. 3.

In some implementations, the solicitation operation 302 may include an operation 450 for soliciting data indicating incidence of at least one subjective user state that occurred during a specified point in time as depicted in FIG. 4d. For instance, the subjective user state data solicitation module 101* of the computing device 10 or the mobile device 30 soliciting data indicating incidence of at least one subjective user state associated with the user 20* that occurred during a specified point in time (e.g., asking the user 20* how the user 20* felt at 8 PM).

In some implementations, the solicitation operation 302 may include an operation 452 for soliciting data indicating incidence of at least one subjective user state that occurred during a specified time interval as depicted in FIG. 4d. For instance, the subjective user state data solicitation module 101 * of the computing device 10 or the mobile device 30 soliciting data indicating incidence of at least one subjective user state associated with the user 20* that occurred during a specified time interval (e.g., asking the user 20* how the user 20* felt between 8 PM and 10 PM).

In various embodiments, the solicitation operation 302 may include operations that may be particular to the computing device 10, which may be a standalone device or a network server. For example, in some implementations, the solicitation operation 302 may include an operation 453 for soliciting the data indicating incidence of at least one subjective user state based, at least in part, on referencing the hypothesis as depicted in FIG. 4d. In certain implementations, such an operation may be performed by the computing device 10 rather than by the mobile device 30. For these implementations, the subjective user state data solicitation module 101 of the computing device 10 may solicit the data indicating incidence of at least one subjective user state 60a based, at least in part, on the hypothesis referencing module 220 referencing the hypothesis 71, which in some cases may be stored in memory 140.

In various implementations, operation 453 may further include one or more additional operations. For example, in some implementations, operation 453 may include an operation 454 for soliciting the data indicating incidence of at least one subjective user state associated with the user based, at least in part, on referencing a hypothesis that identifies one or more temporal relationships between the one or more objective occurrences and the one or more subjective user states as depicted in FIG. 4d. For instance, the subjective user state data solicitation module 101 of the computing device 10 soliciting the data indicating incidence of at least one subjective user state 60a associated with the user 20* based, at least in part, on referencing a hypothesis 71 that identifies at least one or more temporal relationships between the one or more objective occurrences and the one or more subjective user states (e.g., an hypothesis 71 that indicates that a user 20* or a group of users 20* may tend to have stomach aches after eating hot fudge sundaes).

In some implementations, operation 454 may include an operation 456 for soliciting the data indicating incidence of at least one subjective user state associated with the user based, at least in part, on referencing a hypothesis that identifies one or more time sequential relationships between the at least one objective occurrences and the one or more subjective user states as depicted in FIG. 4d. For instance, the subjective user state data solicitation module 101 of the computing device 10 soliciting the data indicating incidence of at least one subjective user state 60a associated with the user 20* based, at least in part, on referencing a hypothesis 71 that identifies at least one or more time sequential relationships between the at least one objective occurrences and the one or more subjective user states (e.g., hypothesis 71 indicating that a stomach ache will tend to occur two hours after eating a hot fudge sundae).

In some implementations, operation 453 may include an operation 458 for soliciting the data indicating incidence of at least one subjective user state associated with the user based, at least in part, on referencing a hypothesis that identifies a relationship between at least an ingestion of a medicine and the one or more subjective user states as depicted in FIG. 4d. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between at least an ingestion of a medicine (e.g., aspirin) and the one or more subjective user states (e.g., easing of pain).

In some implementations, operation 453 may include an operation 460 for soliciting the data indicating incidence of at least one subjective user state associated with the user based, at least in part, on referencing a hypothesis that identifies a relationship between at least an ingestion of a food item and the one or more subjective user states as depicted in FIG. 4d. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between at least an ingestion of a food item and the one or more subjective user states (e.g., a user 20* tends to be happy after eating a hot fudge sundae).

Figure 4E:
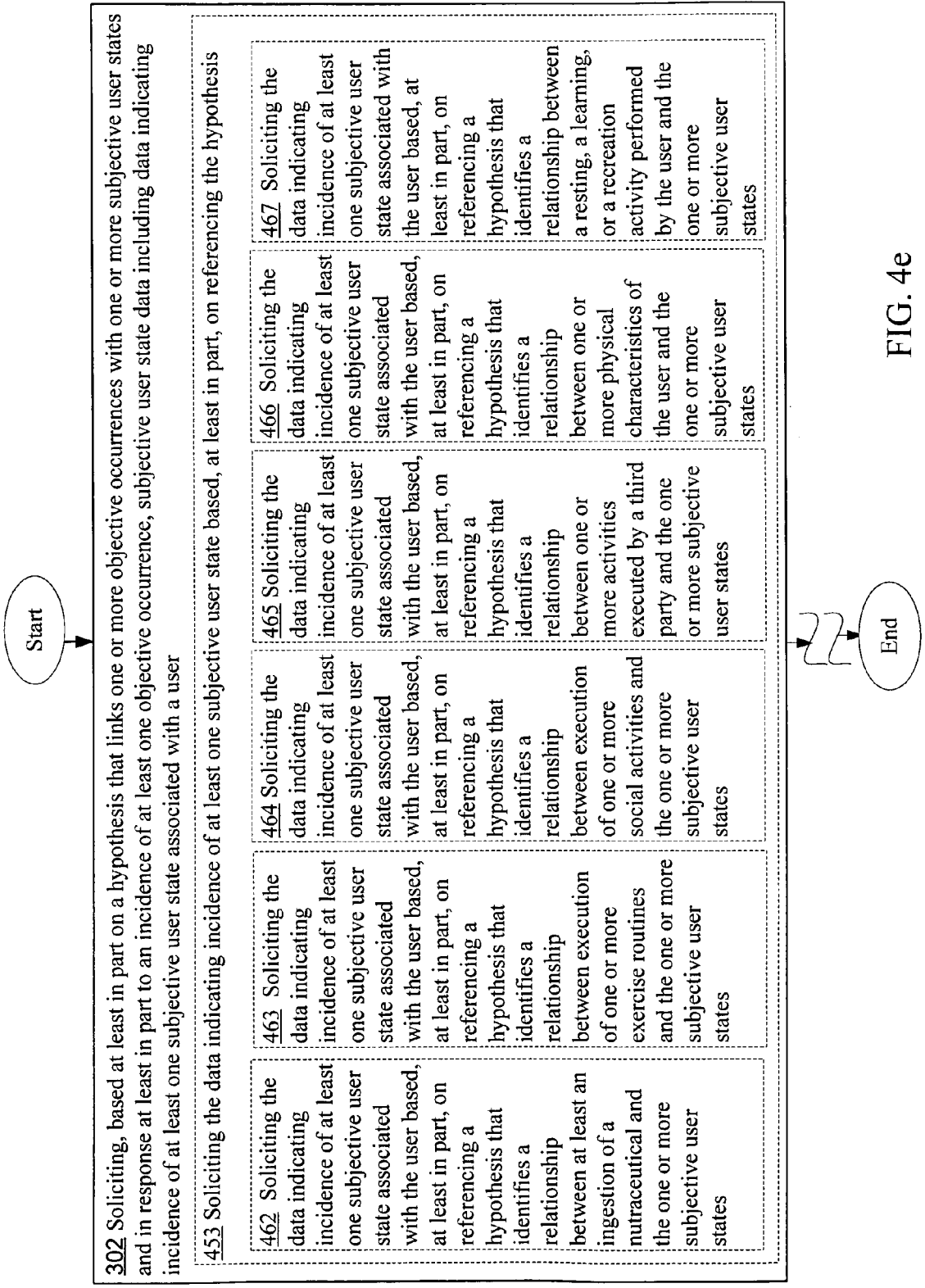
FIG. 4e is a high-level logic flowchart of a process depicting alternate implementations of the subjective user state data solicitation operation 302 of FIG. 3.

In some implementations, operation 453 may include an operation 462 for soliciting the data indicating incidence of at least one subjective user state associated with the user based, at least in part, on referencing a hypothesis that identifies a relationship between at least an ingestion of a nutraceutical and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between at least an ingestion of a nutraceutical and the one or more subjective user states.

In some implementations, operation 453 may include an operation 463 for soliciting the data indicating incidence of at least one subjective user state associated with the user based, at least in part, on referencing a hypothesis that identifies a relationship between execution of one or more exercise routines and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between execution of one or more exercise routines (e.g., jogging) and the one or more subjective user states (e.g., sore knees). For example, the hypothesis 71 may indicate that sore knees may result after jogging.

In some implementations, operation 453 may include an operation 464 for soliciting the data indicating incidence of at least one subjective user state associated with the user based, at least in part, on referencing a hypothesis that identifies a relationship between execution of one or more social activities and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between execution of one or more social activities (e.g., meeting in-laws) and the one or more subjective user states (e.g., anxiety). For example, the hypothesis 71 may indicate that feelings of anxiety may occur when meeting the in-laws.

In some implementations, operation 453 may include an operation 465 for soliciting the data indicating incidence of at least one subjective user state associated with the user based, at least in part, on referencing a hypothesis that identifies a relationship between one or more activities executed by a third party and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between one or more activities executed by a third party (e.g., boss leaving town) and the one or more subjective user states (e.g., relaxation). For example, the hypothesis 71 may indicate that a user 20* may be relaxed or more relaxed when the boss leaves town.

In some implementations, operation 453 may include an operation 466 for soliciting the data indicating incidence of at least one subjective user state associated with the user based, at least in part, on referencing a hypothesis that identifies a relationship between one or more physical characteristics of the user and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between one or more physical characteristics (e.g., high blood pressure) of the user 20* and the one or more subjective user states (e.g., fatigue). For example, the hypothesis 71 may indicate that a user 20* may be fatigued or more fatigued whenever the blood pressure of the user 20* is high.

In some implementations, operation 453 may include an operation 467 for soliciting the data indicating incidence of at least one subjective user state associated with the user based, at least in part, on referencing a hypothesis that identifies a relationship between a resting, a learning, or a recreation activity performed by the user and the one or more subjective user states as depicted in FIG. 4e. For instance, the subjective user state data solicitation module 101 of the computing device 10 soliciting (e.g., via the network interface 120 or via the user interface 122) the data indicating incidence of at least one subjective user state 60a associated with the user 20* based, at least in part, on referencing a hypothesis 71 that identifies a relationship between a resting (e.g., sleeping), a learning (e.g., reading a book or attending a lecture or class), or a recreation (e.g., playing golf) activity performed by the user 20* and the one or more subjective user states.

Figure 4F:
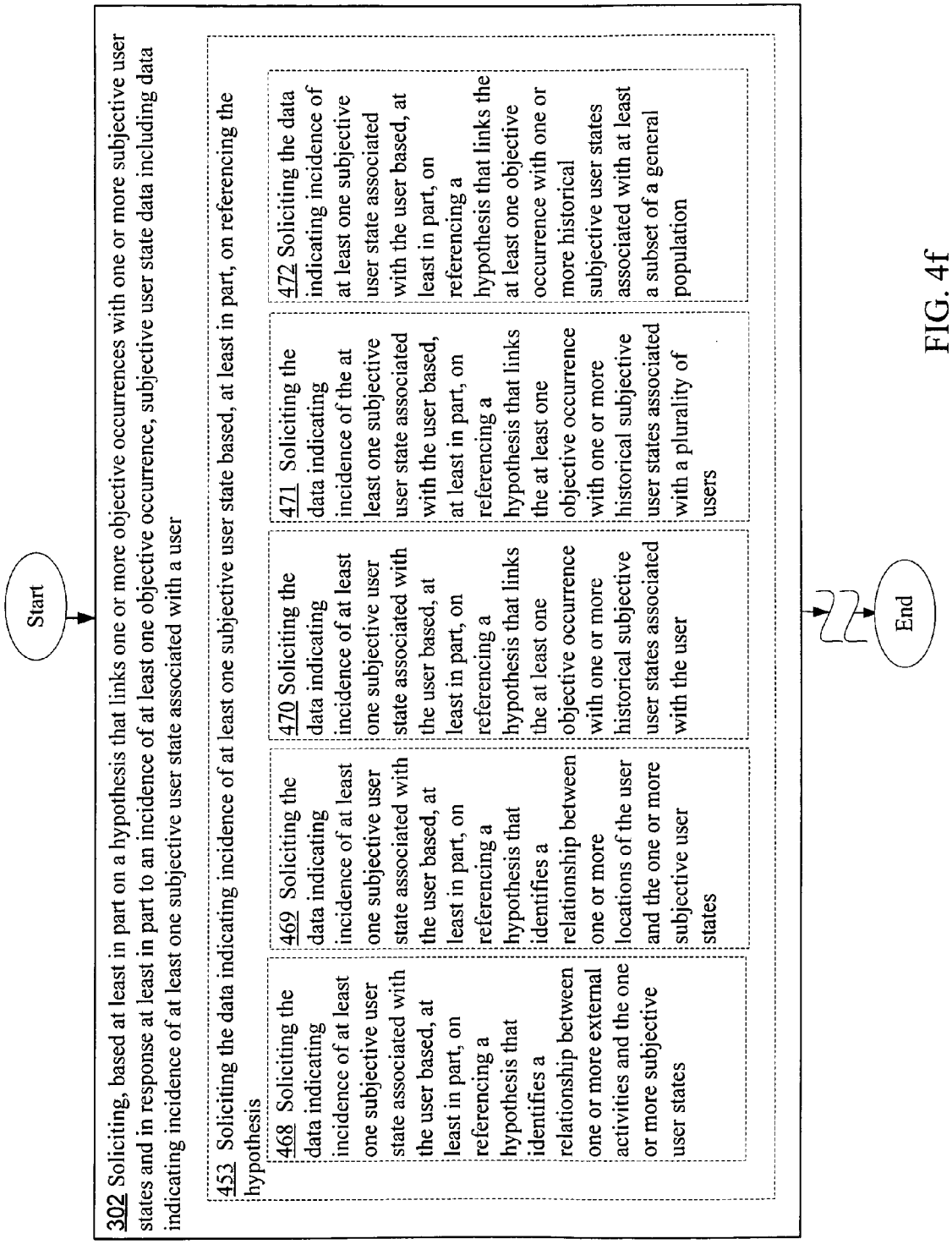
FIG. 4f is a high-level logic flowchart of a process depicting alternate implementations of the subjective user state data solicitation operation 302 of FIG. 3.

In some implementations, operation 453 may include an operation 468 for soliciting the data indicating incidence of at least one subjective user state associated with the user based, at least in part, on referencing a hypothesis that identifies a relationship between one or more external activities and the one or more subjective user states as depicted in FIG. 4f. For instance, the subjective user state data solicitation module 101 of the computing device 10 soliciting (e.g., via the network interface 120 or via the user interface 122) the data indicating incidence of at least one subjective user state 60*a* associated with the user 20* based, at least in part, on referencing a hypothesis 71 that identifies a relationship between one or more external activities (e.g., overcast weather) and the one or more subjective user states (e.g., depression).

In some implementations, operation 453 may include an operation 469 for soliciting the data indicating incidence of at least one subjective user state associated with the user based, at least in part, on referencing a hypothesis that identifies a relationship between one or more locations of the user and the one or more subjective user states as depicted in FIG. 4*f*. For instance, the subjective user state data solicitation module 101 of the computing device 10 soliciting (e.g., via the network interface 120 or via the user interface 122) the data indicating incidence of at least one subjective user state 60*a* associated with the user 20* based, at least in part, on referencing a hypothesis 71 that identifies a relationship between one or more locations (e.g., New York City) of the user 20* and the one or more subjective user states (e.g., anxiety).

In some implementations, operation 453 may include an operation 470 for soliciting the data indicating incidence of at least one subjective user state associated with the user based, at least in part, on referencing a hypothesis that links the at least one objective occurrence with one or more historical subjective user states associated with the user as depicted in FIG. 4*f*. For instance, the subjective user state data solicitation module 101 of the computing device 10 soliciting (e.g., via the network interface 120 or via the user interface 122) the data indicating incidence of at least one subjective user state 60*a* associated with the user 20* based, at least in part, on referencing a hypothesis 71 that links the at least one objective occurrence (e.g., user 20* exercising) with one or more historical subjective user states (e.g., feeling energetic) associated with the user 20*.

In some implementations, operation 453 may include an operation 471 for soliciting the data indicating incidence of the at least one subjective user state associated with the user based, at least in part, on referencing a hypothesis that links the at least one objective occurrence with one or more historical subjective user states associated with a plurality of users as depicted in FIG. 4*f*. For instance, the subjective user state data solicitation module 101 of the computing device 10 soliciting (e.g., via the network interface 120 or via the user interface 122) the data indicating incidence of at least one subjective user state 60*a* associated with the user 20* based, at least in part, on referencing a hypothesis 71 that links the at least one objective occurrence (e.g., stock market performance) with one or more historical subjective user states (e.g., depression) associated with a plurality of users 20*.

In some implementations, operation 453 may include an operation 472 for soliciting the data indicating incidence of at least one subjective user state associated with the user based, at least in part, on referencing a hypothesis that links the at least one objective occurrence with one or more historical subjective user states associated with at least a subset of a general population as depicted in FIG. 4*f*. For instance, the subjective user state data solicitation module 101 of the computing device 10 soliciting (e.g., via the network interface 120 or via the user interface 122) the data indicating incidence of at least one subjective user state 60*a* associated with the user 20* based, at least in part, on referencing a hypothesis 71 that links the at least one objective occurrence with one or more historical subjective user states associated with at least a subset of a general population.

Figure 4G:
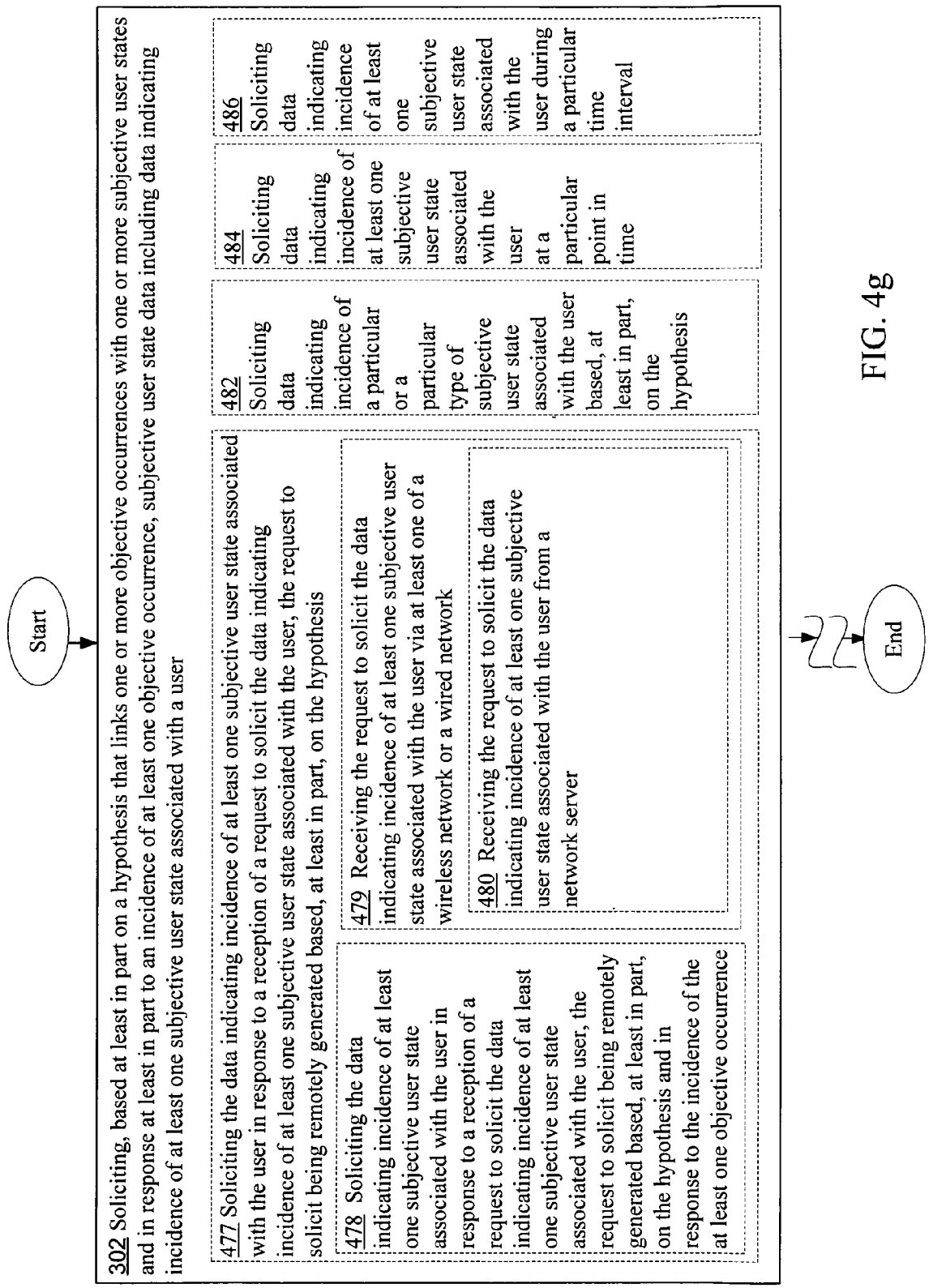
FIG. 4g is a high-level logic flowchart of a process depicting alternate implementations of the subjective user state data solicitation operation 302 of FIG. 3.

In various implementations, the solicitation operation 302 may include one or more operations that may be performed by the mobile device 30 rather than by the computing device 10. For example, in some implementations, the solicitation operation 302 may include an operation 477 for soliciting the data indicating incidence of at least one subjective user state associated with the user in response to a reception of a request to solicit the data indicating incidence of at least one subjective user state associated with the user, the request to solicit being remotely generated based, at least in part, on the hypothesis as depicted in FIG. 4*g*. For instance, the subjective user state data solicitation module 101' of the mobile device 30 soliciting the data indicating incidence of at least one subjective user state 60*a* associated with the user 20*a* from the user 20*a* in response to the "request to solicit" reception module 270 of the mobile device 30 receiving (e.g., receiving from a network server such as the computing device 10 via a wireless and/or wired network 40) a request to solicit the data indicating incidence of at least one subjective user state 60*a* associated with the user 20*a*, the request to solicit being remotely generated (e.g., remotely generated at the computing device 10) based, at least in part, on the hypothesis 71.

In some implementations, operation 477 may further include an operation 478 for soliciting the data indicating incidence of at least one subjective user state associated with the user in response to a reception of a request to solicit the data indicating incidence of at least one subjective user state associated with the user, the request to solicit being remotely generated based, at least in part, on the hypothesis and in response to the incidence of the at least one objective occurrence as depicted in FIG. 4*g*. For instance, the subjective user state data solicitation module 101' of the mobile device 30 soliciting the data indicating incidence of at least one subjective user state 60*a* associated with the user 20*a* from the user 20*a* in response to the "request to solicit" reception module 270 of the mobile device 30 receiving (e.g., receiving from a network server such as the computing device 10 via a wireless and/or wired network 40) a request to solicit the data indicating incidence of the at least one subjective user state 60*a* associated with the user 20*a*, the request to solicit being remotely generated (e.g., remotely generated by a network server such as the computing device) based, at least in part, on the hypothesis 71 and in response to the incidence of the at least one objective occurrence (e.g., the incidence of the at least one objective occurrence being reported to the computing device 10).

In some implementations, operation 477 may further include an operation 479 for receiving the request to solicit the data indicating incidence of at least one subjective user state associated with the user via at least one of a wireless network or a wired network as depicted in FIG. 4*g*. For instance, the "request to solicit" reception module 270 of the mobile device 30 receiving the request to solicit the data indicating incidence of at least one subjective user state 60*a* associated with the user 20*a* via at least one of a wireless network or a wired network 40.

Operation 479, in turn, may further include an operation 480 for receiving the request to solicit the data indicating incidence of at least one subjective user state associated with the user from a network server as depicted in FIG. 4*g*. For instance, the "request to solicit" reception module 270 of the mobile device 30 receiving the request to solicit the data indicating incidence of at least one subjective user state 60*a* associated with the user 20*a* from a network server (e.g., computing device 10).

In various implementations, the solicitation operation 302 of FIG. 3 may include an operation 482 for soliciting data indicating incidence of a particular or a particular type of subjective user state associated with the user based, at least in part, on the hypothesis as depicted in FIG. 4*g*. For instance, the subjective user state data solicitation module 101* of the computing device 10 or the mobile device 30 soliciting data indicating incidence of a particular or a particular type of subjective user state associated with the user 20* based, at least in part, on the hypothesis 71. For example, asking for the subjective mental state a user 20* (e.g., asking the user 20* whether the user 20* is happy or sad?).

In some implementations, the solicitation operation 302 may include an operation 484 for soliciting data indicating incidence of at least one subjective user state associated with the user at a particular point in time as depicted in FIG. 4g. For instance, the subjective user state data solicitation module 101 * of the computing device 10 or the mobile device 30 soliciting data indicating incidence of at least one subjective user state associated with the user 20* at or for a particular point in time (e.g., 1 PM). For example, asking a user 20* how the user 20* felt at 1 PM.

In some implementations, the solicitation operation 302 may include an operation 486 for soliciting data indicating incidence of at least one subjective user state associated with the user during a particular time interval as depicted in FIG. 4g. For instance, the subjective user state data solicitation module 101 * of the computing device 10 or the mobile device 30 soliciting data indicating incidence of at least one subjective user state 60a associated with the user 20* during a particular time interval (e.g., 1 PM to 3 PM). For example, asking a user 20* how the user 20* felt between 1 PM and 3 PM.

Figure 5A:
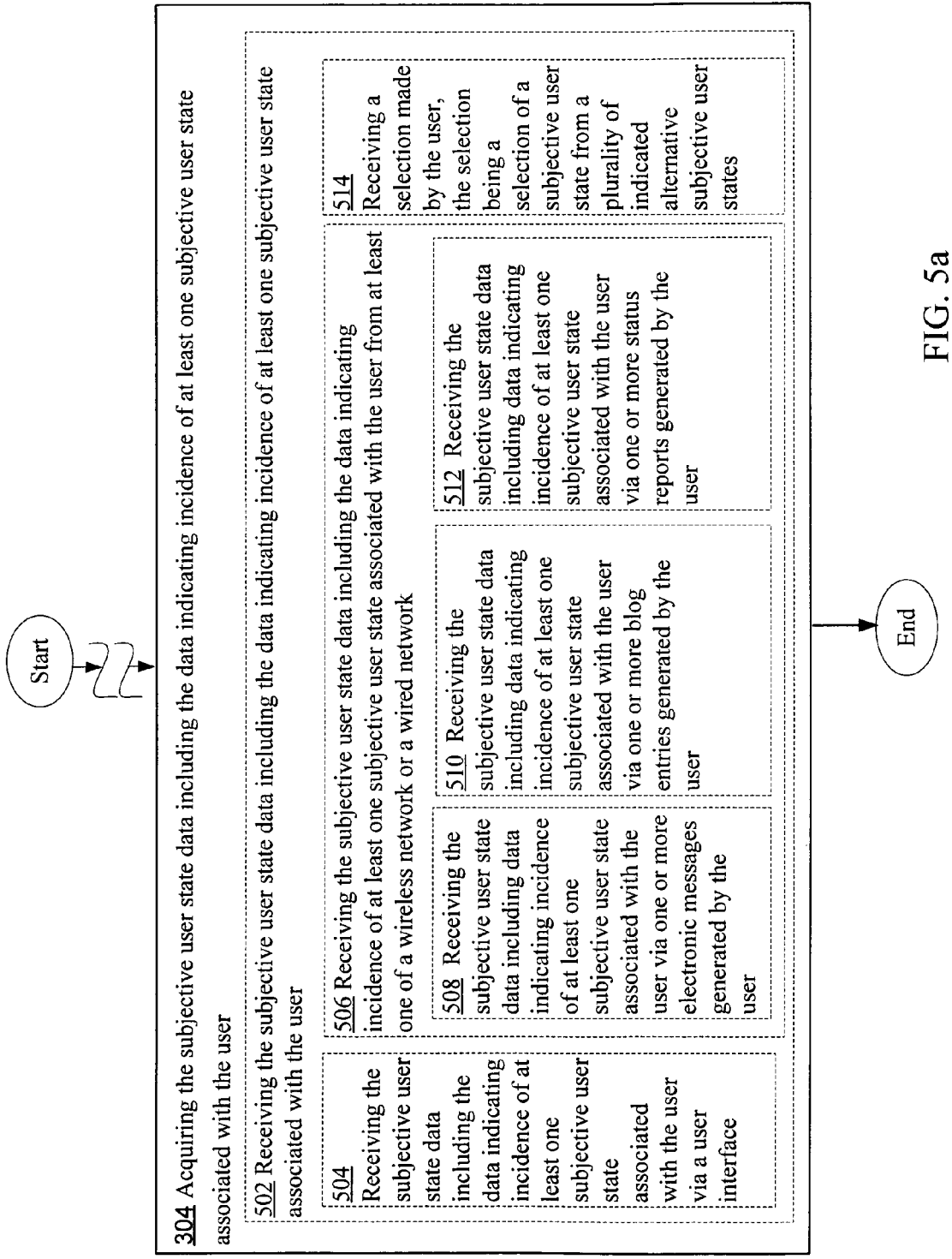
FIG. 5a is a high-level logic flowchart of a process depicting alternate implementations of the subjective user state data acquisition operation 304 of FIG. 3.

Referring back to FIG. 3, the subjective user state data acquisition operation 304 may include one or more additional operations in various alternative implementations. For example, in some implementations, the subjective user state data acquisition operation 304 may include a reception operation 502 for receiving the subjective user state data including the data indicating incidence of at least one subjective user state associated with the user as depicted in FIG. 5a. For instance the subjective user state data reception module 224* of the computing device 10 or the mobile device 30 receiving the subjective user state data 60 including the data indicating incidence of at least one subjective user state 60a associated with the user 20*.

In various implementations, the reception operation 502 may include one or more additional operations. For example, in some implementations, the reception operation 502 may include an operation 504 for receiving the subjective user state data including the data indicating incidence of at least one subjective user state associated with the user via a user interface as depicted in FIG. 5a. For instance, the user interface reception module 226* of the computing device 10 or the mobile device 30 receiving the subjective user state data 60 including the data indicating incidence of at least one subjective user state 60a associated with the user 20* via a user interface 122* (e.g., an audio system or a display system).

The reception operation 502, in some implementations, may include operations that may be particular to the computing device 10 (e.g., when the computing device is a network server) and may not be executed by the mobile device 30. For example, in some implementations, the reception operation 502 may include an operation 506 for receiving the subjective user state data including the data indicating incidence of at least one subjective user state associated with the user from at least one of a wireless network or a wired network as depicted in FIG. 5a. For instance, the network interface reception module 227 of the computing device 10 receiving the subjective user state data 60 including the data indicating incidence of at least one subjective user state 60a associated with the user 20a from at least one of a wireless network or a wired network 40.

In some implementations, operation 506 may further include an operation 508 for receiving the subjective user state data including data indicating incidence of at least one subjective user state associated with the user via one or more electronic messages generated by the user as depicted in FIG. 5a. For instance, the network interface reception module 227 of the computing device 10 receiving the subjective user state data 60 including the data indicating incidence of at least one subjective user state 60a associated with the user 20a via one or more electronic messages generated by the user 20a.

In some implementations, operation 506 may include an operation 510 for receiving the subjective user state data including data indicating incidence of at least one subjective user state associated with the user via one or more blog entries generated by the user as depicted in FIG. 5a. For instance, the network interface reception module 227 of the computing device 10 receiving the subjective user state data 60 including the data indicating incidence of at least one subjective user state 60a associated with the user 20a via one or more blog entries (e.g., microblog entries) generated by the user 20a.

In some implementations, operation 506 may include an operation 512 for receiving the subjective user state data including data indicating incidence of at least one subjective user state associated with the user via one or more status reports generated by the user as depicted in FIG. 5a. For instance, the network interface reception module 227 of the computing device 10 receiving the subjective user state data 60 including the data indicating incidence of at least one subjective user state 60a associated with the user 20a via one or more status reports (e.g., social networking status reports) generated by the user 20a.

In certain implementations, the reception operation 502 may include an operation 514 for receiving a selection made by the user, the selection being a selection of a subjective user state from a plurality of indicated alternative subjective user states as depicted in FIG. 5a. For instance, the subjective user state data reception module 224* of the computing device 10 or the mobile device 30 receiving a selection made by the user 20*, the selection being a selection of a subjective user state (e.g., happy) from a plurality of indicated alternative subjective user states (e.g., happy, sad, in pain, alert, and so forth) that may be indicated via, for example, a user interface 122*.

Figure 5B:
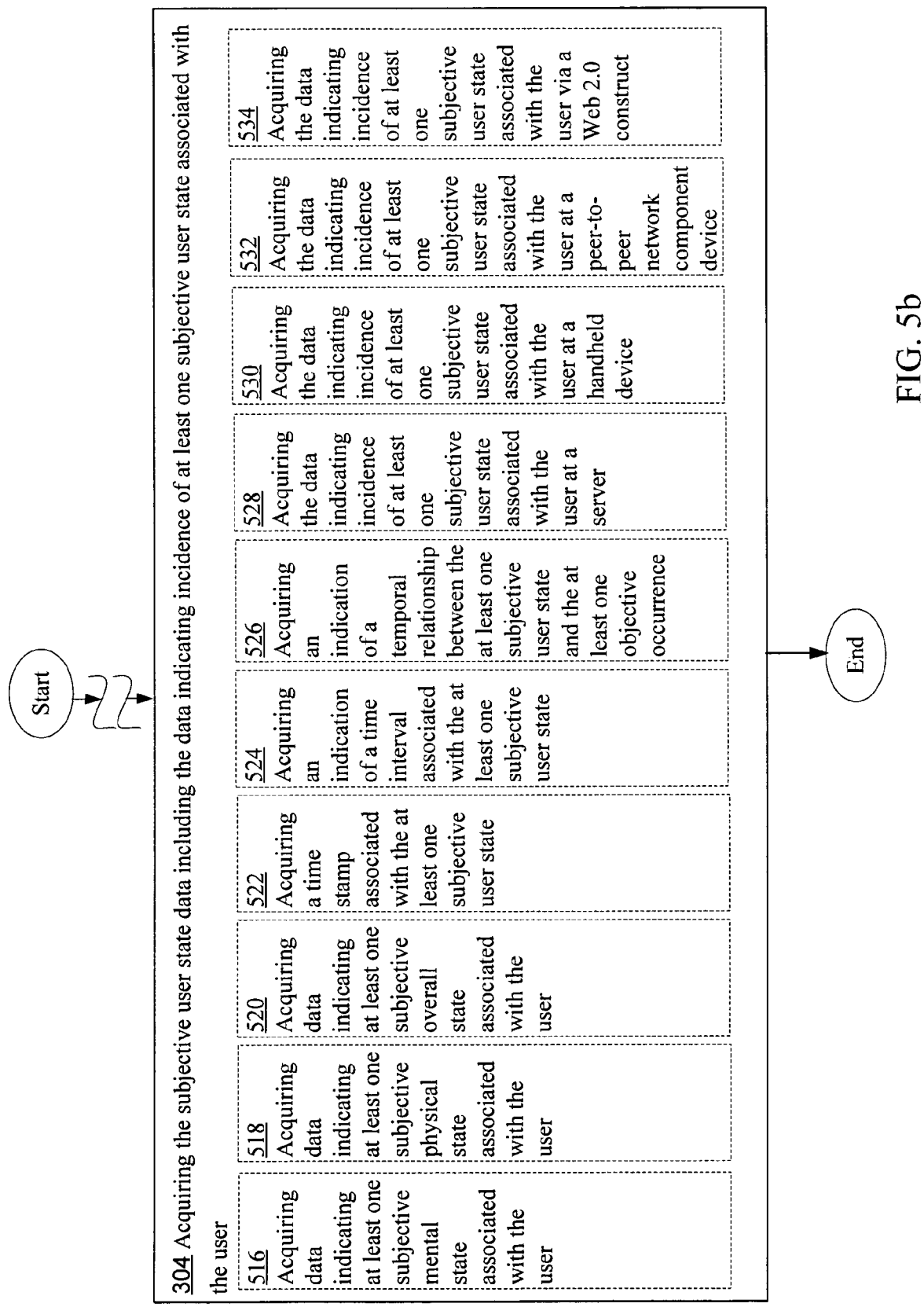
FIG. 5b is a high-level logic flowchart of a process depicting alternate implementations of the subjective user state data acquisition operation 304 of FIG. 3.

In some implementations, the subjective user state data acquisition operation 304 of FIG. 3 may include an operation 516 for acquiring data indicating at least one subjective mental state associated with the user as depicted in FIG. 5b. For instance, the subjective user state data acquisition module 102* of the computing device 10 or the mobile device 30 acquiring (e.g., receiving or obtaining through a network interface 120* or through a user interface 122*) data indicating at least one subjective mental state (e.g., level of happiness, level of sadness, alertness, level of fatigue, level of pain, and so forth) associated with the user 20*.

In some implementations, the subjective user state data acquisition operation 304 may include an operation 518 for acquiring data indicating at least one subjective physical state associated with the user as depicted in FIG. 5b. For instance, the subjective user state data acquisition module 102* of the computing device 10 or the mobile device 30 acquiring (e.g., receiving or obtaining through a network interface 120* or through a user interface 122*) data indicating at least one subjective physical state (e.g., vision acuity, hearing acuity, level of physical pain, and so forth) associated with the user 20*.

In some implementations, the subjective user state data acquisition operation 304 may include an operation 520 for acquiring data indicating at least one subjective overall state associated with the user as depicted in FIG. 5b. For instance, the subjective user state data acquisition module 102* of the computing device 10 or the mobile device 30 acquiring (e.g., receiving or obtaining through a network interface 120* or through a user interface 122*) data indicating at least one subjective overall state (e.g., overall wellness, good, bad, and so forth) associated with the user 20*.

In some implementations, the subjective user state data acquisition operation 304 may include an operation 522 for acquiring a time stamp associated with the at least one subjective user state as depicted in FIG. 5b. For instance, the time stamp acquisition module 230* of the computing device 10 or the mobile device 30 acquiring (e.g., receiving through a network interface 120 or a user interface 122, or by self-generating) at least one time stamp associated with the at least one subjective user state.

In some implementations, the subjective user state data acquisition operation 304 may include an operation 524 for acquiring an indication of a time interval associated with the at least one subjective user state as depicted in FIG. 5b. For instance, the time interval acquisition module 241* of the computing device 10 or the mobile device 30 acquiring (e.g., receiving through a network interface 120 or a user interface 122, or by self-generating) at least an indication of a time interval associated with the at least one subjective user state.

In some implementations, the subjective user state data acquisition operation 304 may include an operation 526 for acquiring an indication of a temporal relationship between the at least one subjective user state and the at least one objective occurrence as depicted in FIG. 5b. For instance, the temporal relationship acquisition module 232* of the computing device 10 or the mobile device 30 acquiring (e.g., receiving through a network interface 120 or a user interface 122, or by self-generating) at least an indication of a temporal relationship (e.g., before, after, or at least partly concurrently) between the at least one subjective user state (e.g., subjective mental state) and the at least one objective occurrence (e.g., ingestion of medicine).

In some implementations, the subjective user state data acquisition operation 304 may include an operation 528 for acquiring the data indicating incidence of at least one subjective user state associated with the user at a server as depicted in FIG. 5b. For instance, when the computing device 10 is a network server and is acquiring the data indicating incidence of at least one subjective user state 60a associated with the user 20a.

In some implementations, the subjective user state data acquisition operation 304 may include an operation 530 for acquiring the data indicating incidence of at least one subjective user state associated with the user at a handheld device as depicted in FIG. 5b. For instance, when the computing device 10 or the mobile device 30 is a handheld device (e.g., a cellular telephone, a PDA, and so forth) and is acquiring the data indicating incidence of at least one subjective user state 60a associated with the user 20*.

In some implementations, the subjective user state data acquisition operation 304 may include an operation 532 for acquiring the data indicating incidence of at least one subjective user state associated with the user at a peer-to-peer network component device as depicted in FIG. 5b. For instance, when the computing device 10 or the mobile device 30 is a peer-to-peer network component device and is acquiring the data indicating incidence of at least one subjective user state 60 associated with the user 20*.

In some implementations, the subjective user state data acquisition operation 304 may include an operation 534 for acquiring the data indicating incidence of at least one subjective user state associated with the user via a Web 2.0 construct as depicted in FIG. 5b. For instance, when the computing device 10 or the mobile device 30 is acquiring the data indicating incidence of at least one subjective user state 60a associated with the user 20* via a Web 2.0 construct.

Figure 6:
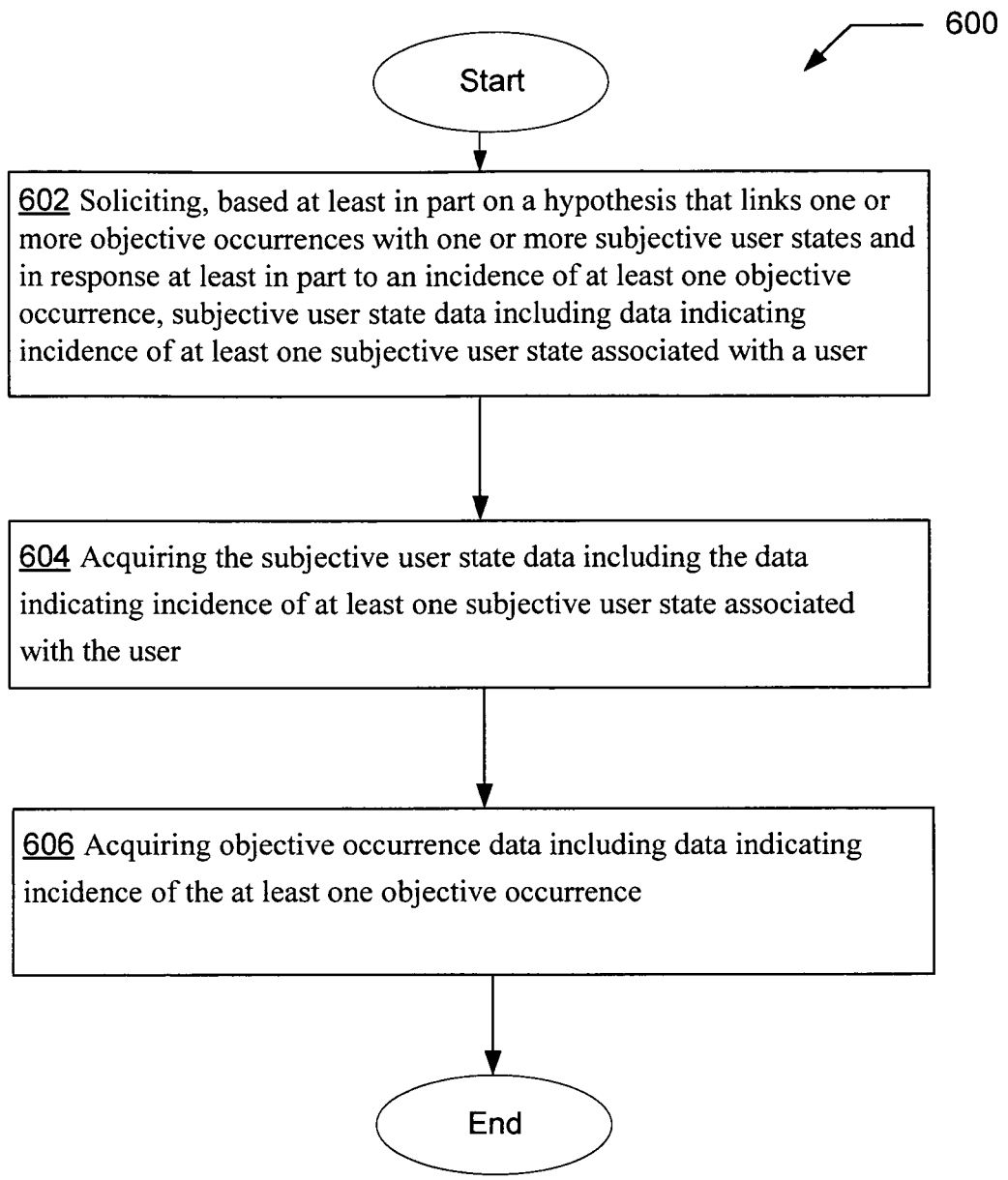
FIG. 6 is a high-level logic flowchart of another process.

Referring to FIG. 6 illustrating another operational flow 600 in accordance with various embodiments. Operational flow 600 includes certain operations that mirror the operations included in operational flow 300 of FIG. 3. These operations include a subjective user state data solicitation operation 602 and a subjective user state data acquisition operation 604 that corresponds to and mirror the subjective user state data solicitation operation 302 and the subjective user state data acquisition operation 304, respectively, of FIG. 3.

In addition, operational flow 600 includes an objective occurrence data acquisition operation 606 for acquiring objective occurrence data including data indicating incidence of the at least one objective occurrence as depicted in FIG. 6. For instance, the objective occurrence data acquisition module 104* of the computing device 10 or the mobile device 30 acquiring (e.g., receiving, gathering, or retrieving via network interface 120* or via the user interface 122*) objective occurrence data 70* including data indicating incidence of the at least one objective occurrence.

Figure 7A:
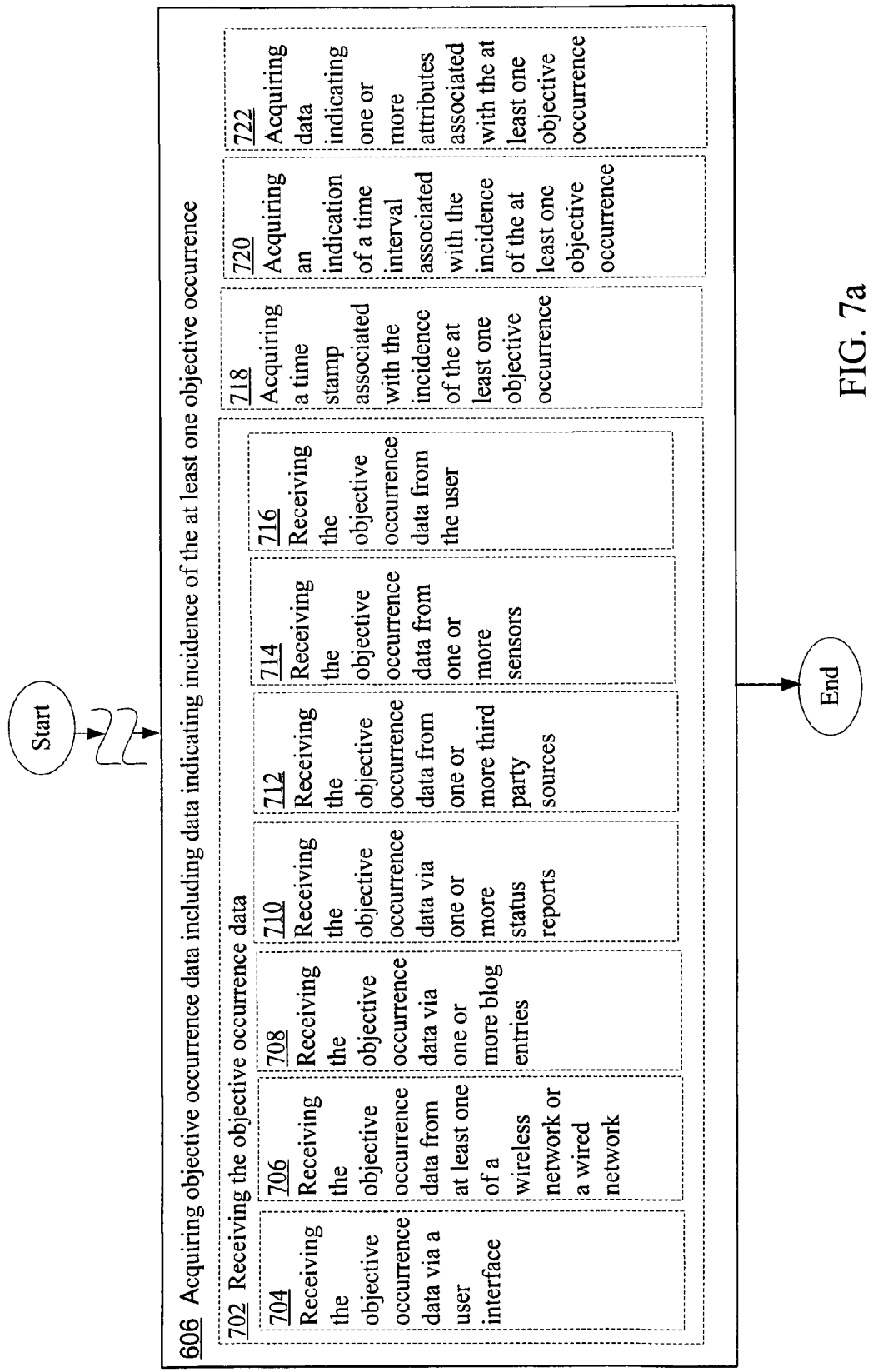
FIG. 7a is a high-level logic flowchart of a process depicting alternate implementations of the objective occurrence data acquisition operation 606 of FIG. 6.

In various alternative implementations, the objective occurrence data acquisition operation 606 may include one or more additional operations. For example, in some implementations, operation 606 may include a reception operation 702 for receiving the objective occurrence data as depicted in FIG. 7a. For instance, the objective occurrence data reception module 234* of the computing device 10 or the mobile device 30 receiving the objective occurrence data 70*.

The reception operation 702, in turn, may include one or more additional operations in various alternative implementations. For example, in some implementations, the reception operation 702 may include an operation 704 for receiving the objective occurrence data via a user interface as depicted in FIG. 7a. For instance, the user interface data reception module 235* of the computing device 10 (e.g., when the computing device 10 is a standalone device) or the mobile device 30 receiving the objective occurrence data 70c via a user interface 122* (e.g., a keyboard, a mouse, a touchscreen, a microphone, an image capturing device such as a digital camera, and so forth).

In some implementations, the reception operation 702 may include an operation 706 for receiving the objective occurrence data from at least one of a wireless network or a wired network as depicted in FIG. 7a. For instance, the network interface data reception module 236* of the computing device 10 or the mobile device 30 receiving the objective occurrence data 70* from at least one of a wireless network or a wired network 40. Note that a mobile device 30, in some cases, may be provided with the objective occurrence data 70a from one or more third party sources 50. In such a scenario, the mobile device 30 may initially collect the objective occurrence data 70a before transmitting the objective occurrence data 70a to, for example, the computing device 10 (e.g., network server) where such data may be processed during a correlation operation.

In some implementations, the reception operation 702 may include an operation 708 for receiving the objective occurrence data via one or more blog entries as depicted in FIG. 7a. For instance, the network interface data reception module 236* of the computing device 10 or the mobile device 30 receiving the objective occurrence data 70a or 70c via one or more blog entries (e.g., microblog entries).

In some implementations, the reception operation 702 may include an operation 710 for receiving the objective occurrence data via one or more status reports as depicted in FIG. 7a. For instance, the network interface data reception module 236* of the computing device 10 or the mobile device 30 receiving the objective occurrence data 70a or 70c via one or more status reports (e.g., social networking status reports).

In some implementations, the reception operation 702 may include an operation 712 for receiving the objective occurrence data from one or more third party sources as depicted in FIG. 7a. For instance, the network interface data reception module 236* of the computing device 10 or the mobile device 30 receiving the objective occurrence data 70c from one or more third party sources 50.

In some implementations, the reception operation 702 may include an operation 714 for receiving the objective occurrence data from one or more sensors as depicted in FIG. 7a. For instance, the network interface data reception module 236* of the computing device 10 or the mobile device 30 receiving the objective occurrence data 70c from one or more sensors 35.

In some implementations, the reception operation 702 may include an operation 716 for receiving the objective occurrence data from the user as depicted in FIG. 7a. For instance, the network interface data reception module 236 of the computing device 10 receiving the objective occurrence data 70c from the user 20a.

In various implementations, the objective occurrence data acquisition operation 606 of FIG. 6 may include an operation 718 for acquiring a time stamp associated with the incidence of the at least one objective occurrence as depicted in FIG. 7a. For instance, the time stamp acquisition module 240* of the computing device 10 or the mobile device 30 acquiring (e.g., by receiving or by self-generating) a time stamp associated with the incidence of the at least one objective occurrence.

In some implementations, the objective occurrence data acquisition operation 606 may include an operation 720 for acquiring an indication of a time interval associated with the incidence of the at least one objective occurrence as depicted in FIG. 7a. For instance, the time interval acquisition module 241* of the computing device 10 or the mobile device 30 acquiring an indication of a time interval associated with the incidence of the at least one objective occurrence.

In some implementations, the objective occurrence data acquisition operation 606 may include an operation 722 for acquiring data indicating one or more attributes associated with the at least one objective occurrence as depicted in FIG. 7a. For instance, the objective occurrence data acquisition module 104* of the computing device 10 or the mobile device 30 acquiring data indicating one or more attributes (e.g., quantity and brand of a medicine) associated with the at least one objective occurrence (e.g., ingestion of the medicine).

Figure 7B:
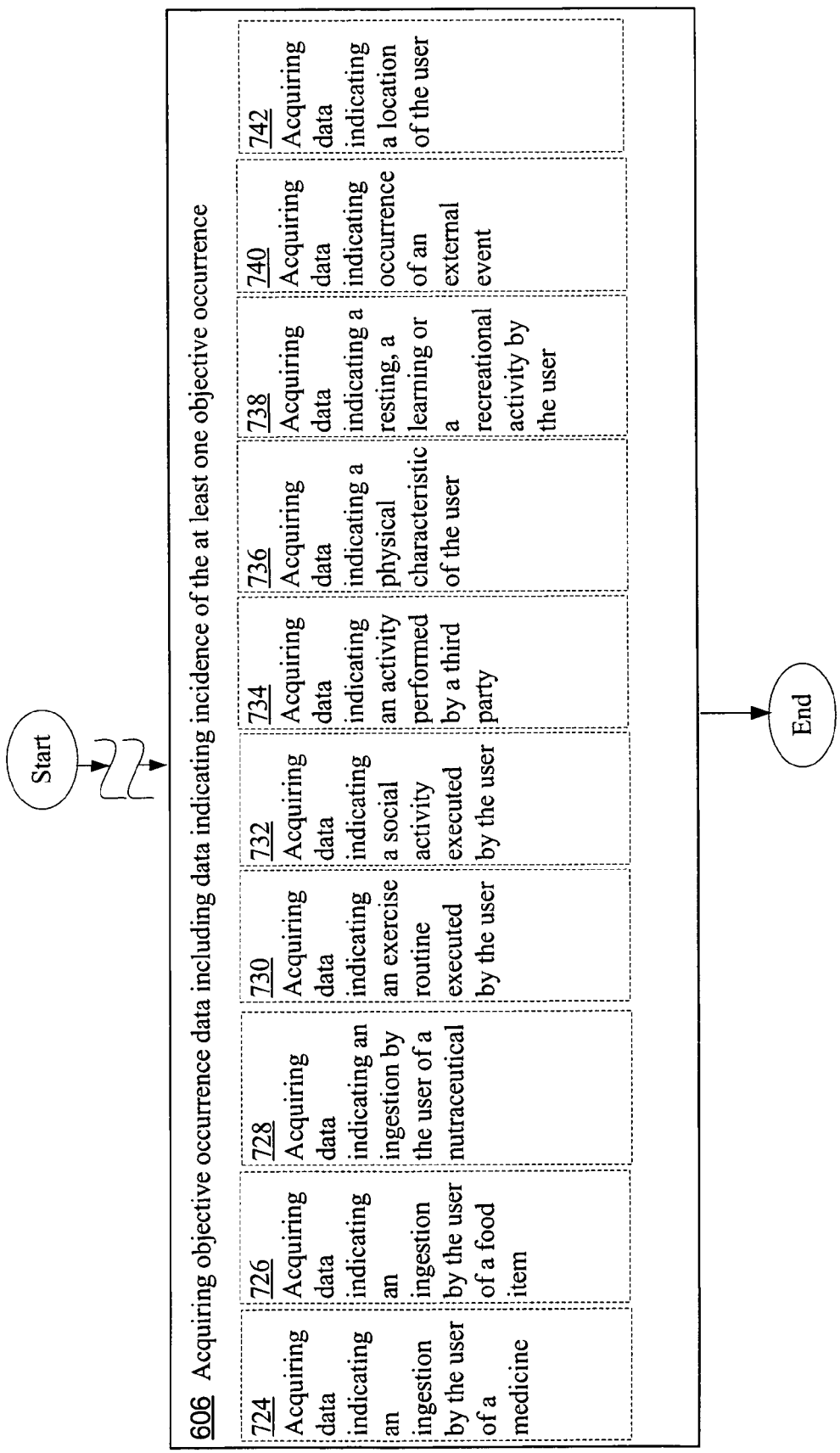
FIG. 7b is a high-level logic flowchart of a process depicting alternate implementations of the objective occurrence data acquisition operation 606 of FIG. 6.

In some implementations, the objective occurrence data acquisition operation 606 may include an operation 724 for acquiring data indicating an ingestion by the user of a medicine as depicted in FIG. 7b. For instance, the objective occurrence data acquisition module 104* of the computing device 10 or the mobile device 30 acquiring data indicating an ingestion by the user 20* of a medicine (e.g., a dosage of a beta blocker).

In some implementations, the objective occurrence data acquisition operation 606 may include an operation 726 for acquiring data indicating an ingestion by the user of a food item as depicted in FIG. 7b. For instance, the objective occurrence data acquisition module 104* of the computing device 10 or the mobile device 30 acquiring data indicating an ingestion by the user 20* of a food item (e.g., orange).

In some implementations, the objective occurrence data acquisition operation 606 may include an operation 728 for acquiring data indicating an ingestion by the user of a nutraceutical as depicted in FIG. 7b. For instance, the objective occurrence data acquisition module 104* of the computing device 10 or the mobile device 30 acquiring data indicating an ingestion by the user 20* of a nutraceutical (e.g. broccoli).

In some implementations, the objective occurrence data acquisition operation 606 may include an operation 730 for acquiring data indicating an exercise routine executed by the user as depicted in FIG. 7b. For instance, the objective occurrence data acquisition module 104* of the computing device 10 or the mobile device 30 acquiring data indicating an exercise routine executed (e.g., exercising on a exercise machine such as a treadmill) by the user 20*.

In some implementations, the objective occurrence data acquisition operation 606 may include an operation 732 for acquiring data indicating a social activity executed by the user as depicted in FIG. 7b. For instance, the objective occurrence data acquisition module 104* of the computing device 10 or the mobile device 30 acquiring data indicating a social activity (e.g., hiking or skiing with friends, dates, dinners, and so forth) executed by the user 20*.

In some implementations, the objective occurrence data acquisition operation 606 may include an operation 734 for acquiring data indicating an activity performed by a third party as depicted in FIG. 7b. For instance, the objective occurrence data acquisition module 104* of the computing device 10 or the mobile device 30 acquiring data indicating an activity performed by a third party (e.g., spouse visiting relatives).

In some implementations, the objective occurrence data acquisition operation 606 may include an operation 736 for acquiring data indicating a physical characteristic of the user as depicted in FIG. 7b. For instance, the objective occurrence data acquisition module 104* of the computing device 10 or the mobile device 30 acquiring data indicating a physical characteristic (e.g., a blood sugar level) of the user 20*. Note that a physical characteristic such as a blood sugar level could be determined using a device such as a glucometer and then reported by a user 20*, by a third party source 50, or by the device (e.g., glucometer) itself.

In some implementations, the objective occurrence data acquisition operation 606 may include an operation 738 for acquiring data indicating a resting, a learning or a recreational activity by the user as depicted in FIG. 7b. For instance, the objective occurrence data acquisition module 104* of the computing device 10 or the mobile device 30 acquiring data indicating a resting (e.g., sleeping), a learning (reading a book or attending a lecture or a class) or a recreational activity (e.g., golfing) by the user 20*.

In some implementations, the objective occurrence data acquisition operation 606 may include an operation 740 for acquiring data indicating occurrence of an external event as depicted in FIG. 7b. For instance, the objective occurrence data acquisition module 104* of the computing device 10 or the mobile device 30 acquiring data indicating occurrence of an external event (e.g., 100 degree daytime high).

In some implementations, the objective occurrence data acquisition operation 606 may include an operation 742 for acquiring data indicating a location of the user as depicted in FIG. 7b. For instance, the objective occurrence data acquisition module 104* of the computing device 10 or the mobile device 30 acquiring data indicating a location of the user 20*.

Figure 8:
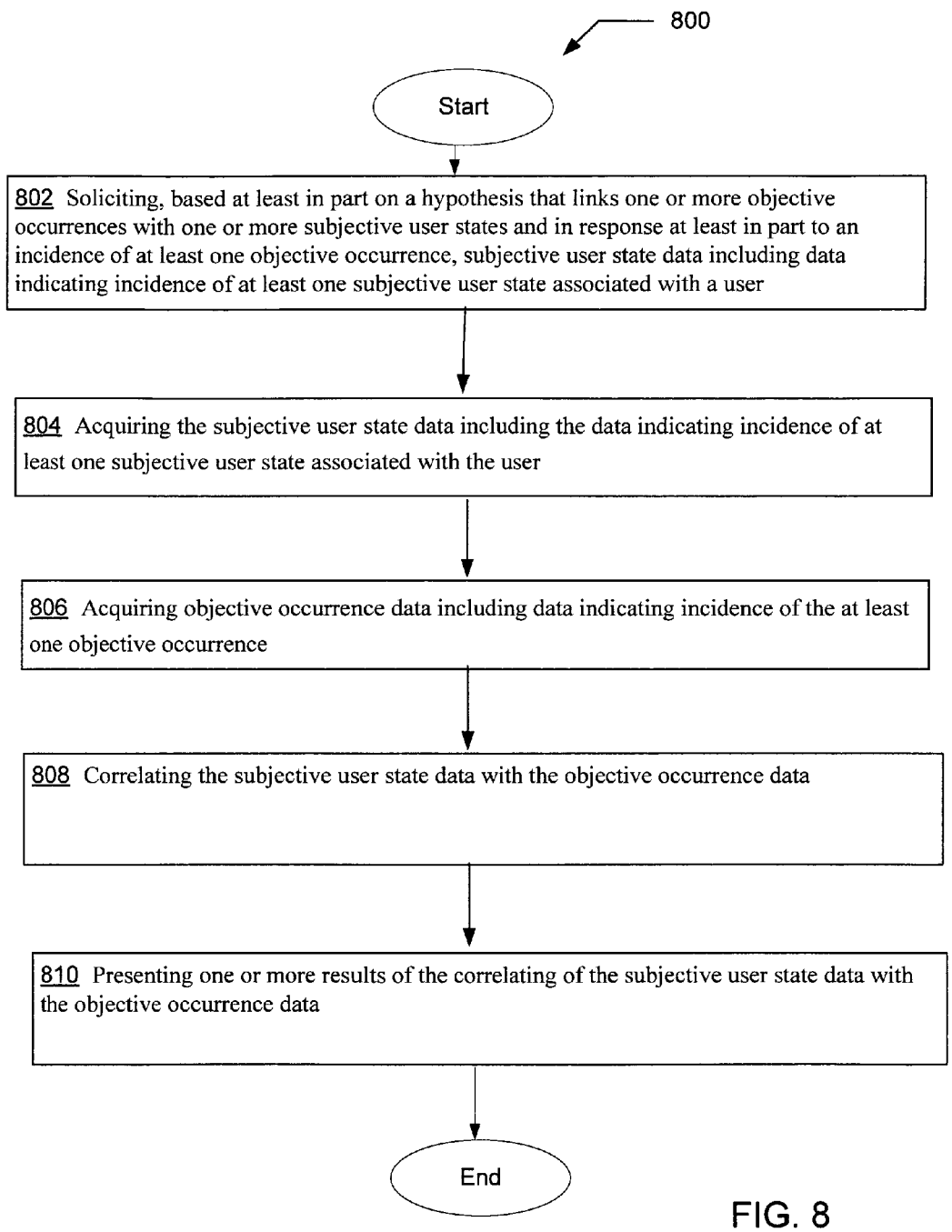
FIG. 8 is a high-level logic flowchart of still another process.

Referring now to FIG. 8 illustrating still another operational flow 800 in accordance with various embodiments. In some embodiments, operational flow 800 may be particularly suited to be performed by the computing device 10, which as previously indicated, may be a network server or a standalone device. Operational flow 800 includes operations that mirror the operations included in the operational flow 600 of FIG. 6. These operations include, for example, a subjective user state data solicitation operation 802, a subjective user state data acquisition operation 804, and an objective occurrence data acquisition operation 806 that corresponds to and mirror the subjective user state data solicitation operation 602, the subjective user state data acquisition operation 604, and the objective occurrence data acquisition operation 606, respectively, of FIG. 6.

In addition, operational flow 800 may further include a correlation operation 808 for correlating the subjective user state data with the objective occurrence data and a presentation operation 810 for presenting one or more results of the correlating of the subjective user state data with the objective occurrence data as depicted in FIG. 8. For instance, the correlation module 106 of the computing device 10 correlating (e.g., linking or determining a relationship) the subjective user state data 60 with the objective occurrence data 70*. The presentation module 108 of the computing device 10 may then present (e.g., transmit via a network interface 120 or indicate via a user interface 122) one or more results of the correlation operation performed by the correlation module 106.

Figure 9:
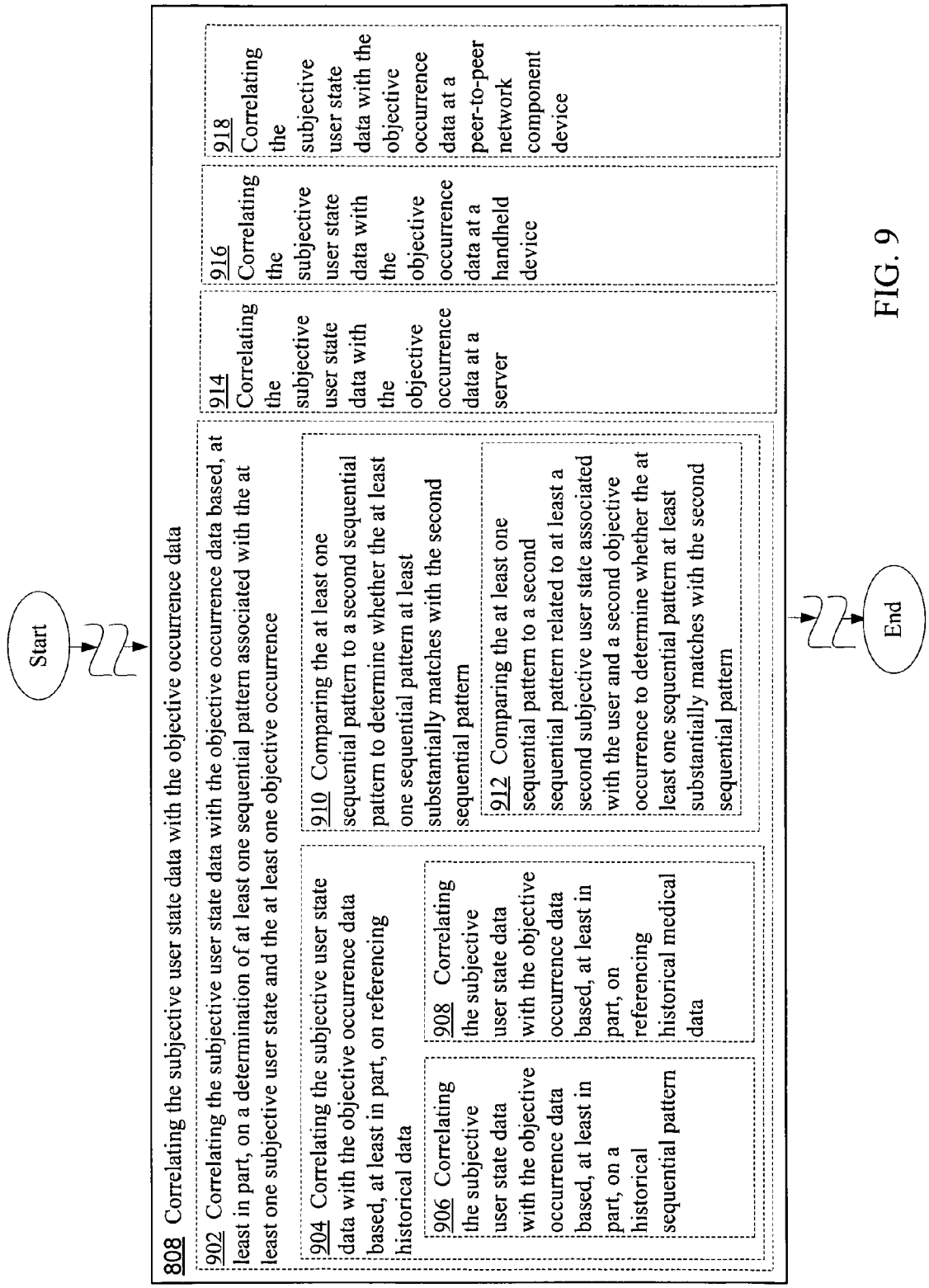
FIG. 9 is a high-level logic flowchart of a process depicting alternate implementations of the correlation operation 808 of FIG. 8.

In various alternative implementations, the correlation operation 808 may include one or more additional operations. For example, in some implementations, the correlation operation 808 may include an operation 902 for correlating the subjective user state data with the objective occurrence data based, at least in part, on a determination of at least one sequential pattern associated with the at least one subjective user state and the at least one objective occurrence as depicted in FIG. 9. For instance, the correlation module 106 of the computing device 10 correlating the subjective user state data 60 with the objective occurrence data 70* based, at least in part, on the sequential pattern determination module 242 determining at least one sequential pattern associated with the at least one subjective user state indicated by the subjective user state data 60 and the at least one objective occurrence indicated by the objective occurrence data 70*.

Operation 902, in turn, may further include one or more additional operations. For example, in some implementations, operation 902 may include an operation 904 for correlating the subjective user state data with the objective occurrence data based, at least in part, on referencing historical data as depicted in FIG. 9. For instance, the correlation module 106 of the computing device 10 correlating the subjective user state data 60 with the objective occurrence data 70* based, at least in part, on the historical data referencing module 243 referencing historical data 72. Historical data 72 may include, for example, previously reported incidences of subjective user states associated with the user 20* or with other users 20*, previously reported incidences of objective occurrences, historical sequential patterns associated with the user 20* or with other users 20*, and/or other types of historical data 72.

In some implementations, operation 904 may include an operation 906 for correlating the subjective user state data with the objective occurrence data based, at least in part, on a historical sequential pattern as depicted in FIG. 9. For instance, the correlation module 106 of the computing device 10 correlating the subjective user state data 60 with the objective occurrence data 70* based, at least in part, on the historical data referencing module 243 referencing a historical sequential pattern associated with the user 20*, with other users 20*, and/or with a subset of the general population.

In some implementations, operation 904 may include an operation 908 for correlating the subjective user state data with the objective occurrence data based, at least in part, on referencing historical medical data as depicted in FIG. 9. For instance, the correlation module 106 of the computing device 10 correlating the subjective user state data 60 with the objective occurrence data 70* based, at least in part, on the historical data referencing module 243 referencing historical medical data (e.g., genetic, metabolome, or proteome information or medical records of the user 20* or of others related to, for example, diabetes or heart disease).

In various implementations, operation 902 may include an operation 910 for comparing the at least one sequential pattern to a second sequential pattern to determine whether the at least one sequential pattern at least substantially matches with the second sequential pattern as depicted in FIG. 9. For instance, the sequential pattern comparison module 248 of the computing device 10 comparing the at least one sequential pattern to a second sequential pattern to determine whether the at least one sequential pattern at least substantially matches with the second sequential pattern.

Operation 910, in some implementations, may further include an operation 912 for comparing the at least one sequential pattern to a second sequential pattern related to at least a second subjective user state associated with the user and a second objective occurrence to determine whether the at least one sequential pattern at least substantially matches with the second sequential pattern as depicted in FIG. 9. For instance, the sequential pattern comparison module 248 of the computing device 10 comparing the at least one sequential pattern to a second sequential pattern related to at least a previously reported second subjective user state associated with the user 20* and a second previously reported objective occurrence to determine whether the at least one sequential pattern at least substantially matches with the second sequential pattern.

For these implementations, the comparison of the first sequential pattern to the second sequential pattern may involve making certain comparisons, For example, comparing the first subjective user state to the second subjective user state to determine at least whether they are the same or different. Similarly, the first objective occurrence may be compared to the second objective occurrence to determine at least whether they are the same or different. The temporal relationship or the specific time sequencing between the incidence of the first subjective user state and the incidence of the first objective occurrence (e.g., as represented by the first sequential pattern) may then be compared to the temporal relationship or the specific time sequencing between the incidence of the second subjective user state and the incidence of the second objective occurrence (e.g., as represented by the second sequential pattern).

In some implementations, the correlation operation 808 of FIG. 8 may include an operation 914 for correlating the subjective user state data with the objective occurrence data at a server as depicted in FIG. 9. For instance, when the computing device 10 is a server (e.g., network server) and the correlation module 106 correlates the subjective user state data 60 with the objective occurrence data 70*.

In alternative implementations, the correlation operation 808 may include an operation 916 for correlating the subjective user state data with the objective occurrence data at a handheld device as depicted in FIG. 9. For instance, when the computing device 10 is a standalone device, such as a handheld device, and the correlation module 106 correlates the subjective user state data 60 with the objective occurrence data 70*.

In some implementations, the correlation operation 808 may include an operation 918 for correlating the subjective user state data with the objective occurrence data at a peer-to-peer network component device as depicted in FIG. 9. For instance, when the computing device 10 is a standalone device and is a peer-to-peer network component device, and the correlation module 106 correlates the subjective user state data 60 with the objective occurrence data 70*.

Figure 10:
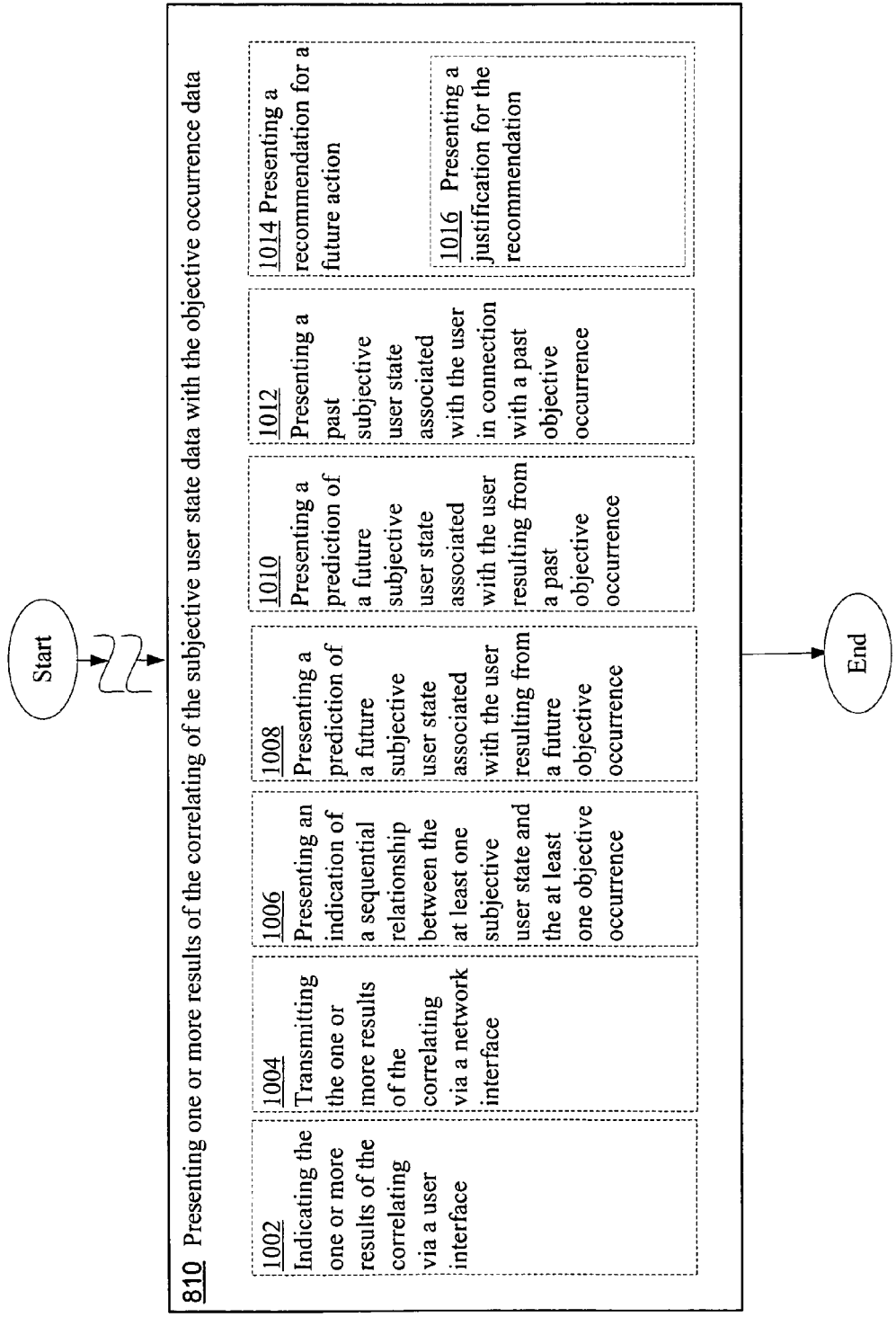
FIG. 10 is a high-level logic flowchart of a process depicting alternate implementations of the presentation operation 810 of FIG. 8.

Referring back to FIG. 8, the presentation operation 810 may include one or more additional operations in various alternative implementations. For example, in some implementations, the presentation operation 810 may include an operation 1002 for indicating the one or more results of the correlating via a user interface as depicted in FIG. 10. For instance, when the computing device 10 is a standalone device such as a handheld device (e.g., cellular telephone, PDA, and so forth) or other mobile devices, and the user interface indication module 259 of the computing device 10 indicates the one or more results of the correlation operation performed by the correlation module 106 via a user interface 122 (e.g., display monitor or audio system including a speaker).

In some implementations, the presentation operation 810 may include an operation 1004 for transmitting the one or more results of the correlating via a network interface as depicted in FIG. 10. For instance, when the computing device 10 is a server and the network interface transmission module 258 of the computing device 10 transmits the one or more results of the correlation operation performed by the correlation module 106 via a network interface 120 (e.g., NIC).

In some implementations, the presentation operation 810 may include an operation 1006 for presenting an indication of a sequential relationship between the at least one subjective user state and the at least one objective occurrence as depicted in FIG. 10. For instance, the sequential relationship presentation module 260 of the computing device 10 presenting (e.g., either by transmitting via the network interface 120 or by indicating via the user interface 122) an indication of a sequential relationship between the at least one subjective user state (e.g., happy) and the at least one objective occurrence (e.g., playing with children).

In some implementations, the presentation operation 810 may include an operation 1008 for presenting a prediction of a future subjective user state associated with the user resulting from a future objective occurrence as depicted in FIG. 10. For instance, the prediction presentation module 261 of the computing device 10 presenting (e.g., either by transmitting via the network interface 120 or by indicating via the user interface 122) a prediction of a future subjective user state associated with the user 20* resulting from a future objective occurrence (e.g., "if you drink the 24 ounces of beer you ordered, you will have a hangover tomorrow").

In some implementations, the presentation operation 810 may include an operation 1010 for presenting a prediction of a future subjective user state associated with the user resulting from a past objective occurrence as depicted in FIG. 10. For instance, the prediction presentation module 261 of the computing device 10 presenting (e.g., either by transmitting via the network interface 120 or by indicating via the user interface 122) a prediction of a future subjective user state associated with the user 20* resulting from a past objective occurrence (e.g., "you will have a stomach ache shortly because of the hot fudge sundae that you just ate").

In some implementations, the presentation operation 810 may include an operation 1012 for presenting a past subjective user state associated with the user in connection with a past objective occurrence as depicted in FIG. 10. For instance, the past presentation module 262 of the computing device 10 presenting (e.g., either by transmitting via the network interface 120 or by indicating via the user interface 122) a past subjective user state associated with the user 20* in connection with a past objective occurrence (e.g., "reason why you had a headache this morning may be because you drank that 24 ounces of beer last night").

In some implementations, the presentation operation 810 may include an operation 1014 for presenting a recommendation for a future action as depicted in FIG. 10. For instance, the recommendation module 263 of the computing device 10 presenting (e.g., either by transmitting via the network interface 120 or by indicating via the user interface 122) a recommendation for a future action (e.g., "you should buy something to calm your stomach tonight after you leave the bar tonight").

In some implementations, operation 1014 may further include an operation 1016 for presenting a justification for the recommendation as depicted in FIG. 10. For instance, the justification module 264 of the computing device 10 presenting (e.g., either by transmitting via the network interface 120 or by indicating via the user interface 122) a justification for the recommendation (e.g., "you should buy something to calm your stomach tonight since you are drinking beer tonight, and the last time you drank beer, you had an upset stomach the next morning").

Figure 11:
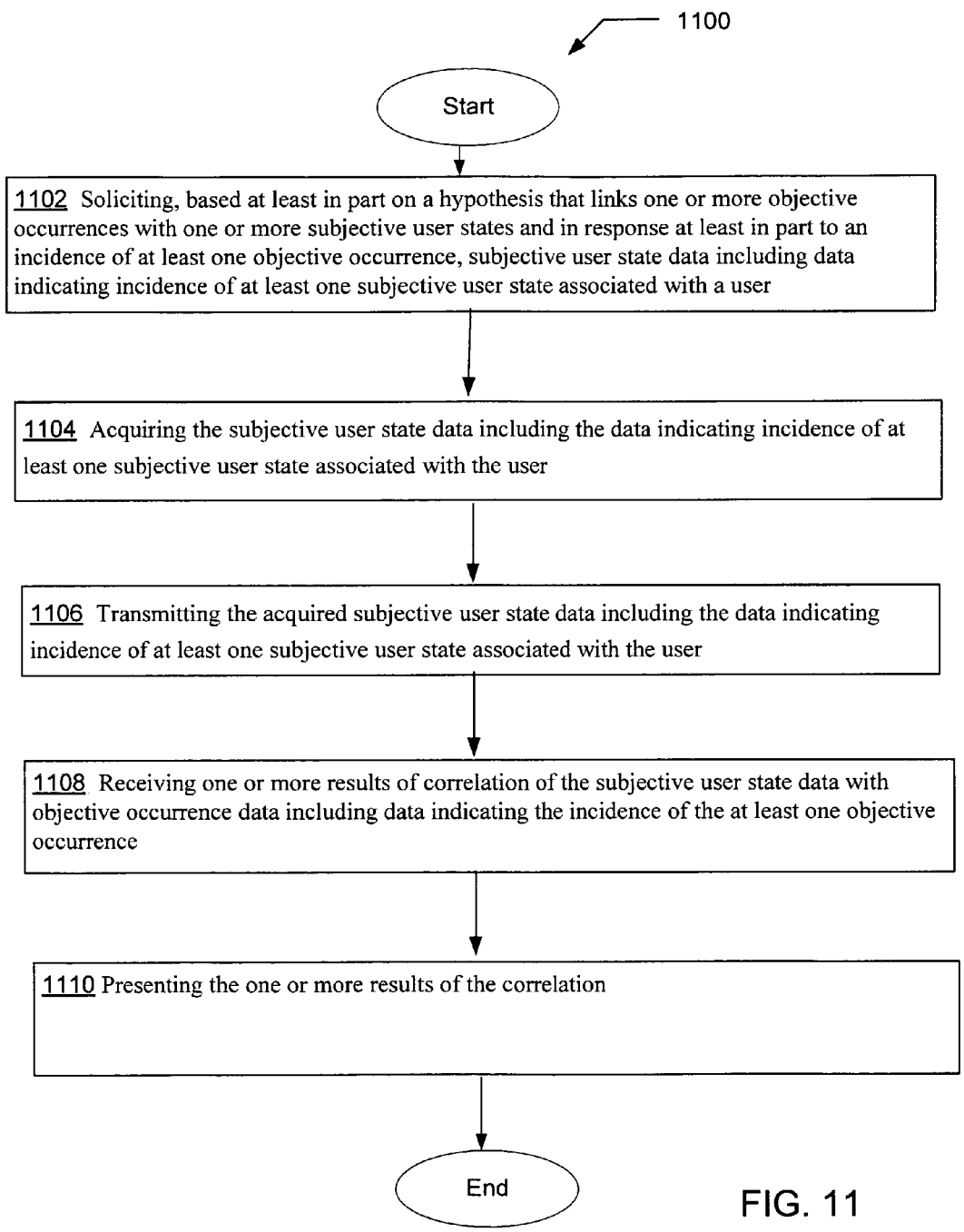
FIG. 11 is a high-level logic flowchart of still another process.

FIG. 11 illustrates another operational flow 1100 in accordance with various embodiments. In some embodiments, operational flow may be particularly suited to be performed by a mobile device 30. Operational flow 1100 includes certain operations that may completely or substantially mirror certain operations included in the operational flow 800 of FIG. 8. These operations include, for example, a subjective user state data solicitation operation 1102, a subjective user state data acquisition operation 1104, and a presentation operation 1110 that corresponds to and completely or substantially mirror the subjective user state data solicitation operation 802, the subjective user state data acquisition operation 804, and the presentation operation 810, respectively, of FIG. 8.

In addition, operational flow 1100 may further include a subjective user state data transmission operation 1106 for transmitting the acquired subjective user state data including the data indicating incidence of at least one subjective user state associated with the user and a reception operation 1108 for receiving one or more results of correlation of the subjective user state data with objective occurrence data including data indicating the incidence of the at least one objective occurrence as depicted in FIG. 11. For instance, the subjective user state data transmission module 160 of the mobile device 30 transmitting (e.g., transmitting via at least one of the wireless network or wired network 40 to, for example, a network server such as computing device 10) the acquired subjective user state data 60 including the data indicating incidence of at least one subjective user state 60*a* associated with the user 20*a*. The correlation results reception module 162 may then receive (e.g., receive from the computing device 10) one or more results of correlation of the subjective user state data 60 with objective occurrence data 70* including data indicating the incidence of the at least one objective occurrence.

Figure 12:
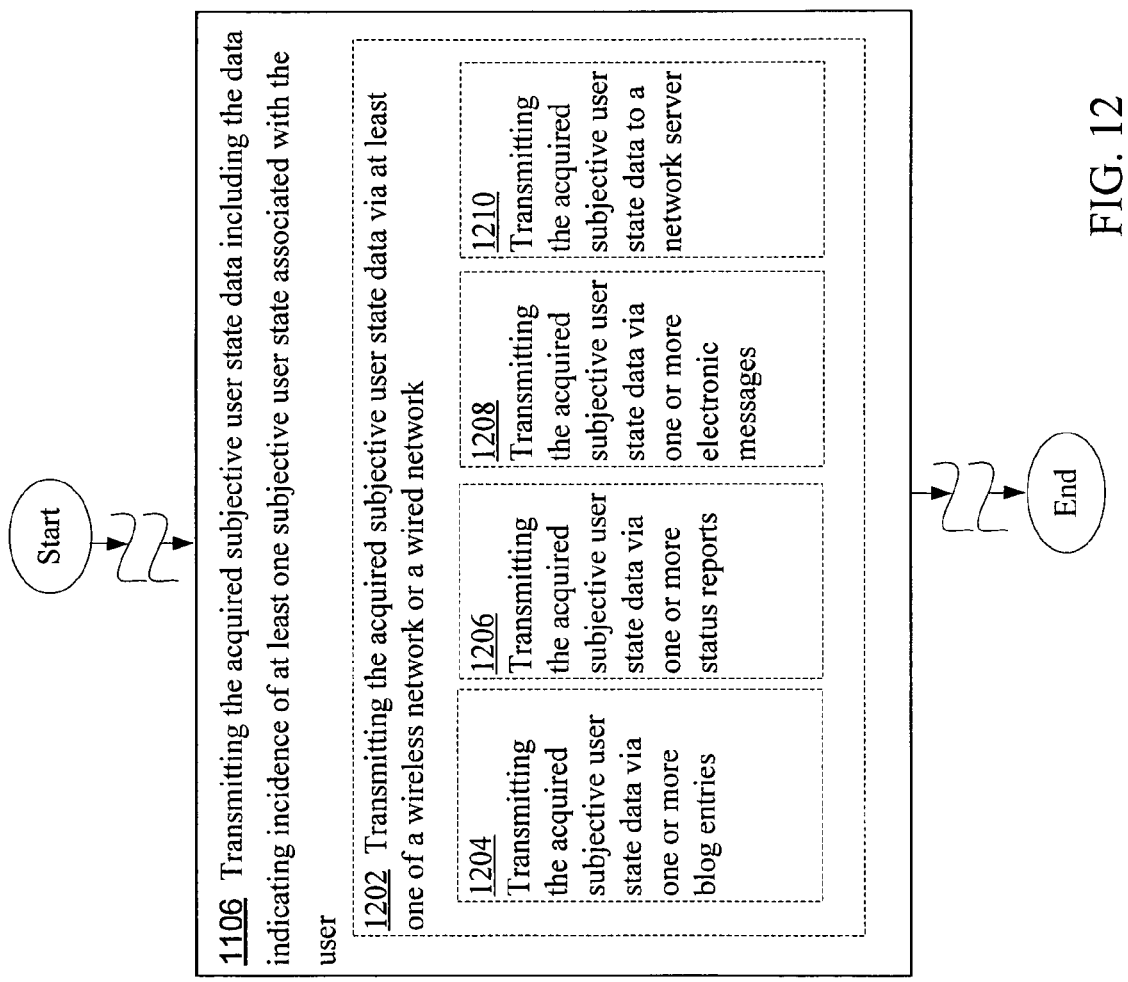
FIG. 12 is a high-level logic flowchart of a process depicting alternate implementations of the subjective user state data transmission operation 1106 of FIG. 11.

In various alternative implementations, the subjective user state data transmission operation 1106 may include one or more additional operations. For example, in some implementations, the subjective user state data transmission operation 1106 may include an operation 1202 for transmitting the acquired subjective user state data via at least one of a wireless network or a wired network as depicted in FIG. 12. For instance, the subjective user state data transmission module 160 of the mobile device 30 transmitting the acquired subjective user state data 60 via at least one of a wireless network or a wired network 40.

In some implementations, operation 1202 may include an operation 1204 for transmitting the acquired subjective user state data via one or more blog entries as depicted in FIG. 12. For instance, the subjective user state data transmission module 160 of the mobile device 30 transmitting the acquired subjective user state data 60 via one or more blog entries (e.g., microblog entries).

In some implementations, operation 1202 may include an operation 1206 for transmitting the acquired subjective user state data via one or more status reports as depicted in FIG. 12. For instance, the subjective user state data transmission module 160 of the mobile device 30 transmitting the acquired subjective user state data 60 via one or more status reports (e.g., social networking status reports).

In some implementations, operation 1202 may include an operation 1208 for transmitting the acquired subjective user state data via one or more electronic messages as depicted in FIG. 12. For instance, the subjective user state data transmission module 160 of the mobile device 30 transmitting the acquired subjective user state data 60 via one or more electronic messages (e.g., email message, IM messages, text messages, and so forth).

In some implementations, operation 1202 may include an operation 1210 for transmitting the acquired subjective user state data to a network server as depicted in FIG. 12. For instance, the subjective user state data transmission module 160 of the mobile device 30 transmitting the acquired subjective user state data 60 to a network server (e.g., computing device 10).

Figure 13:
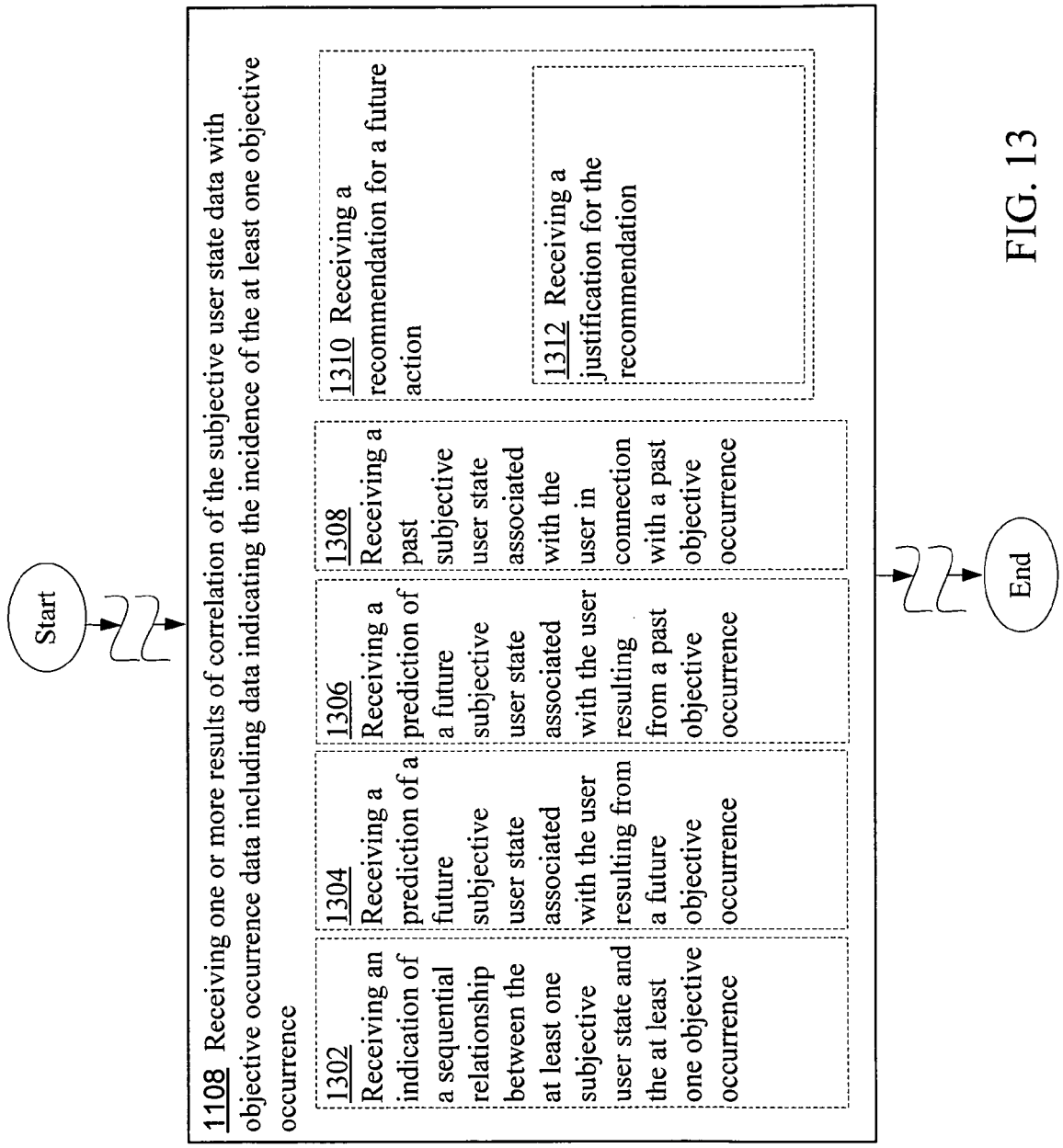
FIG. 13 is a high-level logic flowchart of a process depicting alternate implementations of the reception operation 1108 of FIG. 11.

Referring back to FIG. 11, the reception operation 1108 may include one or more additional operations in various alternative implementations. For example, in some implementations, the reception operation 1108 may include an operation 1302 for receiving an indication of a sequential relationship between the at least one subjective user state and the at least one objective occurrence as depicted in FIG. 13. For instance, the correlation results reception module 162 of the mobile device 30 receiving (e.g., via wireless network and/or wired network 40) at least an indication of a sequential relationship between the at least one subjective user state and the at least one objective occurrence. For example, receiving an indication that the user 20*a* felt energized after jogging for thirty minutes.

In some implementations, the reception operation 1108 may include an operation 1304 for receiving a prediction of a future subjective user state associated with the user resulting from a future objective occurrence as depicted in FIG. 13. For instance, the correlation results reception module 162 of the mobile device 30 receiving (e.g., via wireless network and/or wired network 40) at least a prediction of a future subjective user state (e.g., feeling energized) associated with the user 20*a* resulting from a future objective occurrence (e.g., jogging for 30 minutes).

In some implementations, the reception operation 1108 may include an operation 1306 for receiving a prediction of a future subjective user state associated with the user resulting from a past objective occurrence as depicted in FIG. 13. For instance, the correlation results reception module 162 of the mobile device 30 receiving (e.g., via wireless network and/or wired network 40) at least a prediction of a future subjective user state (e.g., easing of pain) associated with the user 20*a* resulting from a past objective occurrence (e.g., previous ingestion of aspirin).

In some implementations, the reception operation 1108 may include an operation 1308 for receiving a past subjective user state associated with the user in connection with a past objective occurrence as depicted in FIG. 13. For instance, the correlation results reception module 162 of the mobile device 30 receiving (e.g., via wireless network and/or wired network 40) at least an indication of a past subjective user state (e.g., depression) associated with the user 20*a* in connection with a past objective occurrence (e.g., overcast weather).

In some implementations, the reception operation 1108 may include an operation 1310 for receiving a recommendation for a future action as depicted in FIG. 13. For instance, the correlation results reception module 162 of the mobile device 30 receiving (e.g., via wireless network and/or wired network 40) at least a recommendation for a future action (e.g., "you should go to sleep early").

In certain implementations, operation 1310 may further include an operation 1312 for receiving a justification for the recommendation as depicted in FIG. 13. For instance, the correlation results reception module 162 of the mobile device 30 receiving (e.g., via wireless network and/or wired network 40) at least a justification for the recommendation (e.g., "last time you stayed up late, you were very tired the next morning").

Figure 14:
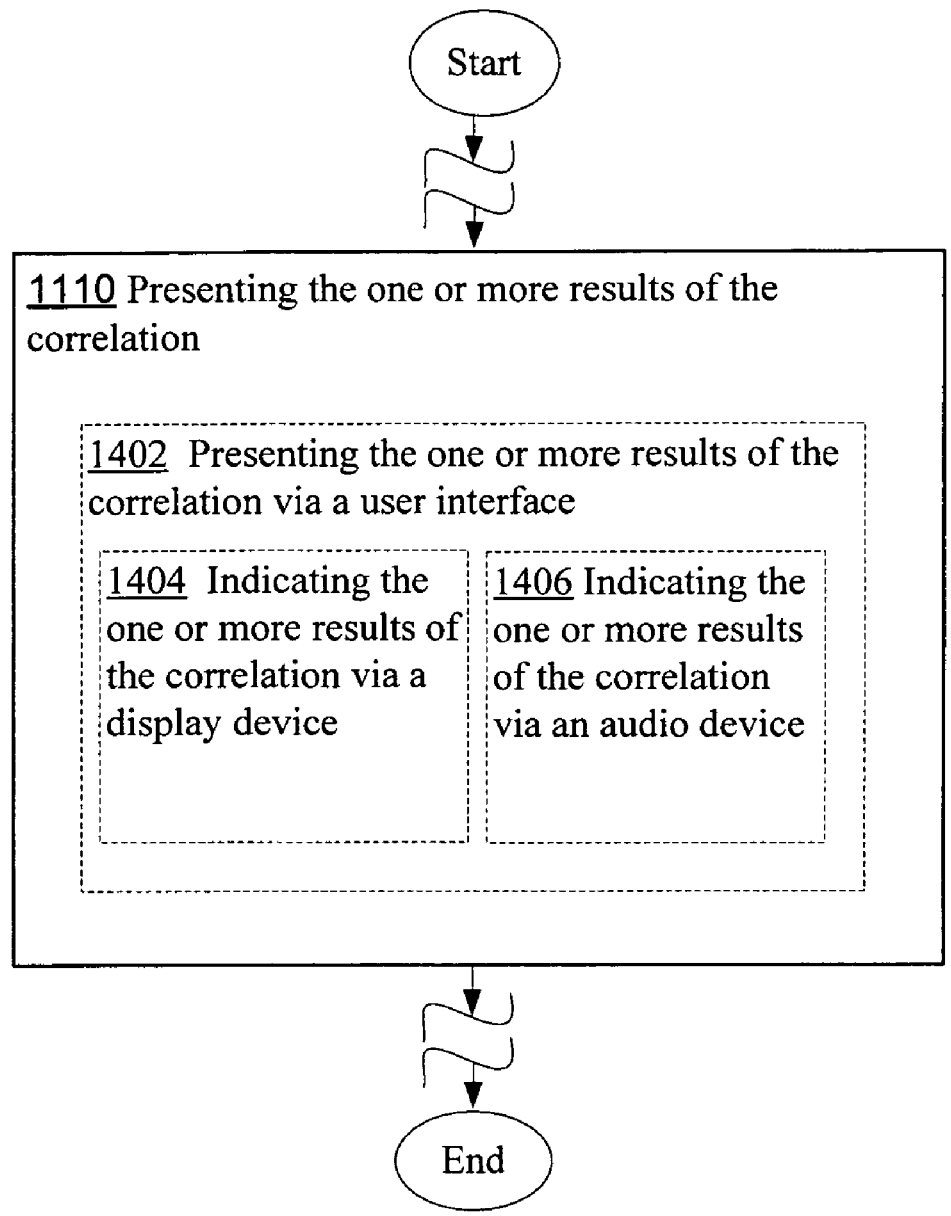
FIG. 14 is a high-level logic flowchart of a process depicting alternate implementations of the presentation operation 1110 of FIG. 11.

Referring back to FIG. 11 the process 1100 in various implementations may include a presentation operation 1110 for presenting the one or more results of the correlation. For example, the presentation module 108' of the mobile device 30 presenting the one or more results of the correlation received by the correlation results reception module 162. The presentation operation 1110 of FIG. 11 in some implementations may completely or substantially mirror the presentation operation 810 of FIG. 8. For instance, in some implementations, the presentation operation 1110 may include, similar to the presentation operation 810 of FIG. 8, an operation 1402 for indicating the one or more results of the correlation via a user interface as depicted in FIG. 14. For instance, the user interface indication module 259' of the mobile device 30 indicating the one or more results of the correlation via a user interface 122'.

In some implementations, operation 1402 may further include an operation 1404 for indicating the one or more results of the correlation via a display device as depicted in FIG. 14. For instance, the user interface indication module 259' of the mobile device 30 indicating the one or more results of the correlation via a display device (e.g., a display monitor such as a liquid crystal display or a touchscreen).

In some implementations, operation 1402 may include an operation 1406 for indicating the one or more results of the correlation via an audio device as depicted in FIG. 14. For instance, the user interface indication module 259' of the mobile device 30 indicating the one or more results of the correlation via an audio device (e.g., a speaker).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented system, comprising:
   means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user; and
   means for acquiring the subjective user state data including the data indicating incidence of at least one subjective user state associated with the user.

2. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
   means for requesting for the data indicating incidence of at least one subjective user state associated with the user.

3. The computationally-implemented system of claim 2, wherein said means for requesting for the data indicating incidence of at least one subjective user state associated with the user comprises:
   means for requesting for the data indicating incidence of at least one subjective user state associated with the user via a user interface.

4. The computationally-implemented system of claim 3, wherein said means for requesting for the data indicating incidence of at least one subjective user state associated with the user via a user interface comprises:
   means for requesting for the data indicating incidence of at least one subjective user state associated with the user from the user.

5. The computationally-implemented system of claim 2, wherein said means for requesting for the data indicating incidence of at least one subjective user state associated with the user comprises:
   means for requesting for the data indicating incidence of at least one subjective user state associated with the user via network interface.

6. The computationally-implemented system of claim 5, wherein said means for requesting for the data indicating incidence of at least one subjective user state associated with the user via network interface comprises:
   means for transmitting a request to be provided with the data indicating incidence of at least one subjective user state associated with the user.

7. The computationally-implemented system of claim 5, wherein said means for requesting for the data indicating incidence of at least one subjective user state associated with the user via network interface comprises:
   means for transmitting a request to have access to the data indicating incidence of at least one subjective user state associated with the user.

8. The computationally-implemented system of claim 5, wherein said means for requesting for the data indicating incidence of at least one subjective user state associated with the user via network interface comprises:
   means for directing or instructing a remote device to provide the data indicating incidence of at least one subjective user state associated with the user.

9. The computationally-implemented system of claim 2, wherein said means for requesting for the data indicating incidence of at least one subjective user state associated with the user comprises:
   means for providing a motivation for requesting for the data indicating incidence of at least one subjective user state associated with the user.

10. The computationally-implemented system of claim 9, wherein said means for providing a motivation for requesting for the data indicating incidence of at least one subjective user state associated with the user comprises:

means for providing a motivation for requesting for the data indicating incidence of at least one subjective user state associated with the user, the motivation to be provided relating to the link between the one or more objective occurrences with the one or more subjective user states as indicated by the hypothesis.

11. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting from the user the data indicating incidence of at least one subjective user state associated with the user.

12. The computationally-implemented system of claim 11, wherein said means for soliciting from the user the data indicating incidence of at least one subjective user state associated with the user comprises:
means for requesting the user to select a subjective user state from a plurality of indicated alternative subjective user states.

13. The computationally-implemented system of claim 11, wherein said means for soliciting from the user the data indicating incidence of at least one subjective user state associated with the user comprises:
means for requesting the user to confirm incidence of at least one subjective user state.

14. The computationally-implemented system of claim 11, wherein said means for soliciting from the user the data indicating incidence of at least one subjective user state associated with the user comprises:
means for requesting the user to provide an indication of occurrence of at least one subjective user state with respect to the incidence of the at least one objective occurrence.

15. The computationally-implemented system of claim 11, wherein said means for soliciting from the user the data indicating incidence of at least one subjective user state associated with the user comprises:
means for requesting the user to provide an indication of a time or temporal element associated with the incidence of at least one subjective user state associated with the user.

16. The computationally-implemented system of claim 15, wherein said means for requesting the user to provide an indication of a time or temporal element associated with the incidence of at least one subjective user state associated with the user comprises:
means for requesting the user to provide an indication of a temporal relationship between the incidence of the at least one subjective user state associated with the user and the incidence of the at least one objective occurrence.

17. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting data indicating incidence of at least one subjective mental state associated with the user.

18. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting data indicating incidence of at least one subjective physical state associated with the user.

19. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting data indicating incidence of at least one subjective overall state associated with the user.

20. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting data indicating incidence of at least one subjective user state that occurred during a specified point in time or time interval.

21. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:
means for soliciting the data indicating incidence of at least one subjective user state based, at least in part, on referencing the hypothesis.

22. The computationally-implemented system of claim 21, wherein said means for soliciting the data indicating incidence of at least one subjective user state based, at least in part, on referencing the hypothesis comprises:
means for soliciting the data indicating incidence of at least one subjective user state associated with the user based, at least in part, on referencing a hypothesis that identifies one or more temporal relationships between the one or more objective occurrences and the one or more subjective user states.

23. The computationally-implemented system of claim 22, wherein said means for soliciting the data indicating incidence of at least one subjective user state associated with the user based, at least in part, on referencing a hypothesis that identifies one or more temporal relationships between the one or more objective occurrences and the one or more subjective user states comprises:
means for soliciting the data indicating incidence of at least one subjective user state associated with the user based, at least in part, on referencing a hypothesis that identifies one or more time sequential relationships between the at least one objective occurrences and the one or more subjective user states.

24. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between at least an ingestion of a medicine, a food item, or a nutraceutical and the one or more subjective user states.

25. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between execution of one or more exercise routines and the one or more subjective user states.

26. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between execution of one or more social activities and the one or more subjective user states.

27. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between one or more activities executed by a third party and the one or more subjective user states.

28. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between one or more physical characteristics of the user and the one or more subjective user states.

29. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between a resting, a learning, or a recreation activity performed by the user and the one or more subjective user states.

30. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between one or more external activities and the one or more subjective user states.

31. The computationally-implemented system of claim 21, wherein said means for soliciting the data indicating incidence of at least one subjective user state based, at least in part, on referencing the hypothesis comprises:

means for soliciting the data indicating incidence of at least one subjective user state associated with the user based, at least in part, on referencing a hypothesis that identifies a relationship between one or more locations of the user and the one or more subjective user states.

32. The computationally-implemented system of claim 1, wherein said means for soliciting, based at least in part on a hypothesis that links one or more objective occurrences with one or more subjective user states and in response at least in part to an incidence of at least one objective occurrence, subjective user state data including data indicating incidence of at least one subjective user state associated with a user comprises:

means for soliciting the data indicating incidence of at least one subjective user state associated with the user in response to a reception of a request to solicit the data indicating incidence of at least one subjective user state associated with the user, the request to solicit being remotely generated based, at least in part, on the hypothesis.

33. The computationally-implemented system of claim 32, wherein said means for soliciting the data indicating incidence of at least one subjective user state associated with the user in response to a reception of a request to solicit the data indicating incidence of at least one subjective user state associated with the user, the request to solicit being remotely generated based, at least in part, on the hypothesis comprises:

means for soliciting the data indicating incidence of at least one subjective user state associated with the user in response to a reception of a request to solicit the data indicating incidence of at least one subjective user state associated with the user, the request to solicit being remotely generated based, at least in part, on the hypothesis and in response to the incidence of the at least one objective occurrence.

34. The computationally-implemented system of claim 32, wherein said means for soliciting the data indicating incidence of at least one subjective user state associated with the user in response to a reception of a request to solicit the data indicating incidence of at least one subjective user state associated with the user, the request to solicit being remotely generated based, at least in part, on the hypothesis comprises:

means for receiving the request to solicit the data indicating incidence of at least one subjective user state associated with the user via at least one of a wireless network or a wired network.

35. The computationally-implemented system of claim 34, wherein said means for receiving the request to solicit the data indicating incidence of at least one subjective user state associated with the user via at least one of a wireless network or a wired network comprises:

means for receiving the request to solicit the data indicating incidence of at least one subjective user state associated with the user from a network server.

36. The computationally-implemented system of claim 1, wherein said means for acquiring the subjective user state data including the data indicating incidence of at least one subjective user state associated with the user comprises:

means for receiving the subjective user state data including the data indicating incidence of at least one subjective user state associated with the user.

37. The computationally-implemented system of claim 36, wherein said means for receiving the subjective user state data including the data indicating incidence of at least one subjective user state associated with the user comprises:

means for receiving the subjective user state data including the data indicating incidence of at least one subjective user state associated with the user from at least one of a wireless network or a wired network.

38. The computationally-implemented system of claim 37, wherein said means for receiving the subjective user state data including the data indicating incidence of at least one subjective user state associated with the user from at least one of a wireless network or a wired network comprises:
   means for receiving the subjective user state data including data indicating incidence of at least one subjective user state associated with the user via one or more electronic messages generated by the user.

39. The computationally-implemented system of claim 37, wherein said means for receiving the subjective user state data including the data indicating incidence of at least one subjective user state associated with the user from at least one of a wireless network or a wired network comprises:
   means for receiving the subjective user state data including data indicating incidence of at least one subjective user state associated with the user via one or more blog entries generated by the user.

40. The computationally-implemented system of claim 37, wherein said means for receiving the subjective user state data including the data indicating incidence of at least one subjective user state associated with the user from at least one of a wireless network or a wired network comprises:
   means for receiving the subjective user state data including data indicating incidence of at least one subjective user state associated with the user via one or more status reports generated by the user.

41. A computationally-implemented method, comprising:
   soliciting, based at least in part on a hypothesis that links one or more objective occurrences with one or more subjective user states and in response at least in part to an incidence of at least one objective occurrence, subjective user state data including data indicating incidence of at least one subjective user state associated with a user, wherein said soliciting, based at least in part on a hypothesis that links one or more objective occurrences with one or more subjective user states and in response at least in part to an incidence of at least one objective occurrence, subjective user state data including data indicating incidence of at least one subjective user state associated with a user is performed via at least one of a machine, article of manufacture, or composition of matter; and
   acquiring the subjective user state data including the data indicating incidence of at least one subjective user state associated with the user.

* * * * *